United States Patent
LaChance et al.

(10) Patent No.: US 10,451,644 B2
(45) Date of Patent: Oct. 22, 2019

(54) LIQUID DISPENSER WITH MANIFOLD MOUNT FOR MODULAR INDEPENDENTLY-ACTUATED PIPETTE CHANNELS

(71) Applicant: BECTON, DICKINSON AND COMPANY, Franklin Lakes, NJ (US)

(72) Inventors: Stephen LaChance, Cockeysville, MD (US); Alyssa Shedlosky, Pikesville, MD (US); Alexander Clark, Baltimore, MD (US); Redeat Girma Alemu, Cockeysville, MD (US); Craig Bark, Fallston, MD (US); Steven Charles Rotundo, Baltimore, MD (US); Michael T. Vansickler, Columbia, MD (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 0 days.

(21) Appl. No.: 16/193,452

(22) Filed: Nov. 16, 2018

(65) Prior Publication Data
US 2019/0086436 A1    Mar. 21, 2019

Related U.S. Application Data

(63) Continuation of application No. PCT/US2017/018282, filed on Feb. 17, 2017.
(Continued)

(51) Int. Cl.
*B01L 3/02*     (2006.01)
*G01N 1/00*     (2006.01)
(Continued)

(52) U.S. Cl.
CPC .......... *G01N 35/1072* (2013.01); *B01L 3/021* (2013.01); *B01L 3/0275* (2013.01);
(Continued)

(58) Field of Classification Search
CPC combination set(s) only.
See application file for complete search history.

(56) References Cited

U.S. PATENT DOCUMENTS

| 5,916,524 | A  | 6/1999 | Tisone |
| 7,217,395 | B2 | 5/2007 | Sander |

(Continued)

FOREIGN PATENT DOCUMENTS

| CN | 104330580 | 2/2015 |
| EP | 1059458 A2 | 12/2000 |

(Continued)

OTHER PUBLICATIONS

International Search Report and Written Opinion for Int'l Application No. PCT/US2017/018282, dated Feb. 17, 2017.
(Continued)

*Primary Examiner* — Brian R Gordon
(74) *Attorney, Agent, or Firm* — Knobbe, Martens, Olson & Bear, LLP

(57) ABSTRACT

Automated pipetting systems and methods are disclosed for aspirating and dispensing fluids, particularly biological samples. In one aspect, a liquid dispenser includes a manifold and one or more pipette channels. The manifold includes a vacuum channel, a pressure channel, and a plurality of lanes. Each lane includes an electrical connector, a port to the pressure channel, and a port to the vacuum channel. The pipette channels can be modular. Each pipette channel includes a single dispense head and can be selectively and independently coupled to any one lane of the plurality of lanes. In some aspects, a valve in the pipette
(Continued)

channel is in simultaneous fluid communication with a pressure port and a vacuum port of the manifold. The valve selectively diverts gas under pressure and gas under vacuum to the dispense head in response to control signals received through the electrical connector of the manifold.

77 Claims, 67 Drawing Sheets

Related U.S. Application Data

(60) Provisional application No. 62/409,695, filed on Oct. 18, 2016, provisional application No. 62/340,296, filed on May 23, 2016.

(51) Int. Cl.
| | | |
|---|---|---|
| *G01N 1/10* | (2006.01) | |
| *G01N 35/10* | (2006.01) | |
| *G01N 1/18* | (2006.01) | |
| *B01L 3/00* | (2006.01) | |
| *G01N 1/14* | (2006.01) | |

(52) U.S. Cl.
CPC ........ *B01L 3/50273* (2013.01); *B01L 3/527* (2013.01); *G01N 1/14* (2013.01); *G01N 1/18* (2013.01); *G01N 35/10* (2013.01); *B01L 2200/143* (2013.01); *B01L 2200/148* (2013.01); *B01L 2400/043* (2013.01); *B01L 2400/049* (2013.01); *B01L 2400/0487* (2013.01); *B01L 2400/06* (2013.01); *B01L 2400/0666* (2013.01); *G01N 2001/1418* (2013.01); *G01N 2035/1027* (2013.01)

(56) References Cited

U.S. PATENT DOCUMENTS

| | | |
|---|---|---|
| 7,270,789 B1 | 9/2007 | Astle |
| 7,413,710 B2 | 8/2008 | Lisec et al. |
| 8,021,611 B2 | 9/2011 | Roach et al. |
| 8,283,181 B2 | 10/2012 | Pinkel et al. |
| 8,287,820 B2 | 10/2012 | Williams et al. |
| 8,900,878 B2 | 12/2014 | Haack et al. |
| 8,920,752 B2 | 12/2014 | Tisone et al. |
| 9,347,586 B2 | 5/2016 | Williams et al. |
| 2005/0196304 A1 | 9/2005 | Richter et al. |
| 2007/0048188 A1 | 3/2007 | Bigus |
| 2007/0134808 A1 | 6/2007 | Sullivan |
| 2008/0240898 A1 | 10/2008 | Manz et al. |
| 2010/0120129 A1 | 5/2010 | Amshey et al. |
| 2011/0097493 A1 | 4/2011 | Kerr et al. |
| 2011/0127292 A1 | 6/2011 | Sarofim et al. |
| 2011/0287447 A1 | 11/2011 | Norderhaug |
| 2016/0038942 A1 | 2/2016 | Roberts |
| 2016/0303556 A1 | 10/2016 | Kopp et al. |
| 2017/0097373 A1 | 4/2017 | Williams et al. |
| 2018/0246134 A1 | 8/2018 | LaChance et al. |

FOREIGN PATENT DOCUMENTS

| | | |
|---|---|---|
| EP | 1941283 | 12/2009 |
| EP | 2144067 | 4/2012 |
| WO | WO 2010/130310 | 11/2010 |

OTHER PUBLICATIONS

Zeus™ Air Displacement Pipetting Module, Hamilton Company Brochure, Aug. 2013.
Hamilton Zeus™ Pipetting Module, Hamilton Company Specification Sheet, Sep. 2013.
Z-Excursion Universal Sampler (ZEUS) Integrator Manual, Hamilton Company, Aug. 2013.

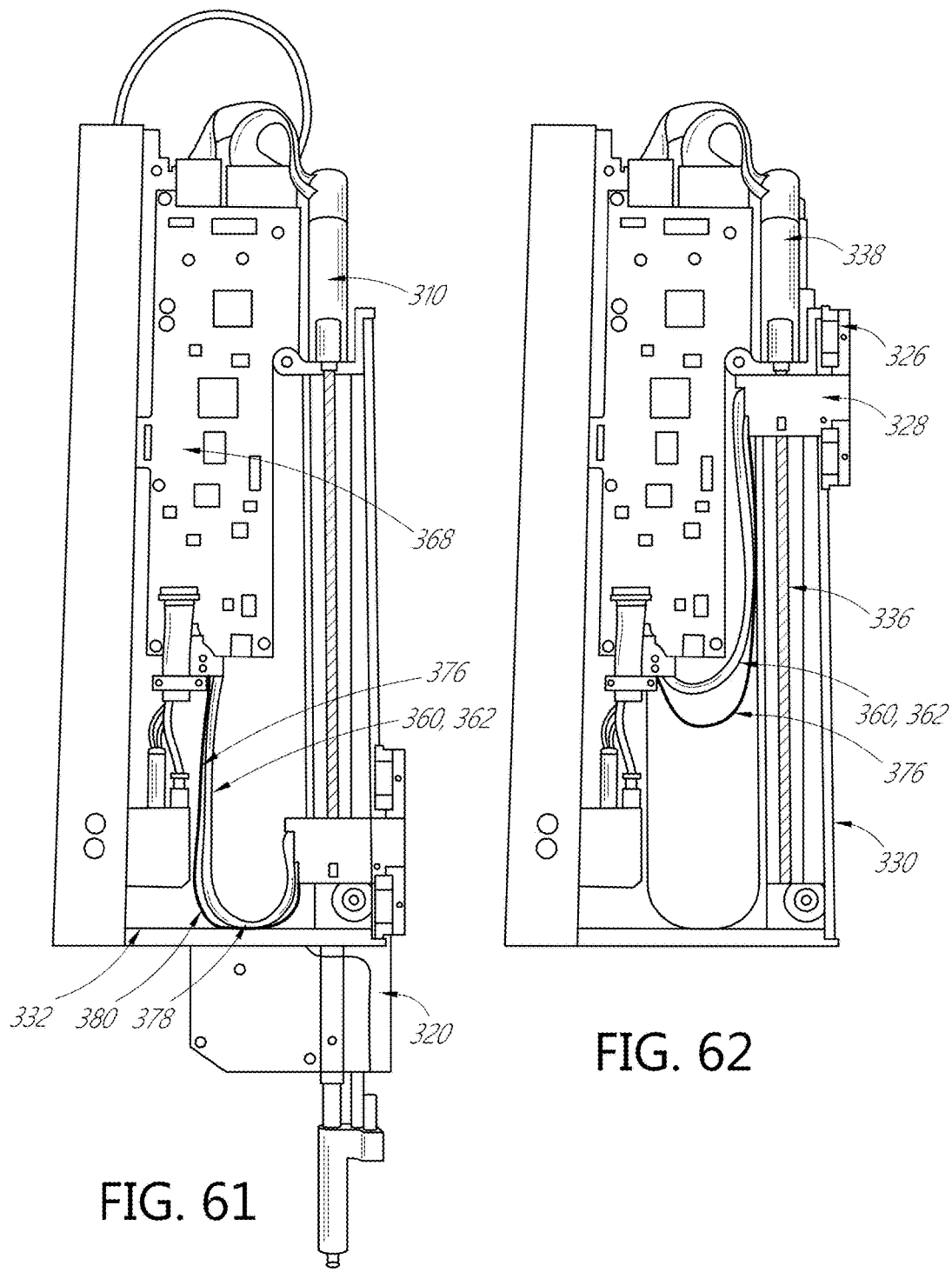

LIQUID DISPENSER WITH MANIFOLD MOUNT FOR MODULAR INDEPENDENTLY-ACTUATED PIPETTE CHANNELS

CROSS REFERENCE TO RELATED APPLICATIONS

This application is a continuation of International Application PCT/US2017/018282, filed Feb. 17, 2017, which claims the benefit of U.S. Provisional Application No. 62/340,296, filed May 23, 2016, and U.S. Provisional Application No. 62/409,695, filed Oct. 18, 2016, all of which are hereby incorporated by reference in their entirety.

BACKGROUND

Field

The technology described herein generally relates to systems and methods for controlling fluid processing operations associated with liquid dispense operations of fluids including samples, particularly multiple biological samples. The technology relates to automated pipetting systems to carry out various aspirate and dispense operations.

Description of the Related Art

Diagnostic testing of biological samples is instrumental in the health care industry's efforts to quickly and effectively diagnose and treat disease. Clinical laboratories that perform such diagnostic testing already receive hundreds or thousands of samples on a daily basis with an ever increasing demand. The challenge of managing such large quantities of samples has been assisted by the automation of sample analysis. Automated sample analysis is typically performed by automated analyzers that are commonly self-contained systems which perform multistep processes on the biological samples to obtain diagnostic results.

Understanding that sample flow breaks down into several key steps, it would be desirable to consider ways to automate as many of these as possible. For example, a biological sample, once extracted from a patient, must be put in a form suitable for a processing regime. In some cases, the processing regime involves DNA amplification, using polymerase chain reaction (PCR) or another suitable technique, to amplify a vector of interest. Clinical laboratories also have different automated clinical analyzers performing different processing regimes. Thus, there is a need to prepare samples for diagnostic testing with a universal liquid handling system that can be easily customized and implemented in different types of analyzers.

Sample preparation is labor intensive in part because of the number of liquids, such as reagents, that are required, and the need for multiple liquid transfer (e.g., pipetting) operations. Thus, there is a need for an automated pipetting apparatus, particularly one that can operate on multiple samples in parallel.

The discussion of the background herein is included to explain the context of the inventions described herein. This is not to be taken as an admission that any of the material referred to was published, known, or part of the common general knowledge as of the priority date of any of the claims.

Throughout the description and claims of the specification the word "comprise" and variations thereof, such as "comprising" and "comprises," is not intended to exclude other additives, components, integers or steps.

SUMMARY

A liquid dispenser described herein includes a manifold comprising a pressure channel, a vacuum channel, a plurality of pressure cross-channels, each pressure cross-channel beginning at the pressure channel and terminating at an external surface of the manifold, a plurality of vacuum cross-channels, each vacuum cross-channel beginning at the vacuum channel and terminating at the external surface of the manifold. The liquid dispenser includes one or more pipette channels coupled to the manifold, each pipette channel comprising a dispense head, a pressure port configured to receive gas under pressure from one pressure cross-channel, a vacuum port configured to receive gas under vacuum from one vacuum cross-channel, and a valve in simultaneous fluid communication with the pressure port and the vacuum port, the valve operable to selectively divert gas under pressure and gas under vacuum to the dispense head. The liquid dispenser includes electrical connections configured to transmit control signals from the manifold to the one or more pipette channels, operation of each valve regulated independently of any other valve by the control signals transmitted from the manifold.

In some embodiments, each of the one or more pipette channels are selectively and independently coupled to the manifold. In some embodiments, for each pipette channel, the dispense head is coupled to a pipette tip, wherein the dispense head is configured to aspirate a liquid into the pipette tip when the valve diverts gas under vacuum to the dispense head, and wherein the dispense head is configured to dispense a liquid from the pipette tip when the valve diverts gas under pressure to the dispense head. In some embodiments, each pipette channel comprises a single dispense head. In some embodiments, each valve is configured to selectively distribute gas under pressure and gas under vacuum from the pressure port and the vacuum port, respectively, to the single dispense head. In some embodiments, each pipette channel comprises a first portion that does not move relative to the manifold when the pipette channel is coupled to the manifold and a second portion that moves relative to the manifold when the pipette channel is coupled to the manifold. In some embodiments, the valve is enclosed within the first portion, the dispense head is coupled to the second portion, and a tube connecting the valve and the dispense head is configured to move within the first portion when the second portion moves relative to the first portion. In some embodiments, the pressure channel comprises a first end and a second end terminating at an inlet pressure port, wherein the inlet pressure port is connected to an external source of gas under pressure, wherein the vacuum channel comprises a first end and a second end terminating at an inlet vacuum port, and wherein the inlet vacuum port is connected to an external source of gas under vacuum. In some embodiments, the manifold only accepts gas under pressure and gas under vacuum through the inlet pressure port and the inlet vacuum port, respectively. In some embodiments, the electrical connections are further configured to transmit electrical signals from the manifold to the one or more pipette channels, each pipette channel powered independently of any pipette channel by the electrical signals transmitted from the manifold. In some embodiments, each of the one or more pipette channels only receives control signals and electrical signals through the electrical connection with the manifold. In some embodiments, each valve is a three way solenoid valve. In some embodiments, each valve is a low pressure solenoid valve. In some embodiments, each valve is a solenoid valve rated for less than 10 psi. In some embodiments, at least one pipette channel further comprises a magnetic brake. In some embodiments, the magnetic brake is configured to reduce free-fall of the dispense head of the at least one pipette channel in the event of loss of electrical signals from the manifold. In some embodiments, at least one pipette channel further comprises a ball screw configured to move the dispense head of the at least one pipette channel in a vertical direction relative to the manifold. In some embodiments, the at least one pipette channel further comprises a coupling configured to reduce misalignment of the ball screw. In some embodiments, gas provided by each pressure cross-channel to the pressure port of the respective pipette channel is at the same pressure as gas provided by each other pressure cross-channel of the plurality of pressure cross-channels. In some embodiments, the manifold further comprises a second pressure channel comprising a plurality of pressure cross-channels, wherein the pressure port of each of a first plurality of pipette channels is coupled to one pressure cross-channel of the first pressure channel, wherein the pressure port of each of a second, different plurality of pipette channels is coupled to one pressure cross-channel of the second pressure channel, and wherein the manifold provides gas under pressure to the first plurality of pipette channels at a first pressure and simultaneously provides gas to the second plurality of pipette channels at a second, different pressure. In some embodiments, each pipette channel is configured to be selectively mounted to the manifold with two screws. In some embodiments, the two screws are captive to the pipette channel. In some embodiments, at least one pipette channel comprises one or more pegs configured to align with one or more openings of the manifold. In some embodiments, the one or more pegs engage the one or more openings in the manifold before an electrical connector on the pipette channel and an electrical connector on the manifold engage. In some embodiments, each pipette channel comprises one or more o-rings configured to provide a seal between each pipette channel and the manifold. In some embodiments, the one or more o-rings are captured in a dove-tail groove in each pipette channel. In some embodiments, the liquid dispenser includes a first pipette channel and a second pipette channel coupled to the manifold, wherein the first pipette channel comprises a different calibration setting for dispensing. In some embodiments, two or more pipette channels have different dispense heads. In some embodiments, one pressure cross-channel and one vacuum cross-channel are not coupled to a pipette channel, and wherein the liquid dispenser further comprises a blanking plate configured to close the one pressure cross-channel and the one vacuum cross-channel of the manifold that are not coupled to a pipette channel. In some embodiments, the pressure channel and the vacuum channel are physically and fluidically isolated from each other within the manifold. In some embodiments, the manifold comprises a single pressure channel and a single vacuum channel. In some embodiments, for each pipette channel, the valve is configured to be in simultaneous fluid communication with the pressure channel and the vacuum channel of the manifold, the valve operable to selectively divert gas under pressure and gas under vacuum to the dispense head. In some embodiments, each pipette channel further comprises a tube, the tube having a first end terminating at the valve and a second end terminating at the dispense head, wherein the tube is configured to direct gas from the valve to the dispense head. In some embodiments, the tube is the only pneumatic connection between the valve and the dispense head. In some embodiments, the tube is configured to bend as the dispense head moves vertically relative to the manifold. In some embodiments, the tube is enclosed by an outer housing of the pipette channel. In some embodiments, for each pipette channel, the valve does not move relative to the manifold when the dispense head moves relative to the manifold. In some embodiments, each pipette channel further comprises a second valve that moves with the dispense head relative to the manifold. In some embodiments, operation of each second valve is regulated independently of any other second valve by control signals transmitted from the manifold. In some embodiments, the second valve is configured to control the aspirate and dispense operations of the dispense head. In some embodiments, the second valve is a solenoid valve. In some embodiments, the dispense head performs an aspirate operation when the valve diverts gas under vacuum to the dispense head, wherein the dispense head performs a dispense operation when the valve diverts gas under pressure to the dispense head, and wherein the second valve is configured to control a volume of a liquid aspirated and dispensed by the dispense head during aspirate and dispense operations, respectively. In some embodiments, the dispense head performs an aspirate operation when the valve diverts gas under vacuum to the dispense head, wherein the dispense head performs a dispense operation when the valve diverts gas under pressure to the dispense head, and wherein the second valve is configured to control a timing of the aspirate operation and the dispense operation. In some embodiments, each second valve is powered independently of any other second valve by the electrical signals transmitted from the manifold. In some embodiments, each pipette channel is configured to be coupled and uncoupled from the manifold independently of another pipette channel coupled to the manifold. In some embodiments, each dispense head is moveable along a vertical direction relative to the manifold independently of another dispense head coupled to the manifold. In some embodiments, each of the one or more pipette channels is modular. In some embodiments, the one or more pipette channels comprise a first pipette channel and a second pipette channel coupled to the manifold, wherein the first pipette channel is calibrated at a first setting related to volume for aspirate and dispense operations and the second pipette channel is calibrated at a second, different setting related to volume for aspirate and dispense operations. In some embodiments, the one or more pipette channels comprise a first pipette channel and a second pipette channel coupled to the manifold, wherein the first pipette channel is calibrated at a first setting related to pressure for aspirate and dispense operations and the second pipette channel is calibrated at a second, different setting related to pressure for aspirate and dispense operations. In some embodiments, the first pipette channel and the second pipette channel are calibrated before the first pipette channel and the second pipette channel are coupled to the manifold. In some embodiments, the one or more pipette channels comprise a first pipette channel and a second pipette channel, wherein the pressure port and the vacuum port of the first pipette channel have the same orientation as the pressure port and the vacuum port of the second pipette channel. In some embodiments, the first pipette channel and the second pipette channel have one or more different dimensions. In some embodiments, the first pipette channel and the second pipette channel are configured to perform different functions simultaneously. In some embodiments, the liquid dispenser has 3 pipette channels coupled to the manifold. In some embodiments, the liquid dispenser has 5 pipette channels coupled to the manifold. In some embodiments, each pipette channel comprises a pipette tip sensor configured to detect whether a pipette tip is engaged with the dispense head. In some embodiments, each pipette channel comprises a sensor configured to sense when vertical motion of the dispense head is obstructed. In some embodiments, the one or more pipette channels comprise two or more pipette channels, wherein each valve of the two or more pipette channels is configured to be individually actuated to selectively divert the gas under pressure or the gas under vacuum from the manifold to each dispense head.

A method of dispensing and aspirating a fluid is provided herein. The method includes: providing a manifold comprising a vacuum channel and a pressure channel; providing one or more pipette channels, each pipette channel comprising a dispense head, a vacuum port, a pressure port, and an independently controlled valve in simultaneous fluid communication with the vacuum port and the pressure port; selectively engaging the one or more pipette channels to the manifold, wherein selectively engaging comprises connecting each vacuum port of the one or more pipette channels to the vacuum channel of the manifold and connecting each pressure port of the one or more pipette channels to the pressure channel of the manifold; transmitting control signals from the manifold to a first pipette channel of the one or more pipette channels to independently control operation of the independently controlled valve to selectively direct gas under vacuum or gas under pressure received through the vacuum port and the pressure port of the first pipette channel to the dispense head of the first pipette channel; and performing aspirate and dispense operations with the first pipette channel, the aspirate and dispense operations comprising aspirating the fluid or dispensing the fluid in response to receipt of gas under vacuum or gas under pressure, respectively, in the dispense head of the first pipette channel from the independently controlled valve of the first pipette channel.

In some embodiments, the method includes selectively engaging the first pipette channel and a second pipette channel to the manifold; transmitting control signals from the manifold to the second pipette channel to independently control operation of the independently controlled valve to selectively direct gas under vacuum or gas under pressure received through the vacuum port and the pressure port of the second pipette channel to the dispense head of the second pipette channel; and performing aspirate and dispense operations with the second pipette channel, the aspirate and dispense operations comprising aspirating a second fluid or dispensing a second fluid in response to receipt of gas under vacuum or gas under pressure, respectively, in the dispense head of the second pipette channel from the independently controlled valve of the second pipette channel. In some embodiments, the aspirate and dispense operations of the first pipette channel and the second pipette channel occur simultaneously. In some embodiments, the aspirate and dispense operations of the first pipette channel and the second pipette channel occur independently. In some embodiments, the first pipette channel dispenses at the same time the second pipette channel aspirates. In some embodiments, the first pipette channel and the second pipette channel simultaneously aspirate a different volume of fluid. In some embodiments, the first pipette channel and the second channel simultaneously dispense a different volume of liquid. In some embodiments, the first pipette channel and the second pipette channel simultaneously aspirate a volume of fluid at different pressures. In some embodiments, the first pipette channel and the second channel simultaneously dispense a volume of fluid at different pressures. In some embodiments, the independently controlled valve of the first pipette channel diverts gas under pressure at the same time the independently controlled valve of the second pipette channel diverts gas under vacuum. In some embodiments, the independently controlled valve of the first pipette channel starts or stops the diversion of gas independently of the independently controlled valve of the second pipette channel. In some embodiments, the method includes selectively engaging the first pipette channel and a second pipette channel to the manifold, wherein the valve of the first pipette channel diverts gas under pressure to the dispense head of the first pipette channel at the same time the valve of the second pipette channel diverts gas under vacuum to the dispense head of the second pipette channel, such that the dispense head of the first pipette channel dispenses a fluid at the same time the dispense head of the second pipette channel aspirates a fluid. In some embodiments, the pressure channel comprises a plurality of pressure cross-channels and the vacuum channel comprises a plurality of vacuum cross-channels, and wherein each pipette channel is configured to connect to one pressure cross-channel and one vacuum cross-channel when the pipette channel is selectively engaged to the manifold. In some embodiments, the manifold comprises a plurality of lanes, each lane comprising one pressure cross-channel and one vacuum cross channel, and wherein selectively engaging comprises engaging one pipette channel to any one lane of the plurality of lanes. In some embodiments, the method includes, in sequence, aspirating the fluid in response to receipt of gas under vacuum in the dispense head of the first pipette channel and dispensing the fluid in response to receipt of gas under pressure in the dispense head. In some embodiments, the method includes coupling a single source of gas under pressure and a single source of gas under vacuum to the manifold. In some embodiments, the pressure channel terminates at an inlet pressure port and the vacuum channel terminates at an inlet vacuum port, wherein the manifold only accepts gas under pressure and gas under vacuum through the inlet pressure port and the inlet vacuum port, respectively. In some embodiments, the pipette channel only accepts gas under pressure and gas under vacuum through the pressure port and the vacuum port, respectively. In some embodiments, the method includes transmitting electrical signals from the manifold to the one or more pipette channels, each pipette channel powered independently of any pipette channel by the electrical signals transmitted from the manifold. In some embodiments, each of the one or more pipette channels only receives control signals and electrical signals through the electrical connection with the manifold. In some embodiments, the method includes reducing free-fall of the dispense head in the event of loss of electrical signals via a magnetic brake. In some embodiments, selectively engaging the first pipette channel with the manifold comprises aligning one or more pegs of the pipette channel with one or more openings of the manifold. In some embodiments, selectively engaging the first pipette channel with the manifold comprises tightening one or more captive screws of the pipette channel. In some embodiments, selectively engaging the first pipette channel with the manifold comprises compressing a seal between the first pipette channel and the manifold. In some embodiments, the seal is a captive o-ring of the pipette channel. In some embodiments, the method includes selectively directing gas under pressure and gas under vacuum received through the pressure port and the vacuum port of the first pipette channel to the dispense head of the first pipette channel via a tube. In some embodiments, the tube is the only pneumatic connection between the valve and the dispense head. In some embodiments, the tube is configured to bend as the dispense head moves vertically. In some embodiments, the fluid comprises a liquid. In some embodiments, the fluid comprises a gas.

A liquid dispenser described herein includes a manifold comprising a vacuum channel, a pressure channel, and a plurality of lanes, each lane comprising an electrical connector, a port to the pressure channel, and a port to the vacuum channel; and one or more pipette channels, each pipette channel comprising a single dispense head and configured to couple to the electrical connector, the pressure port, and the vacuum port of any one lane of the plurality of lanes.

In some embodiments, each pipette channel comprises a valve configured to selectively distribute gas under pressure and gas under vacuum from the pressure port and the vacuum port, respectively, to the single dispense head. In some embodiments, each of the one or more pipette channels are coupled to one lane of the plurality of lanes, and wherein, for each pipette channel, operation of the valve is independently controlled by signals transmitted to the valve via the electrical connector of the one lane to which the pipette channel is coupled. In some embodiments, each pipette channel comprises a first portion that does not move relative to the manifold when the pipette channel is coupled to the manifold and a second portion that moves relative to the manifold when the pipette channel is coupled to the manifold. In some embodiments, the valve is enclosed within the first portion, the dispense head is coupled to the second portion, and a tube connecting the valve and the dispense head is configured to move within the first portion when the second portion moves relative to the first portion. In some embodiments, each pipette channel comprises an electrical connector, a pressure port, and a vacuum port. In some embodiments, the electrical connector, the pressure port, and the vacuum port of any pipette channel is configured to couple to the electrical connector, the pressure port, and the vacuum port, respectively, of any one lane of the plurality of lanes. In some embodiments, the electrical connector, the pressure port, and the vacuum port of the one or more pipette channels do not move relative to the manifold when the electrical connector, the pressure port, and the vacuum port of the one or more pipettes channels are coupled to the manifold. In some embodiments, the single dispense head of the one or more pipette channels moves relative to the manifold when the one or more pipettes channels are coupled to the manifold. In some embodiments, the liquid dispenser includes a plurality of pipette channels, wherein each lane of the plurality of lanes is configured to couple to any one pipette channel of the plurality of pipette channels. In some embodiments, the pressure channel and the vacuum channel are physically and fluidically isolated from each other within the manifold. In some embodiments, the manifold comprises a single pressure channel and a single vacuum channel. In some embodiments, each pipette channel is configured to selectively couple and uncouple to the electrical connector, the pressure port, and the vacuum port of any one lane of the plurality of lanes. In some embodiments, a longitudinal axis of each lane of the plurality of lanes is oriented transverse to the pressure channel. In some embodiments, a longitudinal axis of each lane of the plurality of lanes is oriented transverse to the vacuum channel. In some embodiments, the one or more pipette channels comprise a plurality of pipette channels, wherein at least one pipette channel of the plurality of pipette channels is coupled to one lane of the plurality of lanes, and wherein at least one lane of the plurality of lanes is not coupled to a pipette channel of the plurality of pipette channels. In some embodiments, the liquid dispenser includes a cover configured to seal the pressure port and the vacuum port of the at least one lane that is not coupled to a pipette channel of the plurality of pipette channels. In some embodiments, the liquid dispenser includes only one pipette channel, wherein the pipette channel is coupled to one lane of the plurality of lanes, and wherein each of the remaining lanes of the plurality of lanes is not coupled to a pipette channel. In some embodiments, each lane comprises a single port to the pressure channel and a single port to the vacuum channel. In some embodiments, the liquid dispenser includes a first pipette channel coupled to a first lane of the plurality of lanes and a second pipette channel coupled to a second lane of the plurality of lanes, wherein the single dispense head of the first pipette channel aspirates a fluid at the same time the single dispense head of the second pipette channel dispenses a fluid. In some embodiments, the one or more pipette channels comprises two pipette channels with different calibration settings related to pressure of gas in the dispense head during aspirate and dispense operations. In some embodiments, the one or more pipette channels comprises two pipette channels with different calibration settings related to volume of fluid aspirated and dispensed during aspirate and dispense operations. In some embodiments, the one or more pipette channels comprises two pipette channels with different calibration settings related to speed of aspirate and dispense operations. In some embodiments, the one or more pipette channels comprise a plurality of pipette channels, wherein at least two of the plurality of pipette channels are identical. In some embodiments, the one or more pipette channels comprise a plurality of pipette channels, wherein at least two of the plurality of pipette channels are different. In some embodiments, the at least two different pipette channels have one or more different dimensions. In some embodiments, each pipette channel comprises a valve operable to control the flow of gas within each pipette channel. In some embodiments, each pipette channel comprises a valve operable to control the aspirate and dispense operations of the single dispense head of the pipette channel. In some embodiments, each of the one or more pipette channels are selectively and independently coupled to the manifold. In some embodiments, the pressure channel comprises a first end and a second end terminating at an inlet pressure port, wherein the inlet pressure port is connected to an external source of gas under pressure, wherein the vacuum channel comprises a first end and a second end terminating at an inlet vacuum port, and wherein the inlet vacuum port is connected to an external source of gas under vacuum. In some embodiments, the manifold only accepts gas under pressure and gas under vacuum through the inlet pressure port and the inlet vacuum port, respectively. In some embodiments, the electrical connector of each lane of the plurality of lanes is configured to transmit electrical signals from the manifold to one pipette channel, and wherein each pipette channel is configured, when coupled to the manifold, to be powered independently of any other pipette channel coupled to the manifold by the electrical signals transmitted from the manifold. In some embodiments, each of the one or more pipette channels is coupled to the manifold, and wherein each of the one or more pipette channels only receives control signals and electrical signals through the electrical connector of the lane to which the respective pipette channel is coupled. In some embodiments, at least one pipette channel further comprises a magnetic brake. In some embodiments, the magnetic brake of the at least one pipette channel is configured to reduce free-fall of the single dispense head of the at least one pipette channel in the event of loss of electrical signals. In some embodiments, at least one pipette channel further comprises a ball screw configured to move the single dispense head of the at least one pipette channel in a vertical direction relative to the manifold. In some embodiments, the at least one pipette channel further comprises a coupling configured to reduce misalignment of the ball screw. In some embodiments, the liquid dispenser includes a plurality of pipette channels coupled to the manifold, and the pressure channel provides gas under pressure to all pipette channels coupled to the manifold at the same pressure. In some embodiments, the liquid dispenser includes a plurality of pipette channels coupled to the manifold, and the vacuum channel provides gas under vacuum to all pipette channels coupled to the manifold at the same pressure. In some embodiments, the liquid dispenser includes a plurality of pipette channels coupled to the manifold, and the manifold is operable to provide gas under pressure to a first set of pipette channels at a first pressure and to simultaneously provide gas to a second, different set of pipette channels at a second, different pressure. In some embodiments, each pipette channel is configured to be selectively mounted to the manifold with two screws. In some embodiments, the two screws are captive to the pipette channel. In some embodiments, at least one pipette channel comprises one or more pegs configured to align with one or more openings of the manifold. In some embodiments, the one or more pegs engage the one or more openings of the manifold before an electrical connector engages the pipette channel. In some embodiments, each pipette channel comprises one or more o-rings configured to provide a seal between each pipette channel and the manifold. In some embodiments, the one or more o-rings are captured in a dove-tail groove in each pipette channel. In some embodiments, the one or more pipette channels comprises a first pipette channel and a second pipette channel coupled to the manifold. In some embodiments, the first pipette channel comprises a different calibration setting for dispensing than the second pipette channel. In some embodiments, the first pipette channel and the second pipette channel have different dispense heads. In some embodiments, the liquid dispenser includes a blanking plate configured to close one port to the pressure channel and one port to the vacuum channel of the manifold. In some embodiments, each pipette channel comprises a valve configured to selectively distribute gas under vacuum and gas under pressure from the vacuum port and the pressure port, respectively, to the single dispense head, wherein each pipette channel further comprises a tube, the tube having a first end terminating at the valve and a second end terminating at the dispense head, and wherein the tube is configured to divert gas from the valve to the dispense head. In some embodiments, the tube is the only pneumatic connection between the valve and the dispense head. In some embodiments, the tube is configured to bend as the dispense head moves vertically relative to the manifold when the pipette channel is coupled to the manifold. In some embodiments, the valve does not move vertically relative to the manifold when the pipette channel is coupled to the manifold, and wherein the tube is configured to bend within a housing of the pipette channel when the dispense head moves vertically relative to the manifold. In some embodiments, the tube and the valve are enclosed within a first housing of the pipette channel and the dispense head is coupled to a second housing of the pipette channel enclosing a second valve. In some embodiments, the tube is enclosed within an outer housing of the pipette channel. In some embodiments, each pipette channel comprises a valve configured to selectively distribute gas under vacuum and gas under pressure from the vacuum port and the pressure port, respectively, to the single dispense head, and wherein each pipette channel further comprises a second valve that is configured to move with the dispense head when the pipette channel is coupled to the manifold. In some embodiments, operation of each second valve is regulated independently of any other second valve by control signals transmitted from the manifold. In some embodiments, the second valve is configured to control the aspirate and dispense operations of the dispense head. In some embodiments, the second valve is a solenoid valve. In some embodiments, the second valve is configured to control the amount of liquid aspirated or dispensed by the dispense head. In some embodiments, the second valve is configured to control the timing of liquid aspirated or dispensed by the dispense head. In some embodiments, each second valve is powered independently of any second valve by the electrical signals transmitted from the manifold. In some embodiments, each pipette channel comprises a valve configured to selectively distribute gas under pressure and gas under vacuum from the pressure port and the vacuum port, respectively, to the single dispense head, and wherein each valve is a three way solenoid valve. In some embodiments, each pipette channel is configured to be coupled and uncoupled from the manifold independently of another pipette channel coupled to the manifold. In some embodiments, the one or more pipette channels comprises a plurality of pipette channels coupled to the manifold, wherein each dispense head of the plurality of pipette channels is moveable along a vertical direction relative to the manifold independently of another dispense head coupled to the manifold. In some embodiments, the one or more pipette channels are modular. In some embodiments, the one or more pipette channels comprises a plurality of identical pipette channels. In some embodiments, the one or more pipette channels comprises a first pipette channel and a second pipette channel coupled to the manifold, wherein the first pipette channel and the second pipette channel are calibrated to aspirate and dispense a volume of liquid, and wherein the first pipette channel comprises a volume calibration setting that is different than the volume calibration setting of the second pipette channel. In some embodiments, the one or more pipette channel comprises a first pipette channel and a second pipette channel coupled to the manifold, wherein the first pipette channel and the second pipette channel are calibrated to aspirate and dispense a liquid at a pressure, and wherein the first pipette channel comprises a pressure calibration setting that is different than the pressure calibration setting of the second pipette channel. In some embodiments, the one or more pipette channel comprises a first pipette channel and a second pipette channel each comprising a pressure port and a vacuum port, and wherein the pressure port and the vacuum port of the first pipette channel have the same orientation of as the pressure port and the vacuum port of the second pipette channel. In some embodiments, the first pipette channel and the second pipette channel have one or more different dimensions. In some embodiments, the first pipette channel and the second pipette channel perform different functions simultaneously. In some embodiments, the liquid dispenser has 3 pipette channels coupled to the manifold. In some embodiments, the liquid dispenser has 5 pipette channels coupled to the manifold. In some embodiments, each dispense head is independently movable in a vertical direction relative to the manifold when the dispense head is coupled to the manifold via its respective pipette channel. In some embodiments, each pipette channel comprises a pipette tip sensor configured to detect whether a pipette tip is engaged with the dispense head. In some embodiments, each pipette channel comprises a sensor configured to sense when vertical motion of the dispense head is obstructed. In some embodiments, the liquid dispenser includes two or more pipette channels coupled to the manifold, wherein each valve of the two or more pipette channels is configured to be individually actuated to selectively divert gas under vacuum or gas under pressure from the manifold to each dispense head.

A system described herein includes a manifold comprising a pressure channel, a vacuum channel, one pressure sub-channel beginning at the pressure channel and terminating at an external surface of the manifold, one vacuum sub-channel beginning at the vacuum channel and terminating at the external surface of the manifold. The system includes one pipette channel coupled to the manifold, the pipette channel comprising a single dispense head, a pressure port configured to receive gas under pressure from the pressure sub-channel of the manifold, a vacuum port configured to receive gas under vacuum from the vacuum sub-channel of the manifold, and a valve in simultaneous fluid communication with the pressure port and the vacuum port, the valve operable to selectively divert gas under pressure and gas under vacuum to the dispense head. The system includes electrical connections configured to transmit control signals from the manifold to the pipette channel, operation of the valve regulated exclusively by the control signals transmitted from the manifold.

In some embodiments, the system includes a second pipette channel that is not coupled to the manifold, wherein the second pipette channel is identical to the pipette channel coupled to the manifold. In some embodiments, the system includes a second pipette channel that is not coupled to the manifold, wherein the second pipette channel is different than the pipette channel coupled to the manifold.

BRIEF DESCRIPTION OF THE DRAWINGS

FIGS. 1B-4 show views of a liquid dispenser according to a second embodiment.

FIGS. 61-64 show views of the fourth embodiment.

DETAILED DESCRIPTION

Any feature or combination of features described herein are included within the scope of the present disclosure provided that the features included in any such combination are not mutually inconsistent as will be apparent from the context, this description, and the knowledge of one skilled in the art. In addition, any feature or combination of features may be specifically excluded from any embodiment of the present disclosure. For purposes of summarizing the present disclosure, certain aspects, advantages, and novel features of the present disclosure are described herein. Of course, it is to be understood that not necessarily all such aspects, advantages, or features will be present in any particular embodiment of the present disclosure.

It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the present disclosure.

Figure 1A:
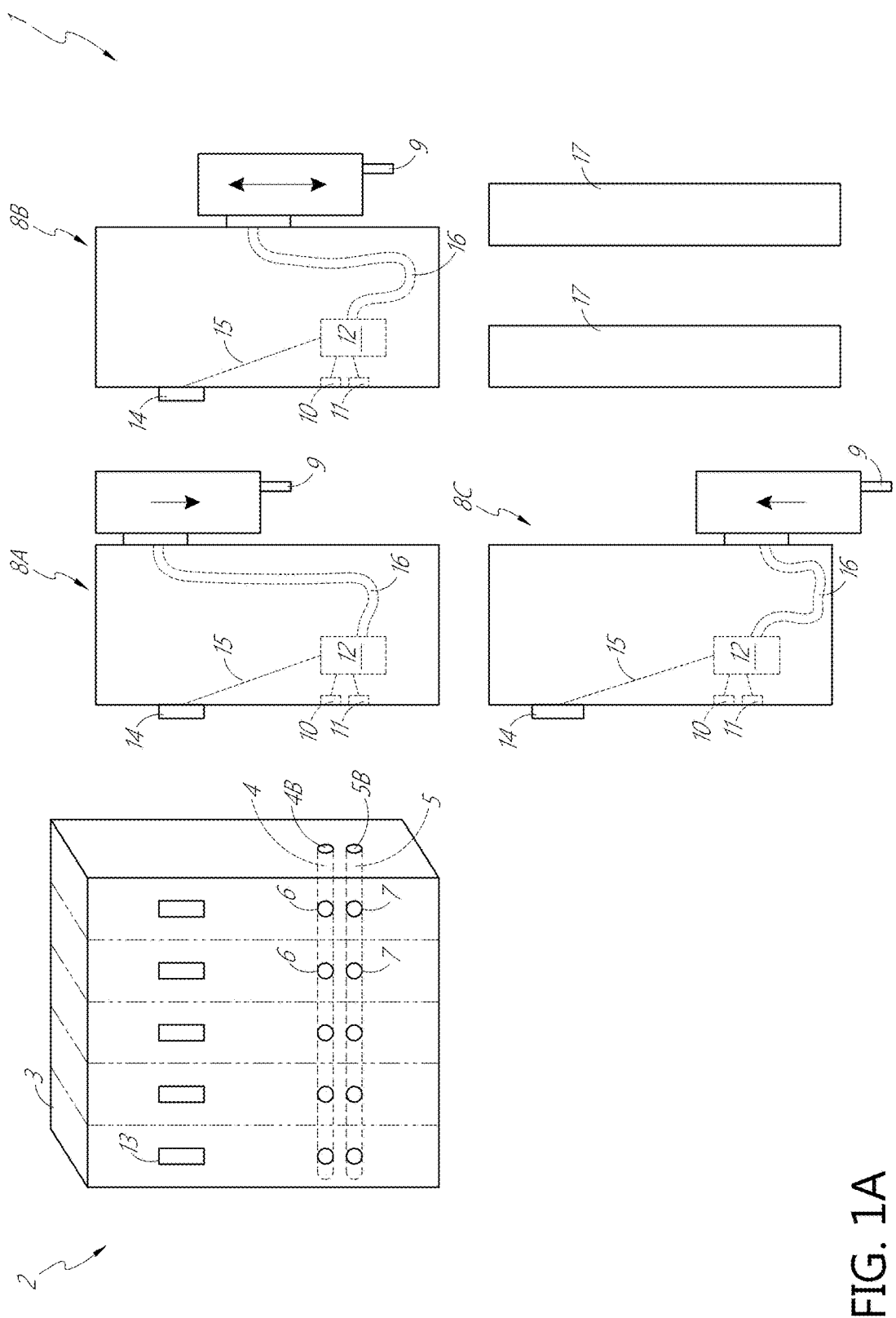
FIG. 1A shows a schematic figure of an embodiment of a liquid dispenser according to a first embodiment.
Figure 1B:
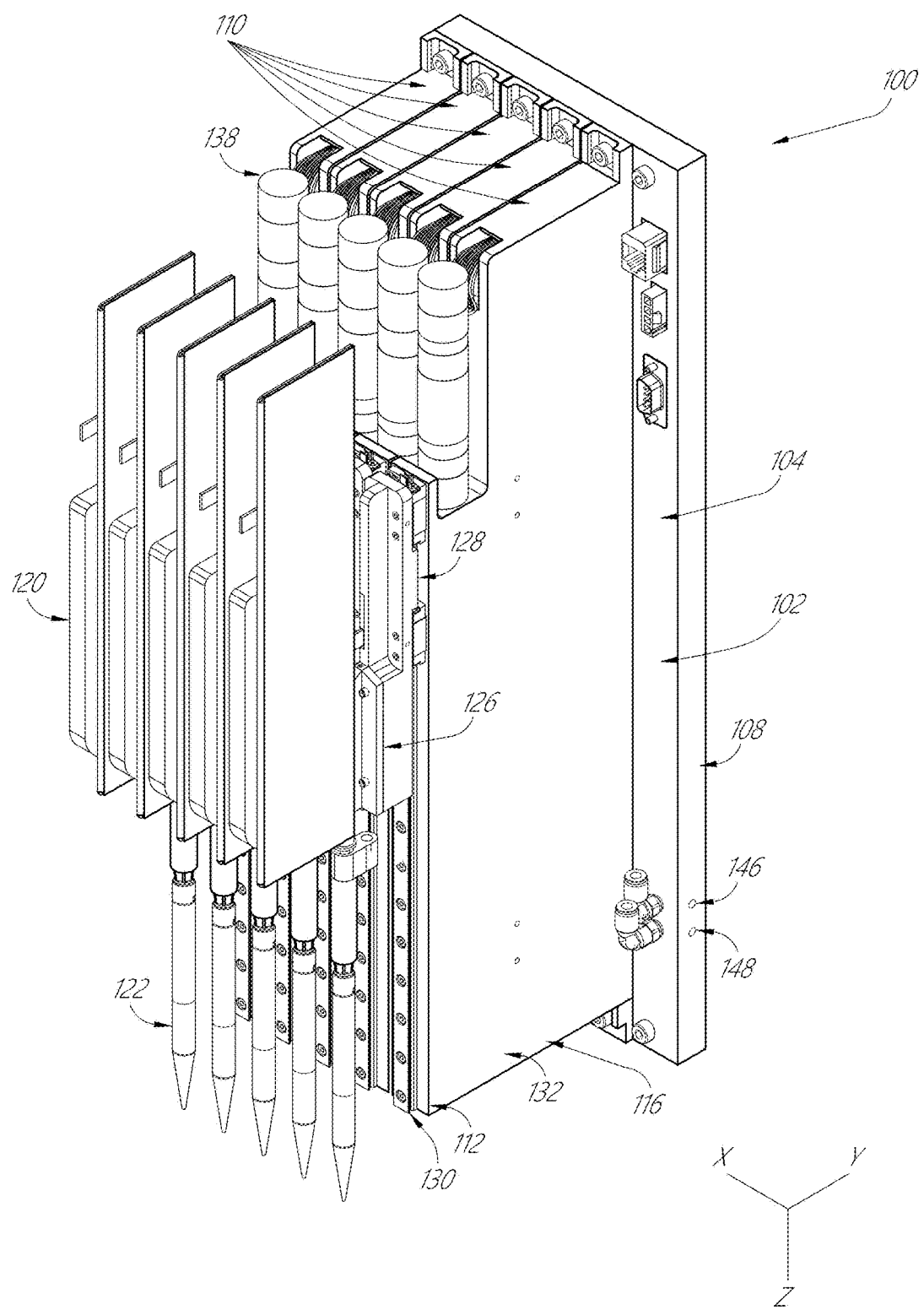

FIG. 1A is a schematic figure of an embodiment of a liquid dispenser 1 according to embodiments of the present disclosure. FIG. 1A is a schematic figure, not drawn to scale. The liquid dispenser 1 includes a manifold 2 having a pressure channel 4 to deliver gas under pressure and a vacuum channel 5 to deliver gas under vacuum. The manifold 2 includes a plurality of pressure cross-channels 6, each pressure cross-channel 6 beginning at the pressure channel 4 and terminating at an external surface of the manifold 2 as shown in FIG. 1A. The manifold 2 includes a plurality of vacuum cross-channels 7, each vacuum cross-channel 7 beginning at the vacuum channel 5 and terminating at the external surface of the manifold 2 as shown in FIG. 1A. The pressure channel 4 comprises a first end and a second end terminating at an inlet pressure port 4B. The inlet pressure port is connected to an external source of gas under pressure. The vacuum channel 5 comprises a first end and a second end terminating at an inlet vacuum port 5B. The inlet vacuum port is connected to an external source of gas under vacuum. The pressure channel 4 and the vacuum channel 5B are physically and fluidically isolated from each other within the manifold 2. In some implementations described herein, the end of a pressure cross-channel 6 terminating at the external surface of the manifold 2 is referred to as a port to the pressure channel 4 and the end of a vacuum cross-channel 7 terminating at the external surface of the manifold 2 is referred to as a port to the vacuum channel 5.

The liquid dispenser 1 includes one or more pipette channels. In the illustrated embodiment, the liquid dispenser includes three pipette channels, pipette channels 8A, 8B, 8C. Each pipette channel is designed to selectively couple to and selectively uncouple from the manifold 2. FIG. 1A illustrates the pipette channels 8A, 8B, 8C before they have been selectively coupled to the manifold 2, or after they have been selectively uncoupled from the manifold 2. Any one pipette channel 8A, 8B, and 8C can be selectively coupled and uncoupled to one lane 3 of the manifold 2, independent of the state of any other pipette channel. Each pipette channel 8A, 8B, 8C includes a dispense head 9 designed to perform dispense and aspirate operations. Each pipette channel 8A, 8B, 8C includes a pressure port 10 designed to receive gas under pressure from one pressure cross-channel 6. Each pipette channel 8A, 8B, 8C includes a vacuum port 11 designed to receive gas under vacuum from one vacuum cross-channel 7. Each pipette channel 8A, 8B, 8C includes a valve 12 in simultaneous fluid communication with the pressure port 10 and the vacuum port 11. The valve 12 is operable to selectively divert gas under pressure and gas under vacuum to the dispense head 9. The valve 12 is designed to direct gas under pressure to the dispense head. The valve 12 is designed to distribute gas under vacuum to the dispense head 9. The valve 12 is designed to divert either gas under pressure or gas under vacuum to the dispense head 9, while being simultaneously supplied with gas under pressure and gas under vacuum by the manifold 2. For each pipette channel 8A, 8B, 8C, the dispense head 9 is coupled to a pipette tip (not shown). The dispense head 9 is designed to dispense a liquid from the pipette tip when the valve 12 diverts gas under pressure to the dispense head 9. The dispense head 9 is designed to aspirate a liquid into the pipette tip when the valve 12 diverts gas under vacuum to the dispense head 9.

The liquid dispenser 1 includes an electrical connector 13 on the manifold 2 designed to transmit control signals from the manifold 2 to the pipette channels 8A, 8B, 8C. The operation of each valve 12 is regulated independently of any other valve 12 by the control signals transmitted from the manifold 2. Each independently controllable valve 12 is housed in a pipette channel. The independently controllable valves 12 selectively divert gas under pressure and gas under vacuum based, at least in part on, the control signals. Each independently controllable valve 12 has simultaneous access to the pressure channel 4 and the vacuum channel 5B when the respective pipette channel (pipette channel 8A, 8B, or 8C) with the independently controllable valve 12 is coupled to the manifold 2.

As explained above, each of the pipette channels 8A, 8B, 8C are selectively and independently coupled to the manifold 2. In some embodiments, the manifold 2 comprises a plurality of lanes 3, each lane 3 comprising one pressure cross-channel 6 and one vacuum cross channel 7. Each lane comprises an electrical connector 13. During installation, each pipette channel 8A, 8B, 8C is selective engaged to a lane of the plurality of lanes 3. In some embodiments, each pipette channel 8A, 8B, 8C is selectively engaged to any one lane of the plurality of lanes 3. Each pipette channel 8A, 8B, 8C comprises a single dispense head 9. In some embodiments, each lane 3 can be defined by one or more of the following features: a single pressure cross-channel 6, a single vacuum cross-channel 7, an electrical connector 13, a single pipette channel 8A, 8B, 8C, a single dispense head 9 coupled thereto, etc.

FIG. 1A shows a cross-sectional view of the pipette channels 8A, 8B, 8C. Each pipette channel 8A, 8B, 8C includes a corresponding electrical connector 14. In addition to the control signals, the electrical connectors 13, 14 are further designed to transmit electrical signals from the manifold 2 to the pipette channels 8A, 8B, 8C. Each pipette channel 8A, 8B, 8C is powered independently of any other pipette channel 8A, 8B, 8C by the electrical signals transmitted from the manifold 2. In some embodiments, each pipette channel 8A, 8B, 8C includes a cable 15 transmitting control signals and electrical signals from the electrical connector 14 to one or more components of the pipette channel 8A, 8B, 8C. In the illustrated embodiment, the cable 15 transmits control signals and electrical signals from the electrical connector 14 to the valve 12. The cable 15 can continue from the valve 12 to the dispense head 9, or another cable can be used to connect the electrical connector 14 to the dispense head 9. Other configurations are contemplated. There are many signals that can be transmitted through the electrical connector 14 of the pipette channels 8A, 8B, 8C. The valve 12 can be controlled by control signals, but other components can be controlled as well. In some embodiments, the electrical connector 14 is considered a backplane connector. The electrical connector 14 can be integral to the circuit board of the pipette channels 8A, 8B, 8C. The valve 12 can connect to the circuit board such as through one or more cables. The pipette channels 8A, 8B, 8C can include cables that connect the circuit board to another circuit board above the dispense head 9. The dispense head 9 is then connected via another set of cables to this second circuit board. The liquid dispenser 1 can include any number of cables and circuit boards needed to perform the functions described herein.

Each pipette channel 8A, 8B, 8C comprises a tube 16. The tube 16 has a first end terminating at the valve 12 and a second end terminating at the dispense head 9. The tube 16 is designed to direct gas from the valve 12 to the dispense head 9. In some embodiments, the tube 16 tube is the only pneumatic connection between the valve 12 and the dispense head 9. The tube 16 is completely enclosed inside an outer housing of the pipette channel 8A, 8B, 8C. As shown in FIG. 1A, the tube 16 is designed to bend as the dispense head 9 moves vertically. The dispense head 9 is shown in different vertical positions to illustrate the independent vertical motion of the dispense head 9 relative to a portion of the pipette channel 8A, 8B, 8C that is engaged to a lane 3. The tube 16 bends as needed within the pipette channel 8A, 8B, 8C as the dispense head 9 travels up and down.

In some cases, such as that shown in FIG. 1A, there are more lanes 3 on the manifold 2 than there are pipette channels. The system 1 can include one or more blanking plates, such as blanking plates 17, configured to seal portions of the manifold 2 that are not coupled to a pipette channel. For example, one blanking plate 17 can be configured to couple to one lane 3 of the manifold 2 and seal one pressure cross-channel 6 and one vacuum cross-channel 7 of the lane 3 to which the blanking plate 17 is coupled. The system 1 includes two blanking plates 17, each configured to seal a pressure cross-channel 6 and a vacuum cross-channel 7 of one lane 3. When each of the three pipette channels 8A, 8B, and 8C and each of the two blanking plates 17 are coupled to one lane 3 of the manifold 2, each of the pressure cross-channels 6 and each of the vacuum cross-channels 7 are sealed to the ambient environment. Only the inlet pressure port 4B and the inlet vacuum port 5B are open to the ambient environment. As explained above, an external source of gas under pressure can be coupled to the manifold 2 at the inlet pressure port 4B and an external source of gas under vacuum can be coupled to the manifold 2 at the inlet vacuum port 5B. In some cases, the system 1 can include a blanking plate (not shown) configured to seal pressure cross-channels and vacuum cross-channels of more than one lane.

Embodiments of the valve 12 described herein can include three way solenoid valve. The valve 12 can include very few parts, with few wear points. One non-limiting example valve 12 is a Bullet Valve® by Mac® (part number BV309A-CC1-00 or VC309A-CD1-00). The valve 12 can be implemented as a 3 Way Normally Closed or a 3 Way Universal valve. Operational benefits of the valve 12 include one or more of the following: a shorter stroke with high shifting forces, balanced poppet, and precise reliability. The valve 12 can be mounted without fasteners. The valve 12 can be immune to pressure fluctuations. The solenoid can be isolated from contaminated air. The valve 12 can be supplied with 12 VDC or 24 VDC voltage, The valve 12 can operate on various fluids, including compressed air, vacuum and/or inert gases. The pressure range can be from vacuum to 120 PSI. The valve 12 can operate as a selector valve where gas under pressure comes into the #3 port and gas under vacuum comes into the #1 port. Although embodiments of the valve 12 are described herein in the context of a three way solenoid valve, other types of valves may be implemented.

FIGS. 1B-4 show views of a liquid dispenser 100 according to one embodiment of the present disclosure. Liquid dispenser 100 comprises a manifold 102 that has a front 104, a back 106, and sides 108. The manifold 102 is configured to accept one or more pipette channels 110, where each pipette channel 110 houses various components used in aspirate and dispense operations. The pipette channel 110 has a front 112, a back 114, and sides 116.

The liquid dispenser 100 is modular, thereby enabling flexibility and versatility in arranging the one or more pipette channels 110 relative to the manifold 102. In the embodiment shown, the front 112 of the pipette channels 110 includes a pipette module 120. The pipette module 120 includes pipetting mechanisms that use air under vacuum and pressurized air to aspirate and dispense fluid from a pipette tip 122. One non-limiting example pipette tip 120 is the Air Driven OEM Channel Pipettor by Seyonic® (part number PCNC-0061-00). Pipette tips 122 can be disposable. Each pipette module 120 can include a tip adapter 118, wherein each tip adapter 118 is configured to accept a pipette tip 122. A pipette tip 122 can be attached to the tip adapter 118, for instance, by Z-direction movement of the pipette module 120 relative to a pipette tip 122. A pipette tip 122 can be removed from the tip adapter 118, for instance, by movement of the pipette module 120 relative to a pipette stripper (not shown). The liquid dispenser 100 can include independent pipette tip 122 attachment or removal. The back 114 of the pipette channel 110 is configured to reversibly connect to, or mate with, the front 104 of the manifold 102, as described herein.

The manifold 102 in this embodiment is configured to accept as many as five pipette channels 110. The manifold 102 can accept fewer than five pipette channels, such as one, two, three, or four pipette channels, and is thus advantageously customizable by an operator based on the particular liquid dispensing requirements of the operator. Although the liquid dispenser 100 shown in FIG. 1 has capacity to accept a maximum of five pipette channels 110, other configurations are contemplated. The liquid dispenser 100 can be configured to accept a maximum of one pipette channel, two pipette channels, three pipette channels, four pipette channels, five pipette channels, six pipette channels, seven pipette channels, eight pipette channels, nine pipette channels, ten pipette channels, eleven pipette channels, twelve pipette channels, thirteen pipette channels, fourteen pipette channels, fifteen pipette channels, sixteen pipette channels, seventeen pipette channels, eighteen pipette channels, nineteen pipette channels, twenty pipette channels, etc. One or more pipette channels 110 can be removed from the manifold 104. In some embodiments, one pipette channel 110 can be removed without removing another pipette channel 110. For instance, one pipette channel 110 may be removed and replaced without removing another pipette channel 110 from the manifold 102.

The mating configuration between the pipette channels 110 and the manifold 102 can have any configuration known in the art. In the non-limiting embodiment shown in FIGS. 1B-4, the liquid dispenser 100 includes one or more pegs (not visible in this view). In the illustrated embodiment, each pipette channel 110 has a peg near the top of the pipette channel 110 and a peg near the bottom of the pipette channel 110. The pegs can guide alignment between the back 114 of the pipette channel 110 and the front 104 of the manifold 102. The pegs can be dowel pins. The manifold 102 can include a corresponding slot (not shown) to accept each of the pegs. The slots can include a chamfered edge to facilitate insertion of the pegs. In some embodiments, the manifold 102 can include at least one marking (not shown) to facilitate the alignment of an edge of the pipette channel 110 with the manifold 102. In some embodiments, the manifold 102 has at least one edge (e.g., top edge, bottom edge, etc.) that aligns with a corresponding edge of the pipette channel (e.g., top edge, bottom edge, etc.).

The pipette channel 110 can include one or more fasteners 124. In some embodiments, the fasteners 124 are captive screws. In the illustrated embodiment, each pipette channel 110 has a fastener 124 near the top of the pipette channel 110 and a fastener 124 near the bottom of the pipette channel 110. In some embodiments, the fasteners 124 can be located near the pegs. In some embodiments, the fasteners 124 are threaded such that the operator can securely fasten the pipette channel 110 to the manifold 102. In some implementations, the fasteners 124 and pegs securing a pipette channel 110 to the manifold 102 are readily adjustable and/or removable by an operator without affecting the operation or connections of another pipette channel 110 that is mated with the manifold 102. In one example, a first pipette channel 110 that is malfunctioning, requires an adjustment, or is need of regular maintenance or testing can be removed by an operator without affecting the operation or connections of any other pipette channel 110 that is mated with the manifold 102. In some cases, the operator seamlessly replaces the first (now removed) pipette channel 110 with a second pipette channel by connecting the second pipette channel to the manifold 102 with pegs in the location previously occupied by the first (now removed) pipette channel 110.

The pipette channel 110 can be fixed in position to the manifold 102. The manifold 102 can be coupled to a robotic arm (not shown) which can move the manifold 102 in space. The motion of the robotic arm can have six degrees of freedom. For example, the robotic arm can include 1 degree of translational freedom, 2 degrees of translational freedom, 3 degrees of translational freedom, 1 degree of rotational freedom, 2 degrees of rotational freedom, 3 degrees of rotational freedom, or any combination of these. In some embodiments, the manifold 102 is coupled to a gantry (not shown) of an automated sample analysis system. The gantry can include a bar or rail which allows movement of the manifold 102 along an X-axis of the automated sample analysis system ("the X-direction"). The gantry can include a bar or rail which allows movement of the manifold 102 along a Y-axis of the automated sample analysis system ("the Y-direction"). Such relative motion can be accomplished by any suitable mechanical movement device, such as but not limited to, gearing, or a rack and pinion assembly, or a lead screw, or a belt drive, or a linear motor. In some embodiments, the manifold 102 is moveable along a Z-axis of the automated sample analysis system ("the Z-direction"). In other embodiments, movement of the manifold 102 in the Z-direction is prevented.

In some embodiments, movement in the Z-direction is provided by the pipette channel 110. The module 120 can include a flange 126. The flange 126 can be fixedly attached to a coupling 128. The coupling 128 is movable along a track 130. The movement of the coupling 128 causes movement of the module 120 in the Z-direction relative to the track 130. The track 130 is fixedly attached to a base 132 of the pipette channel 110. The base 132 of the pipette channel is stationary relative to manifold 102. The movement of the coupling 128 causes movement of the module 120 in the Z-direction relative to the base 132 of the pipette channel 110. The movement of the coupling 128 causes movement of the module 120 in the Z-direction relative to the manifold 102.

Figure 2:
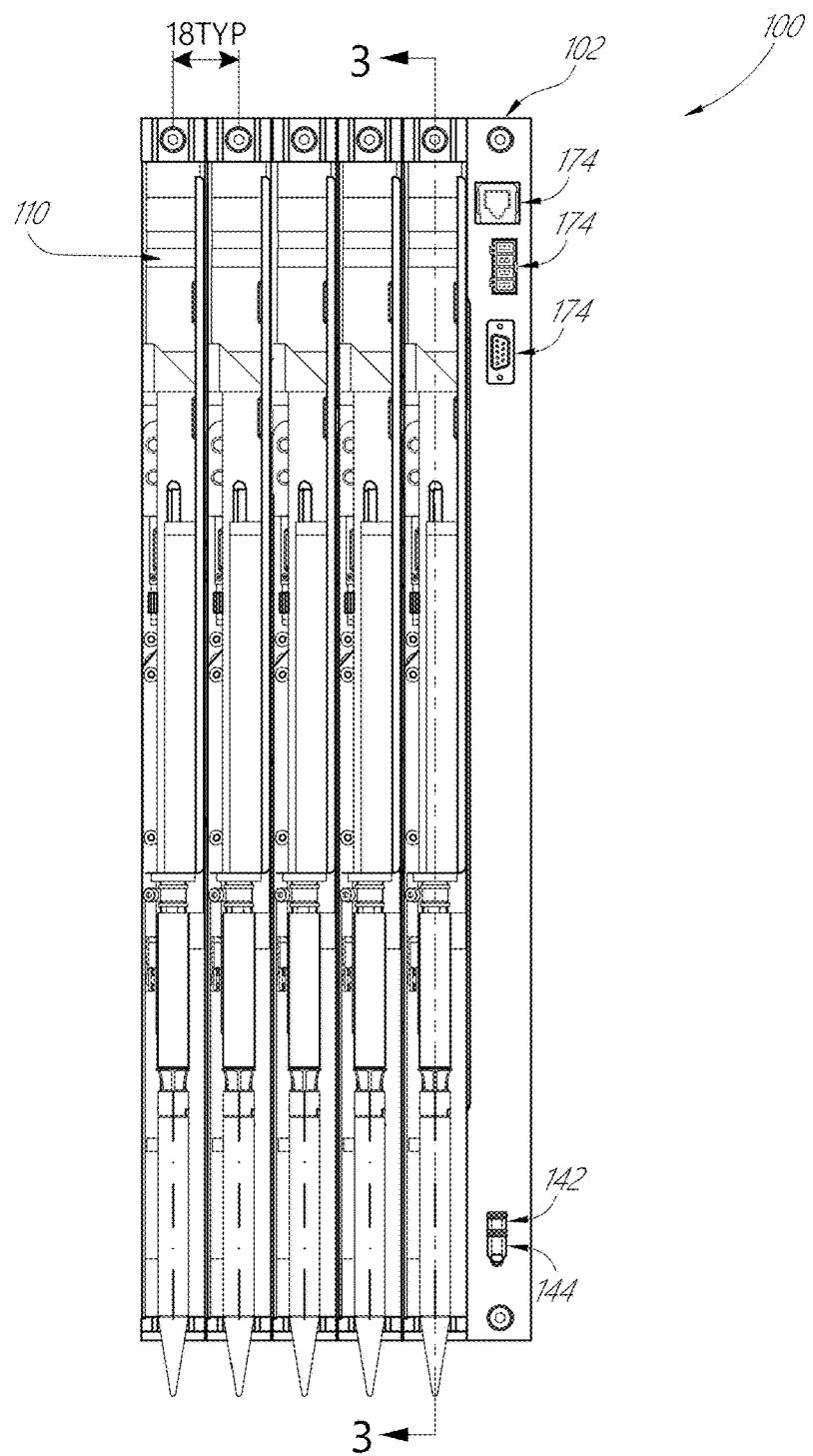
Figure 3:
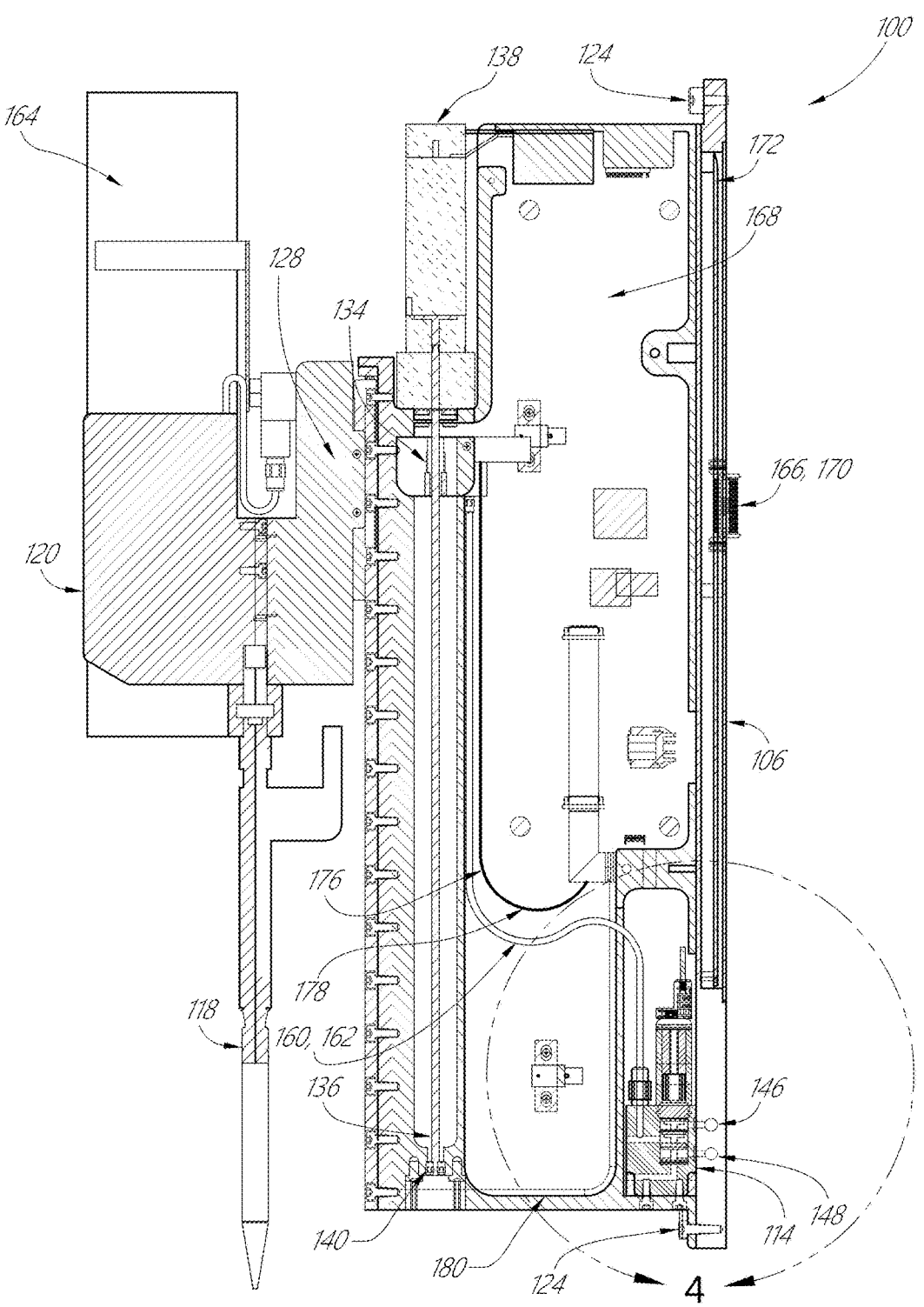

FIG. 3 shows a cross-sectional view of the liquid dispenser 100 taken along line 3-3 of FIG. 2. In some embodiments, the coupling 128 can couple to a nut 134 which includes a bore. A plurality of ball bearings are arranged around the bore inside the nut 134, which reduce friction when interacting with the ball screw 136. In some embodiments, the coupling 128 can be integral with the nut 134 configured to interact with a ball screw 136. In other embodiments, the bore 134 is threaded and interacts with a lead screw (not shown). The ball screw 136 can be rotated with a motor 138. The ball screw 136 can be coupled to a bearing 140. The bearing 140 allows the ball screw 136 to rotate without translation. As the ball screw 136 is rotated (in this embodiment, by the motor 138), the coupling 128 translates along the ball screw 136. The coupling 128 is guided along the track 130 in the Z-direction. Rotation of the ball screw 136 in a first direction causes the coupling 128 to translate downward along the track 130. Rotation of the ball screw 136 in a second, opposite direction causes the coupling 128 to translate upward along the track 130.

The module 120 includes a mechanism to provide aspirate and dispense operations. In some embodiments, a sample is only introduced into the system via the pipette tip 122. The movement of the coupling 128 allows the pipette tip 122 to be lowered into a container to aspirate and/or dispense a sample or other liquid. After aspirating or dispensing the sample or other liquid in the container, the movement of the coupling 128 allows the pipette tip 122 to be raised above the a container to move the pipette tip 122 to another location, for example over a second container in an automated sample analysis system.

The aspirate and dispense operations of the module 120 can be controlled, in part, by application of air pressure or vacuum. The manifold 102 can include an inlet pressure port 142. The manifold 102 can include an inlet vacuum port 144. The inlet pressure port 142 can be located on the front 104, back 106, or sides 108 of the manifold 102. The inlet vacuum port 144 can be located on the front 104, back 106, or sides 108 of the manifold 102. The inlet pressure port 142 and the inlet vacuum port 144 are located on the front 104 of the manifold 102 in the embodiment of FIGS. 1B-4, but other configurations are contemplated.

The manifold 102 includes a pressure channel 146 and a vacuum channel 148. The pressure channel 146 is in fluid communication with the inlet pressure port 142. In some embodiments, the inlet pressure port 142 provides the only entrance to the pressure channel 146. The pressure channel 146 exits to one or more pressure cross-channels 150 described herein. The inlet pressure 142 can, in some cases, seal the pressure channel 146. The vacuum channel 148 is in fluid communication with the inlet vacuum port 144. In some embodiments, the inlet vacuum port 144 provides the only entrance to the vacuum channel 148. The vacuum channel 148 exits to one or more vacuum cross-channels 152 described herein. The inlet vacuum port 144 can, in some cases, seal the vacuum channel 148. In some methods of manufacturing, the pressure channel 146 and/or the vacuum channel 148 are formed by drilling a bore from one side 108 of the manifold 102 toward the other side 108 of the manifold 102. In some embodiments, the bore is a through bore. The bore can be plugged or otherwise sealed at the sides 108 of the manifold 102. The cross-channel can be any shape of sub-channel connecting at least in part to either a pressure channel or a vacuum channel. The cross-channel can form any angle with the pressure channel or a vacuum channel, including 30, 45 degrees, 60 degrees, 75 degrees, and 90 degrees etc. The term cross-channel does not imply that the cross-channel necessarily forms a 90 degree intersection with the pressure channel or a vacuum channel.

The inlet pressure port 142 can be connected to a source of pressurized gas (not shown) via tubing (not shown). The pressurized fluid such as a pressurized gas can travel from the inlet pressure port 142 through the pressure channel 146. The pressure channel 146 can supply gas under pressure to each pipette channel 110 connected to the manifold 102.

Similarly, the inlet vacuum port 144 can be connected to a vacuum source (not shown) via tubing (not shown). Gas in the vacuum channel 148 can be supplied with gas under vacuum via the inlet vacuum port 144 and the vacuum source. The vacuum channel 148 can supply gas under vacuum to each pipette channel 110 connected to the manifold 102. The pressure channel 146 and the vacuum channel 148 can be parallel bores through the manifold 102, as shown. The inlet pressure port 142 and the inlet vacuum port 144 can have standard connectors, for example industry-standard connectors that mate with suitable pneumatic tubing.

Figure 4:
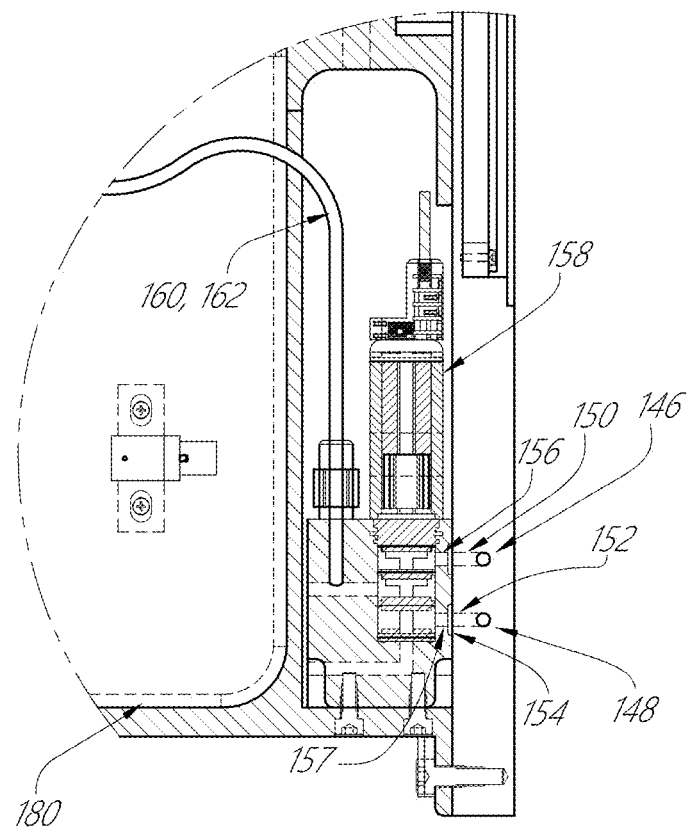
Figure 5:
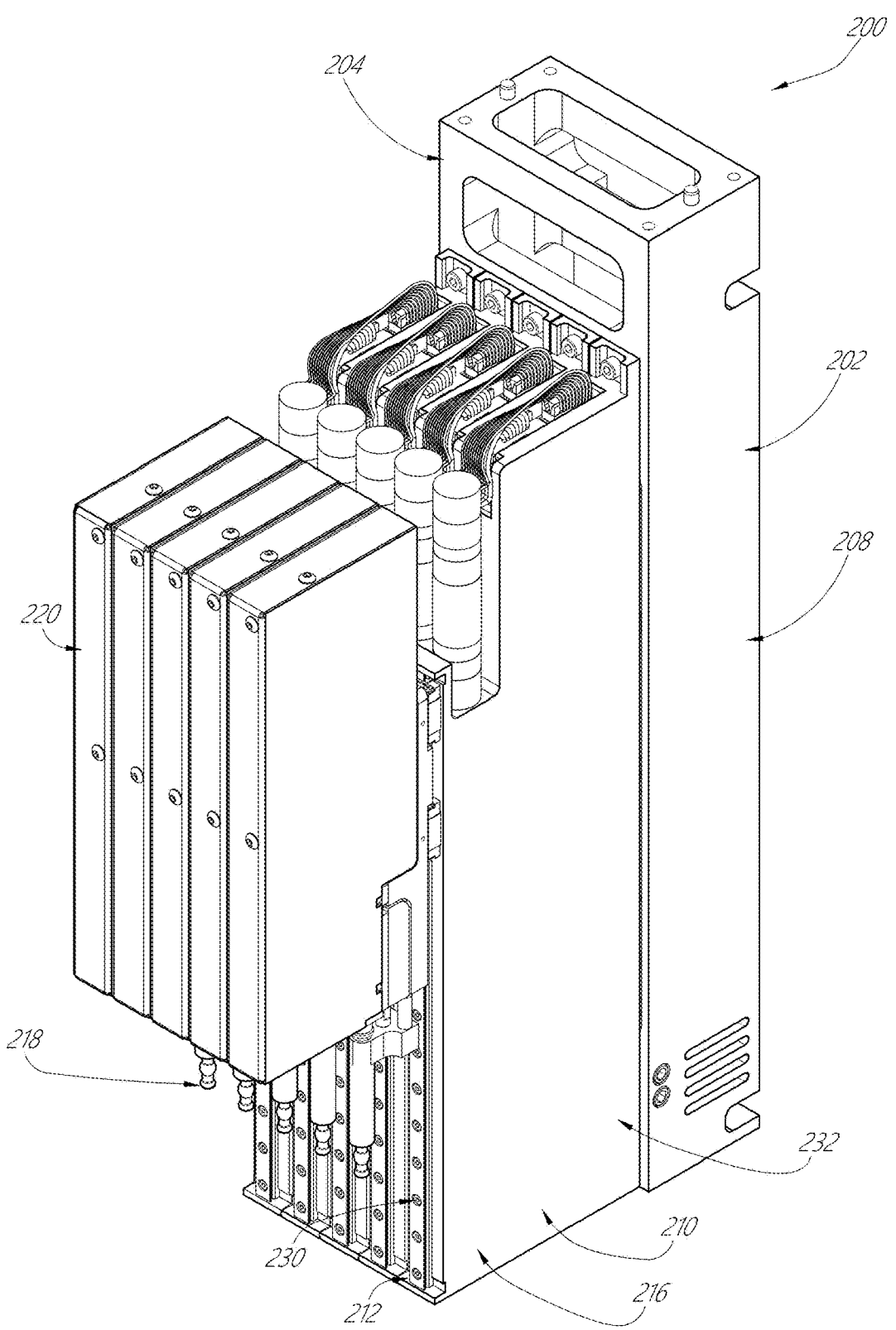
FIGS. 5-34D show views of a liquid dispenser according to a third embodiment.
Figure 6:
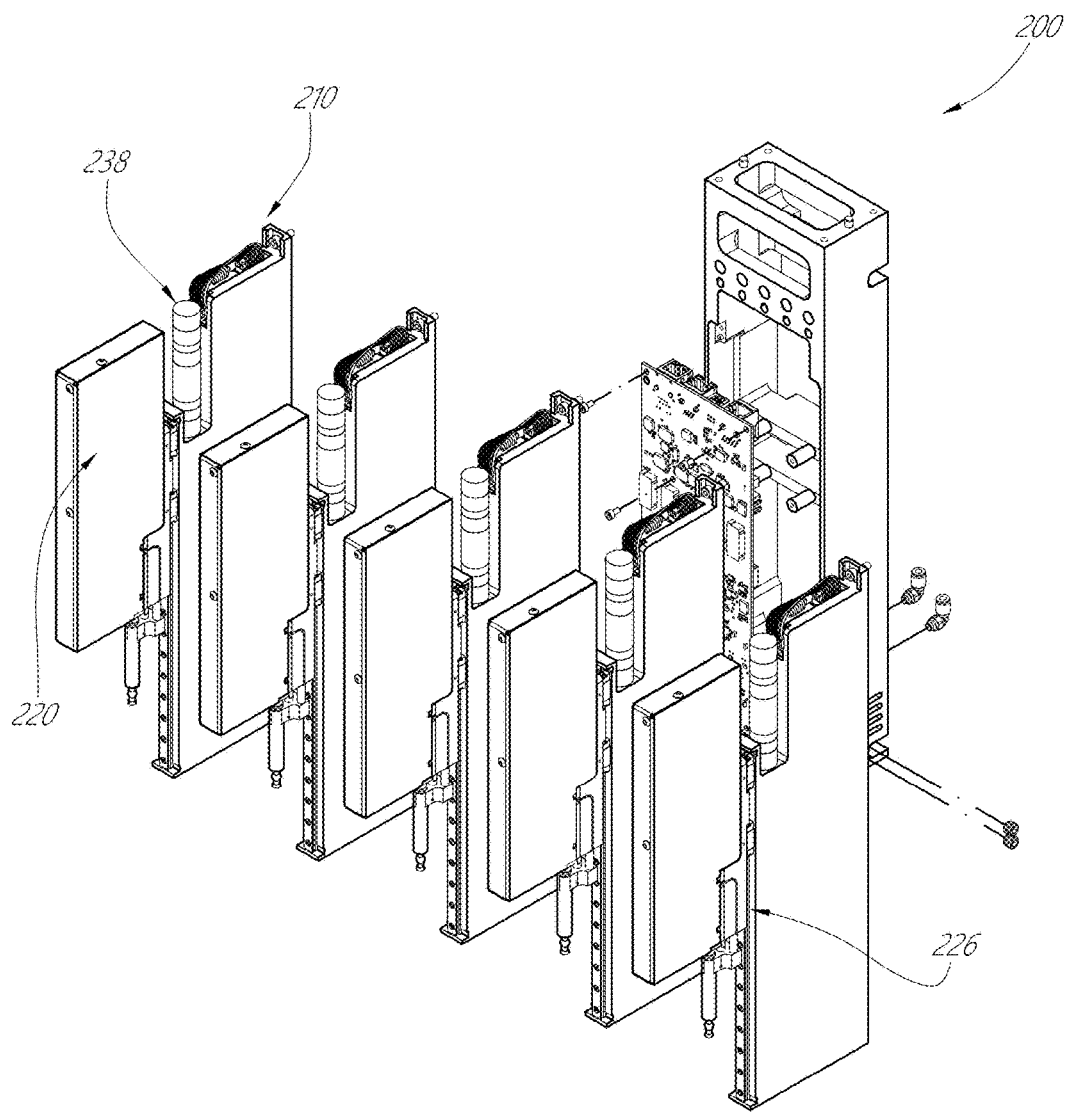
Figure 7:
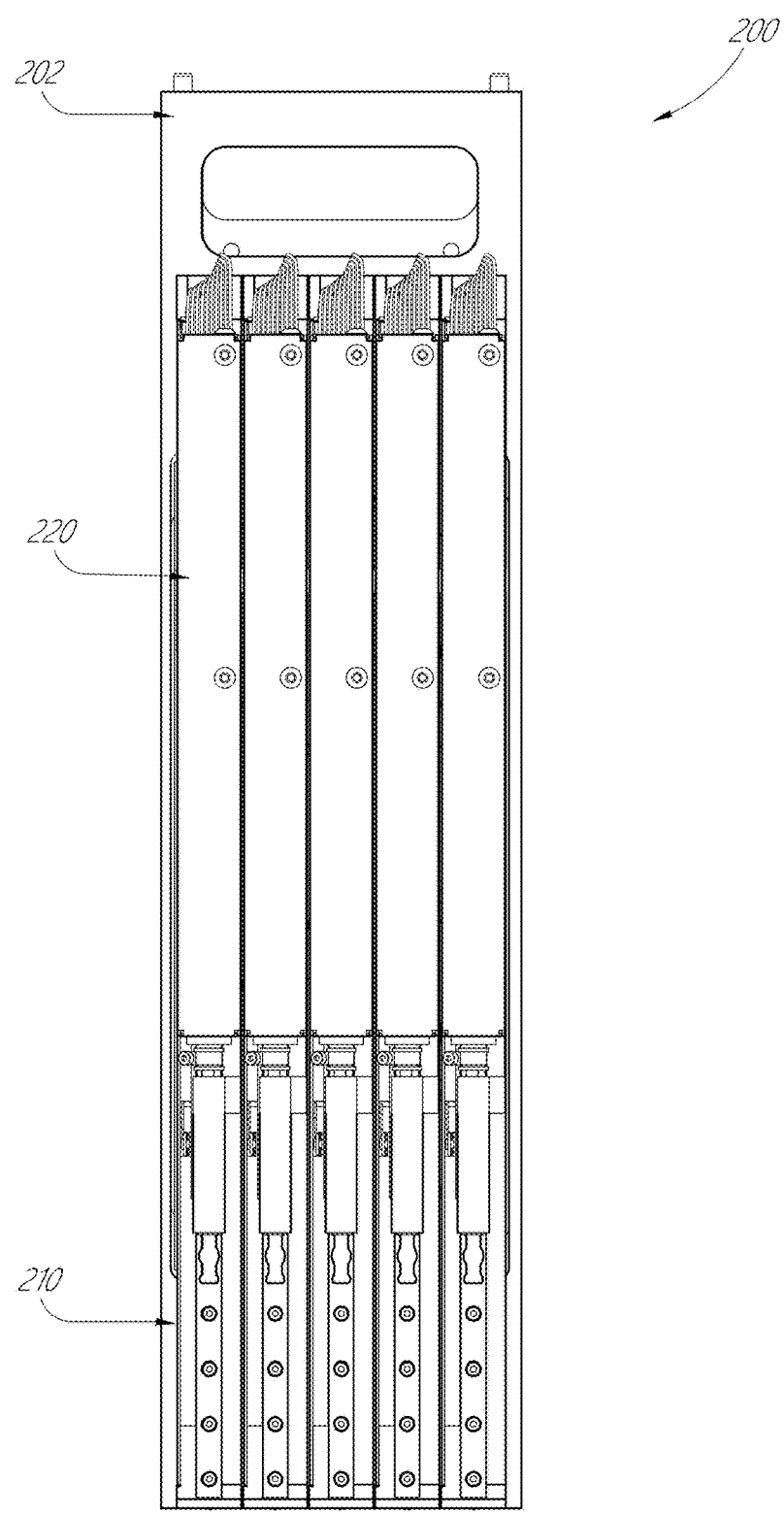
Figure 8:
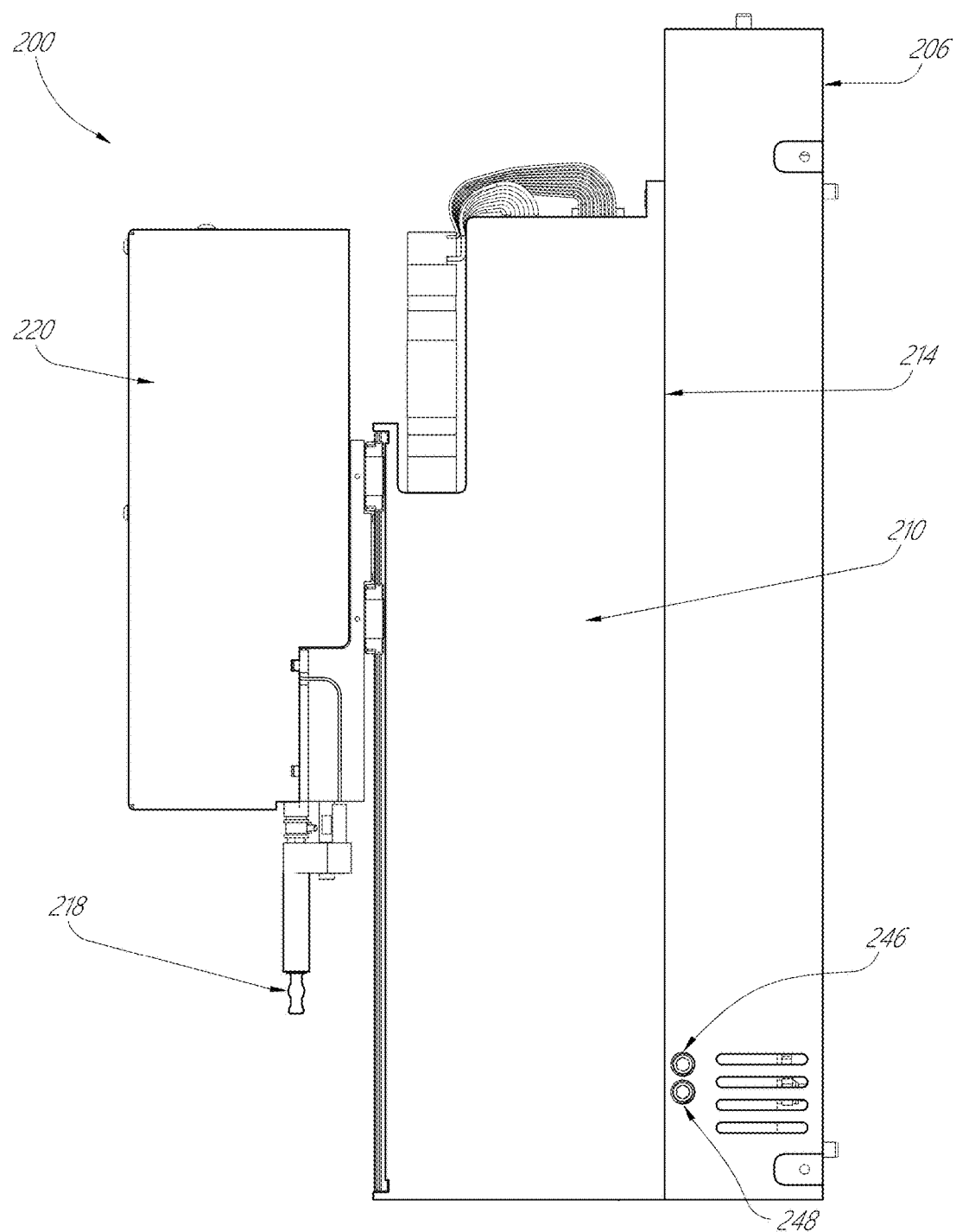
Figure 9:
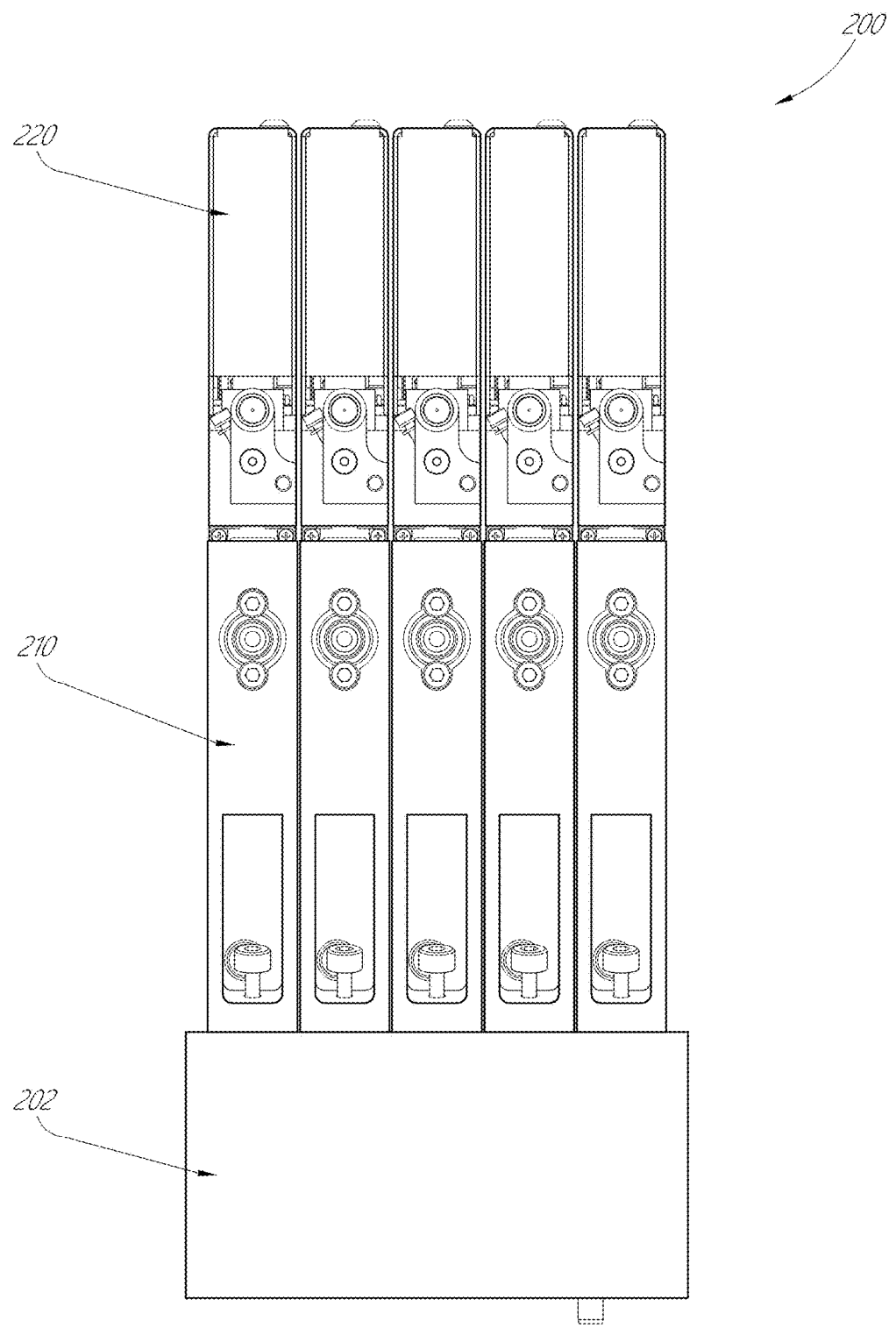
Figure 10:
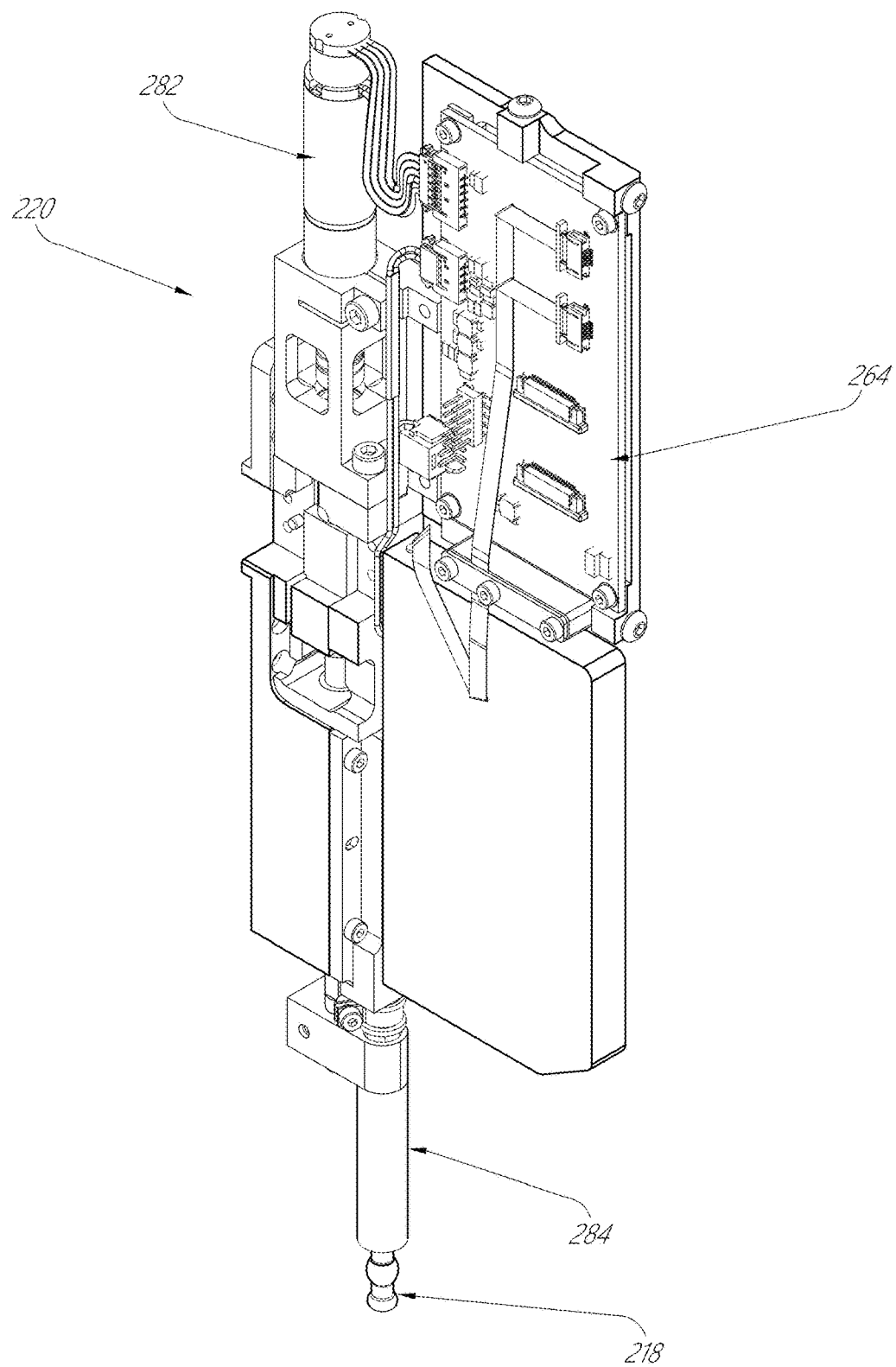
Figure 11:
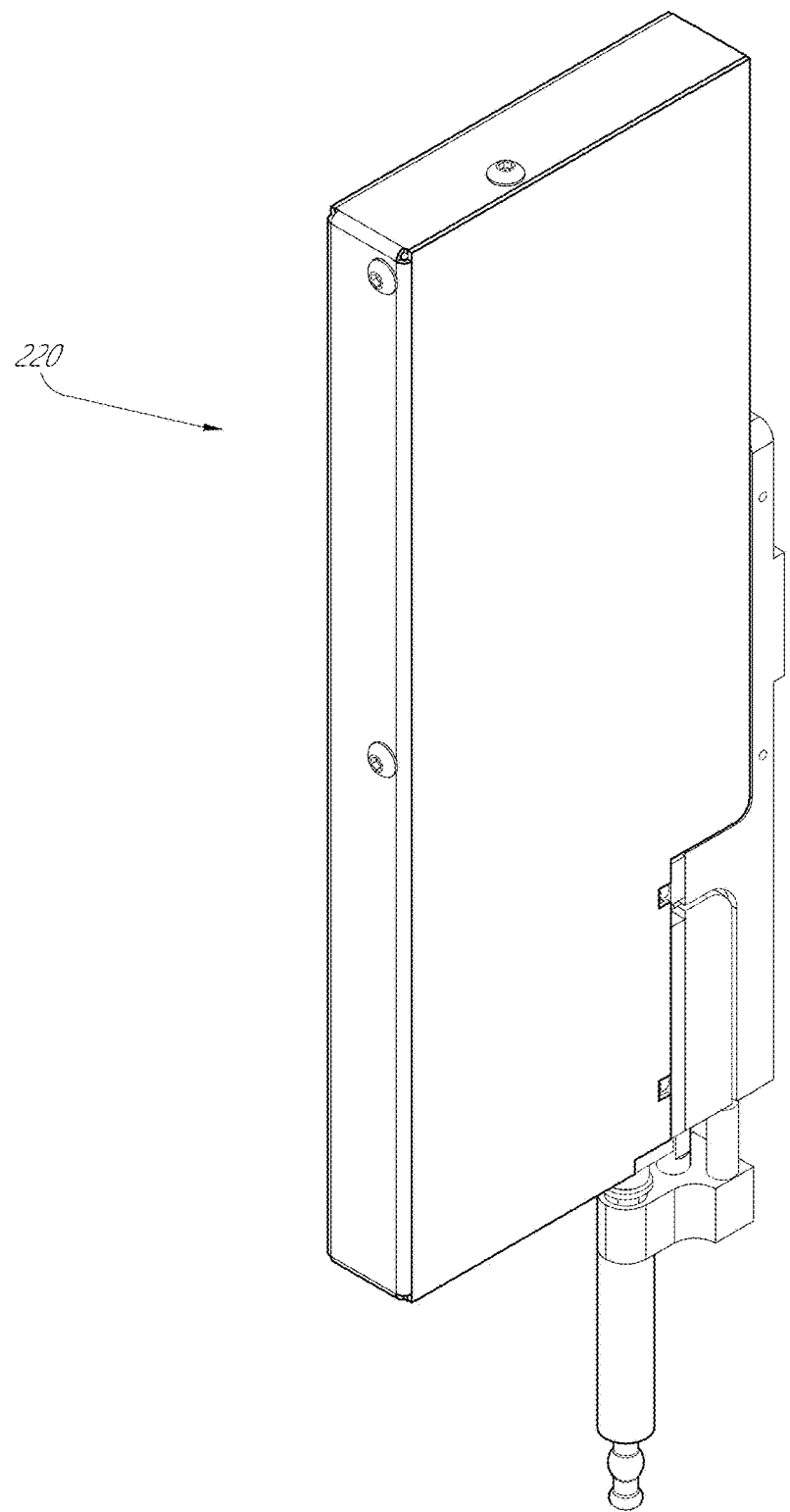
Figure 12:
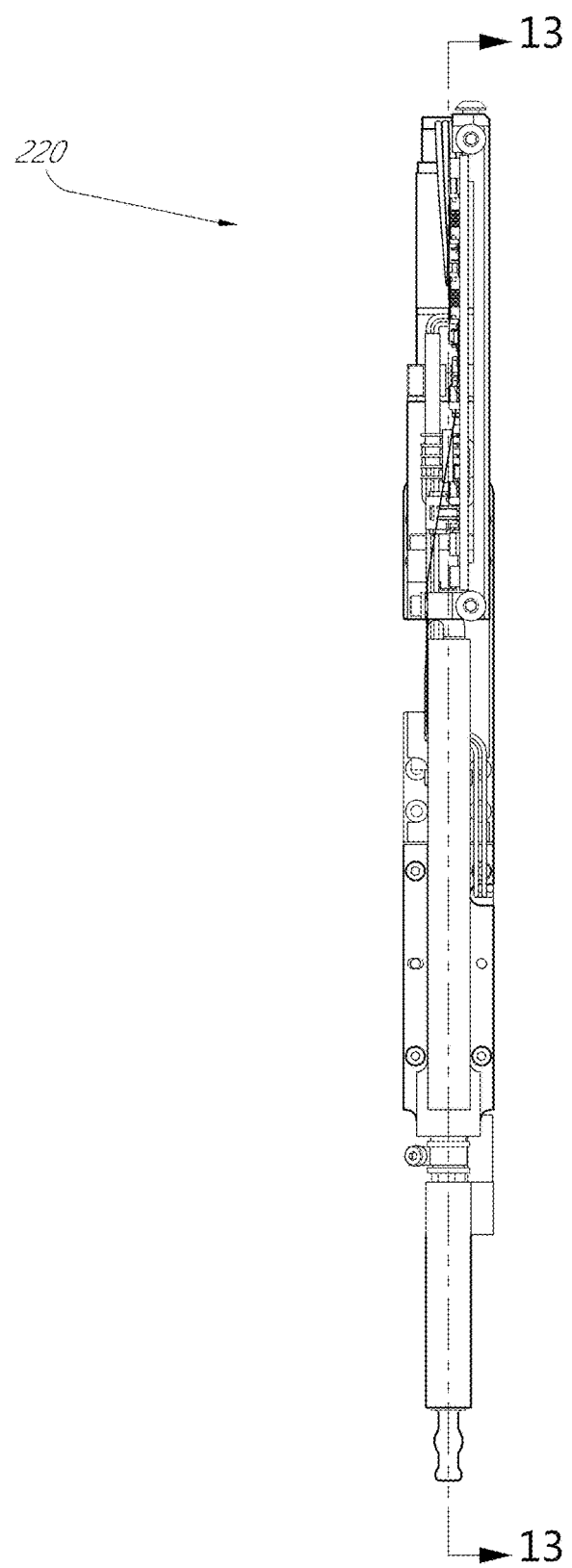
Figure 13:
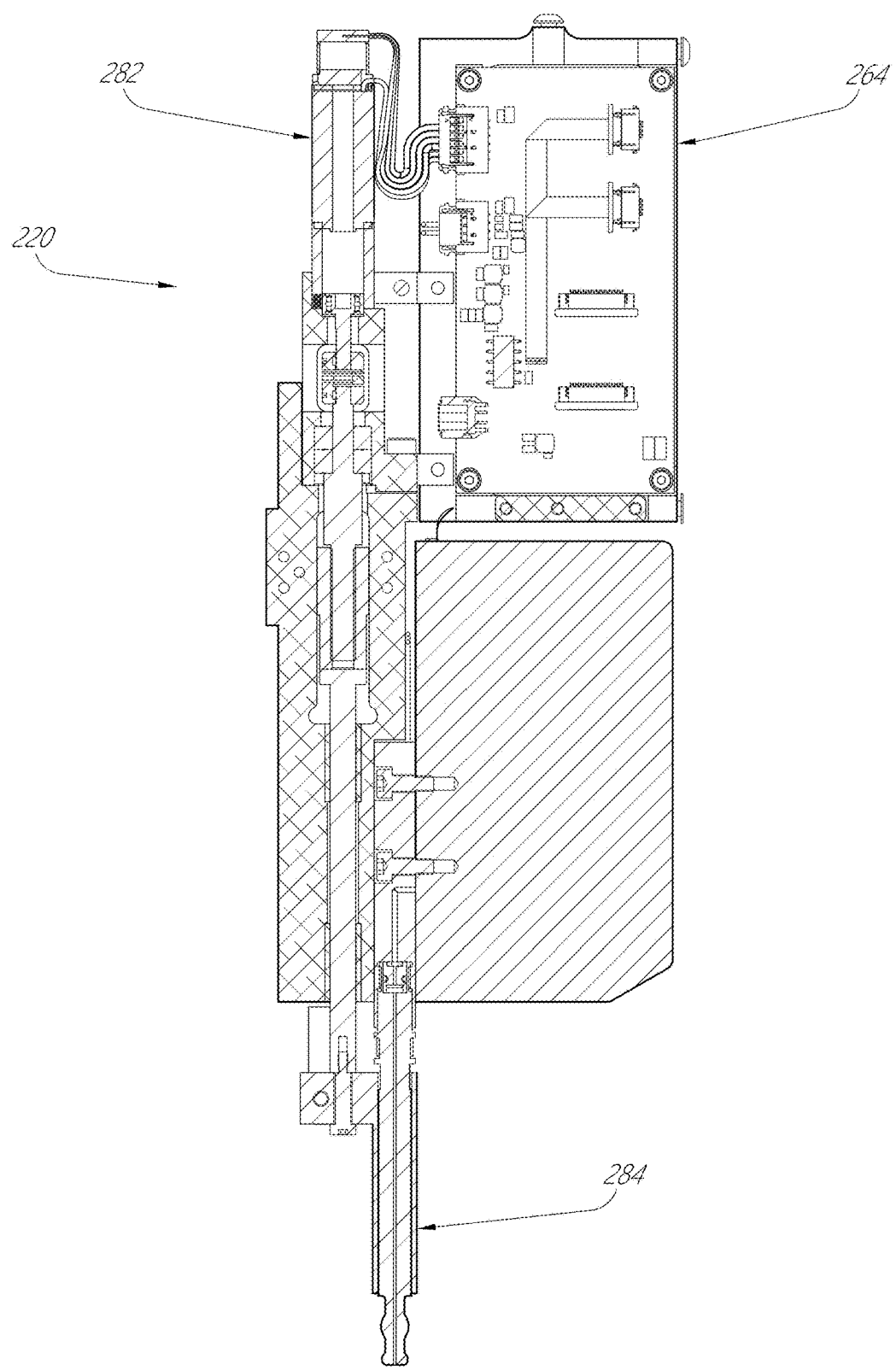
Figure 14:
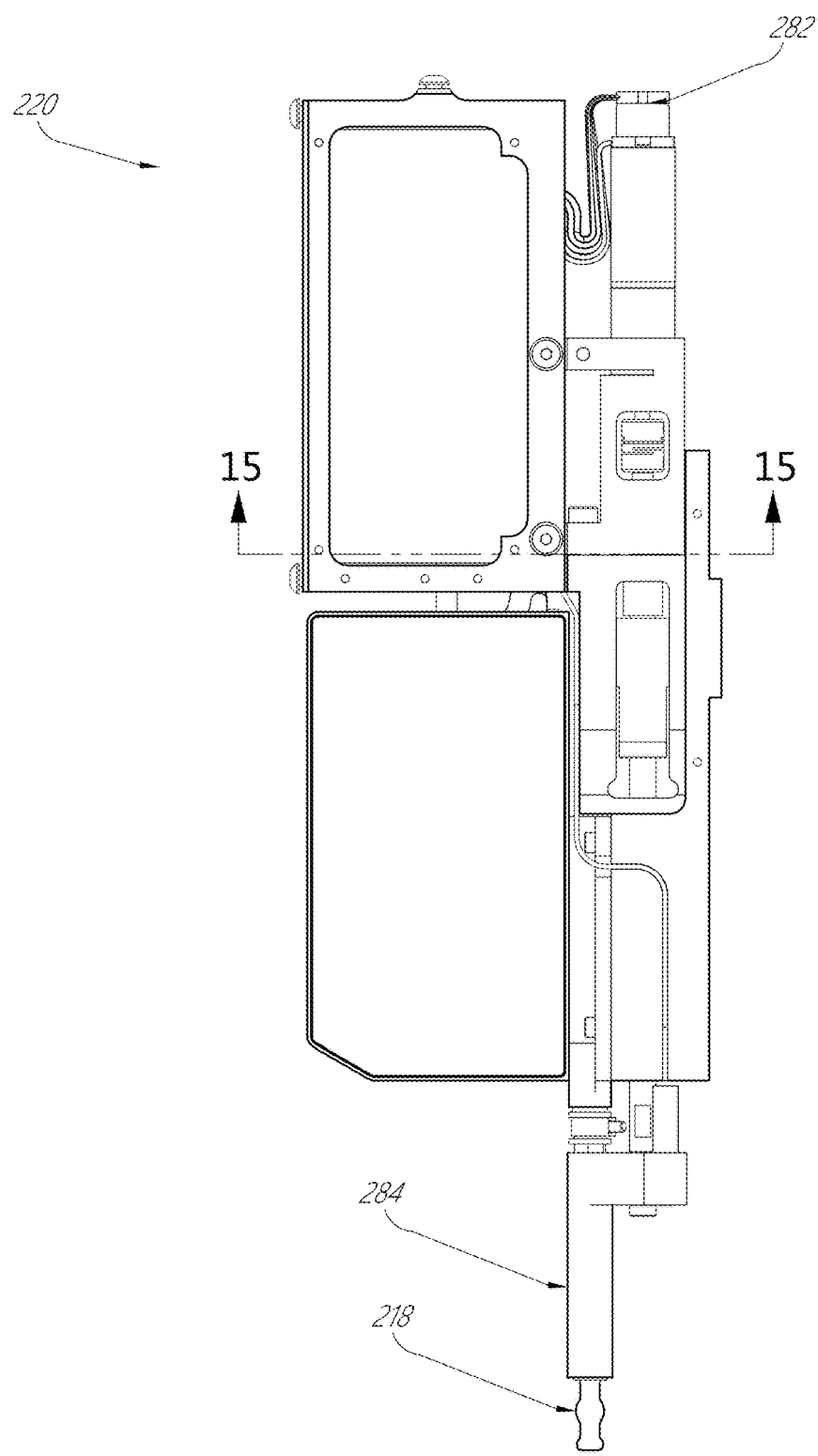
Figure 15:
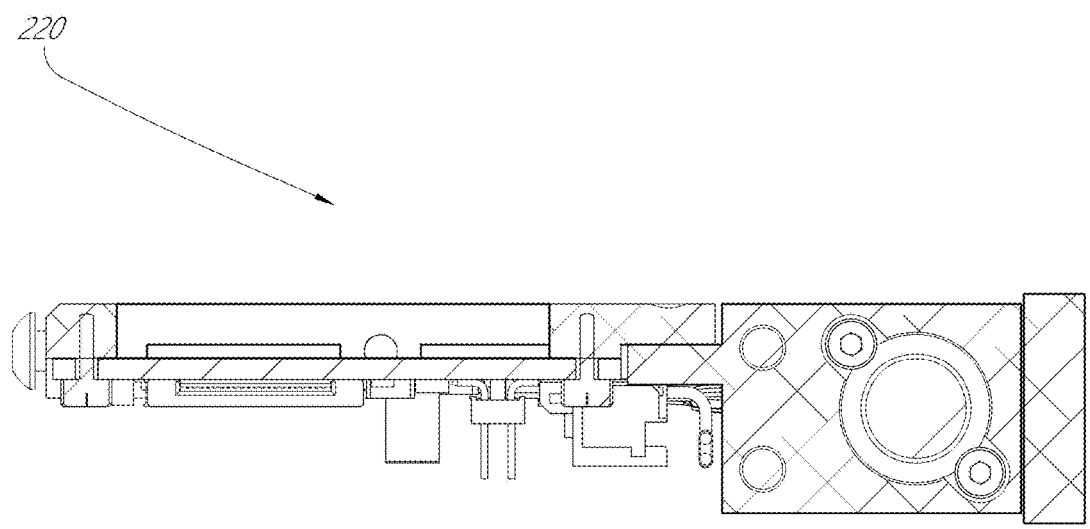
Figure 16:
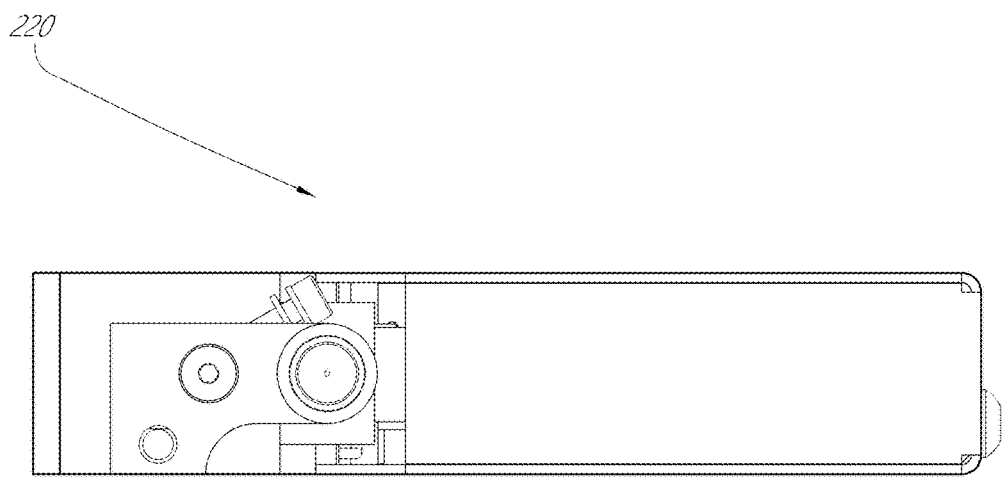
Figure 17:
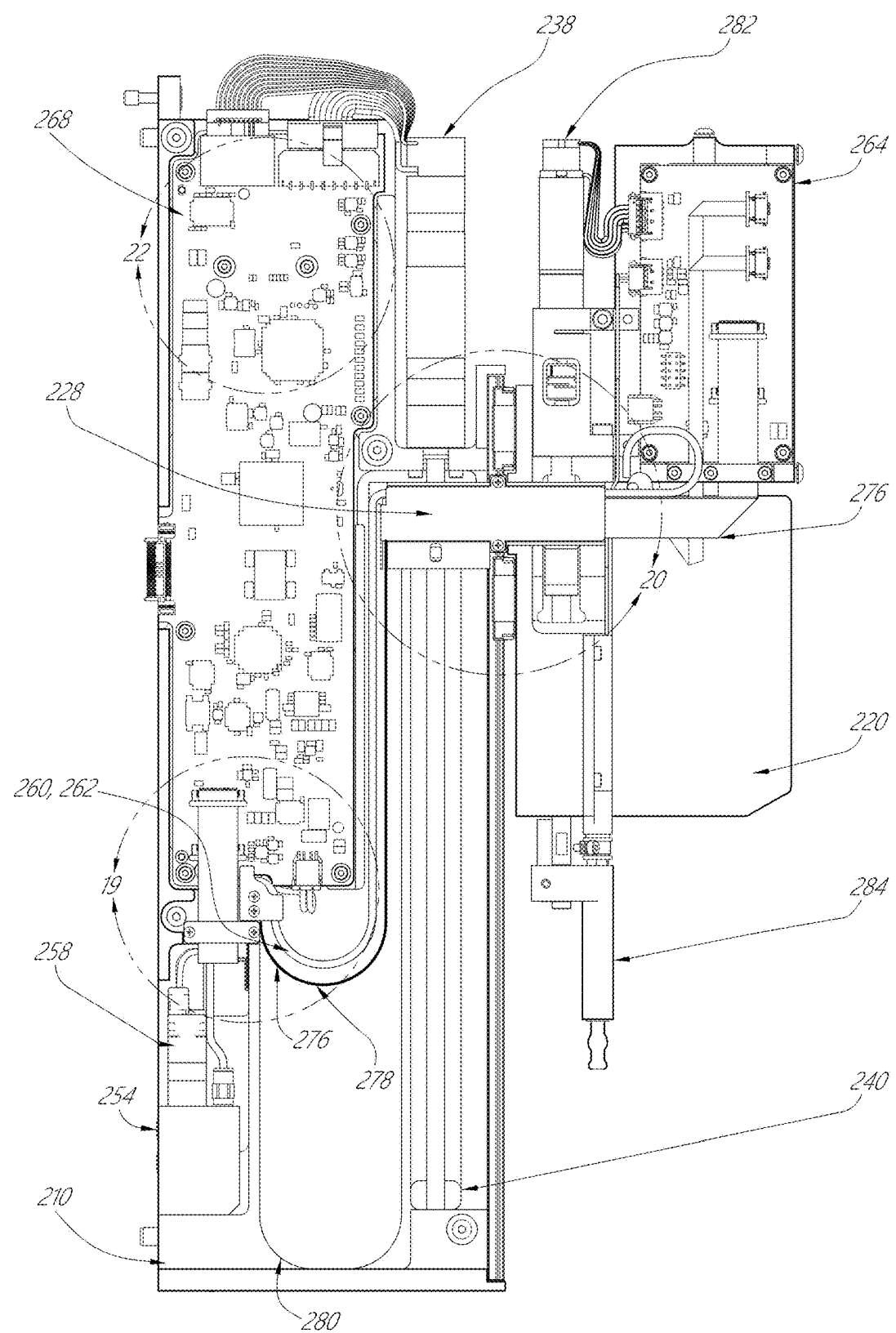
Figure 18:
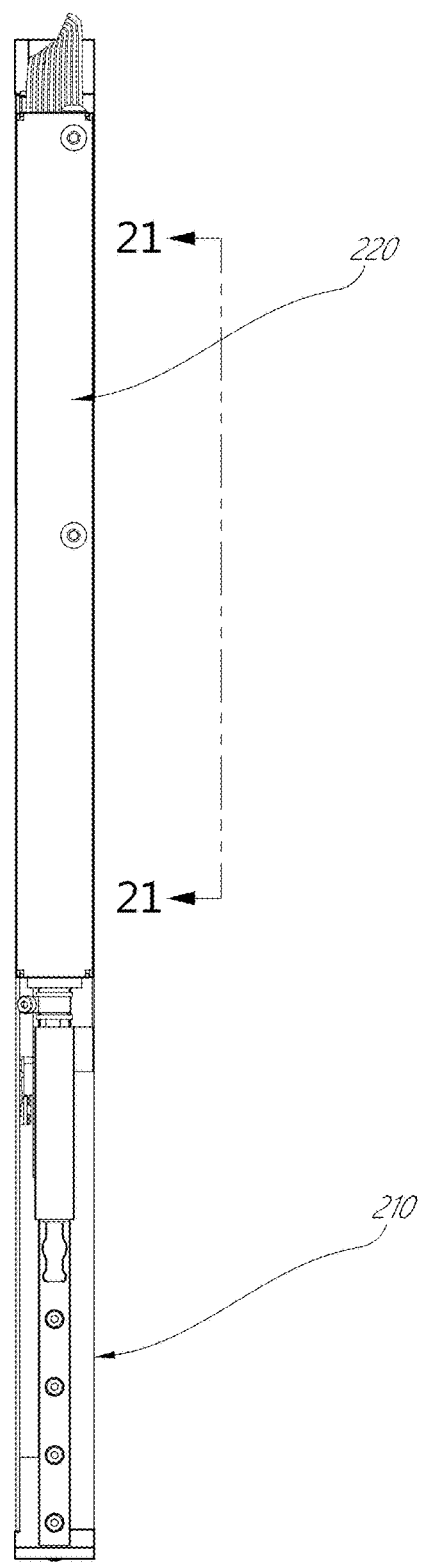
Figure 19:
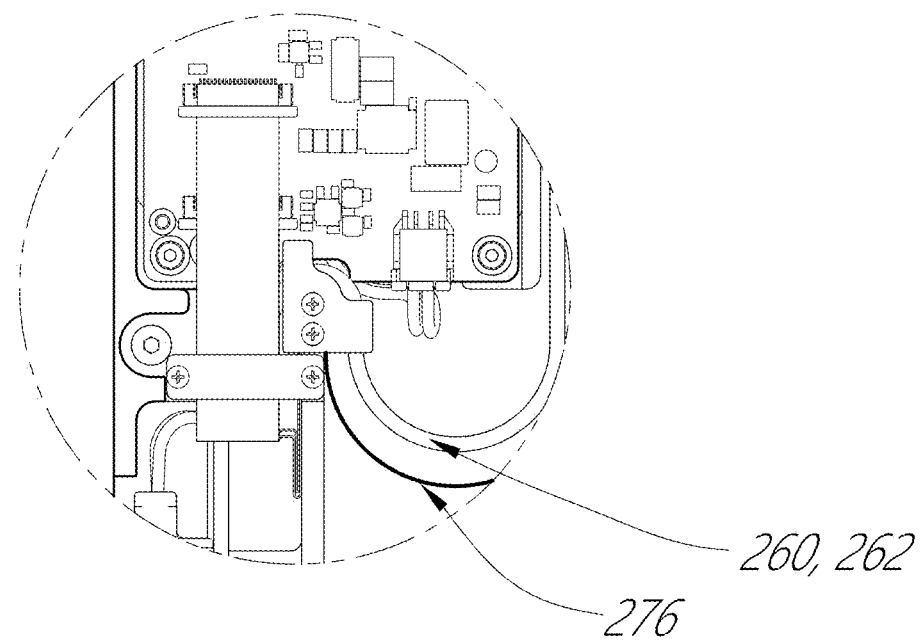
Figure 20:
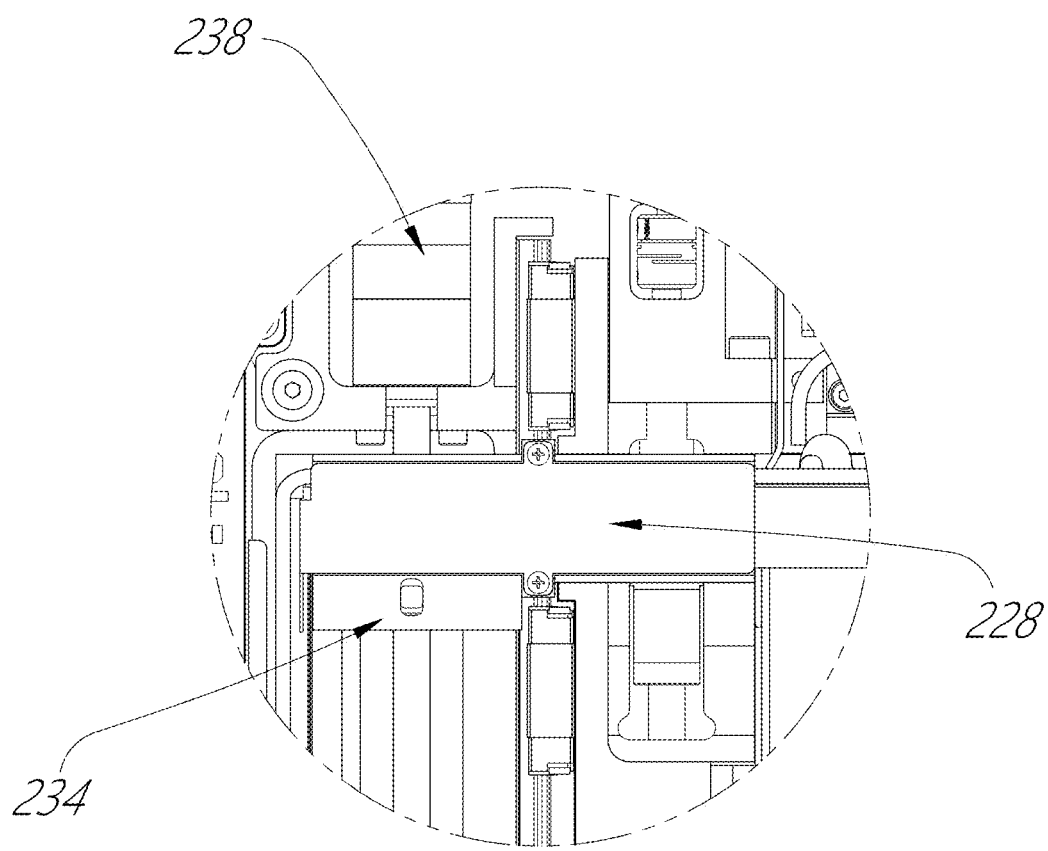
Figure 21:
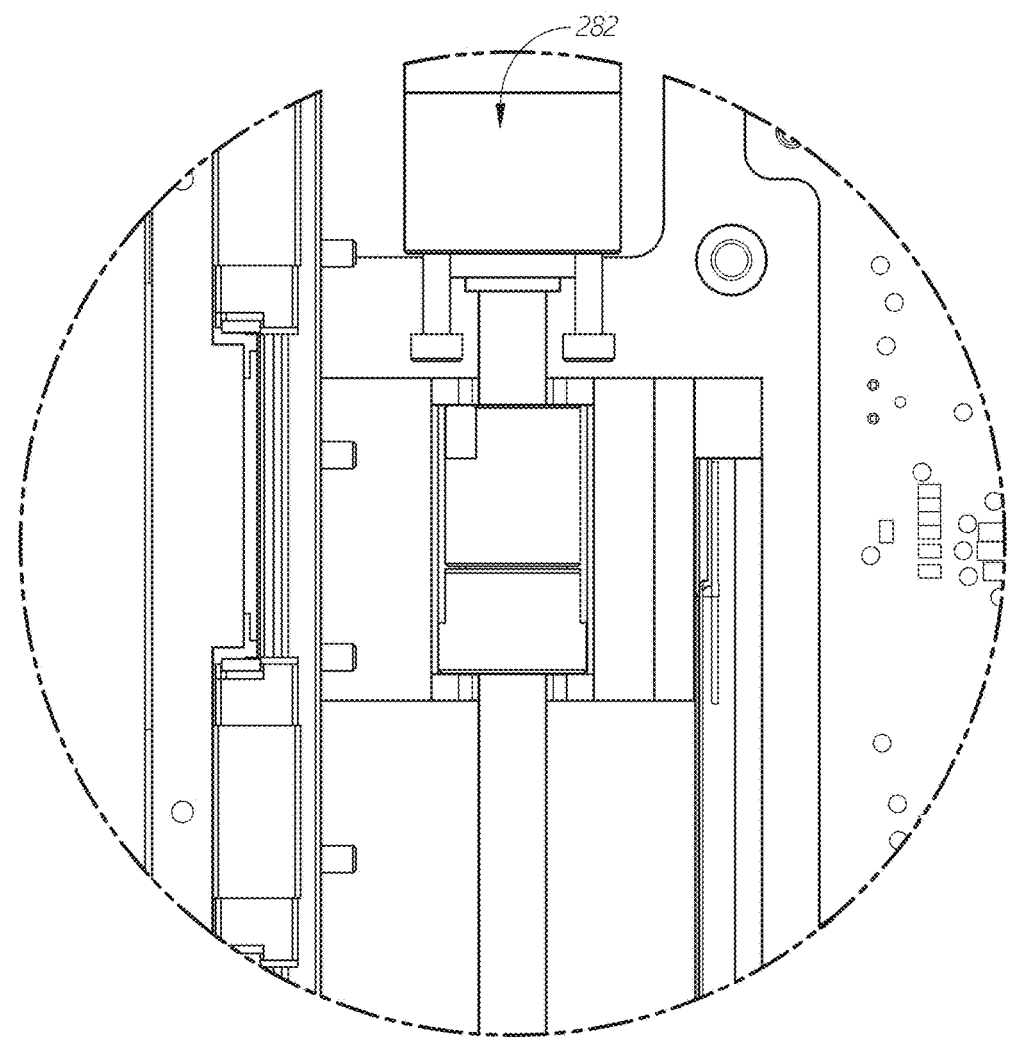
Figure 22:
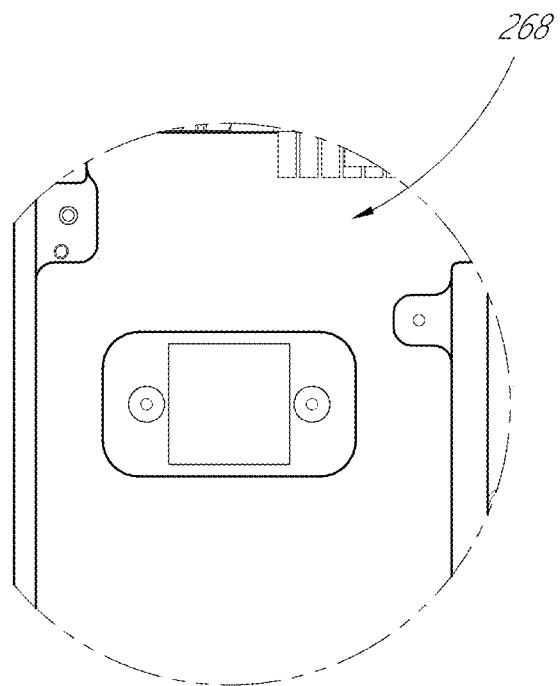
Figure 23:
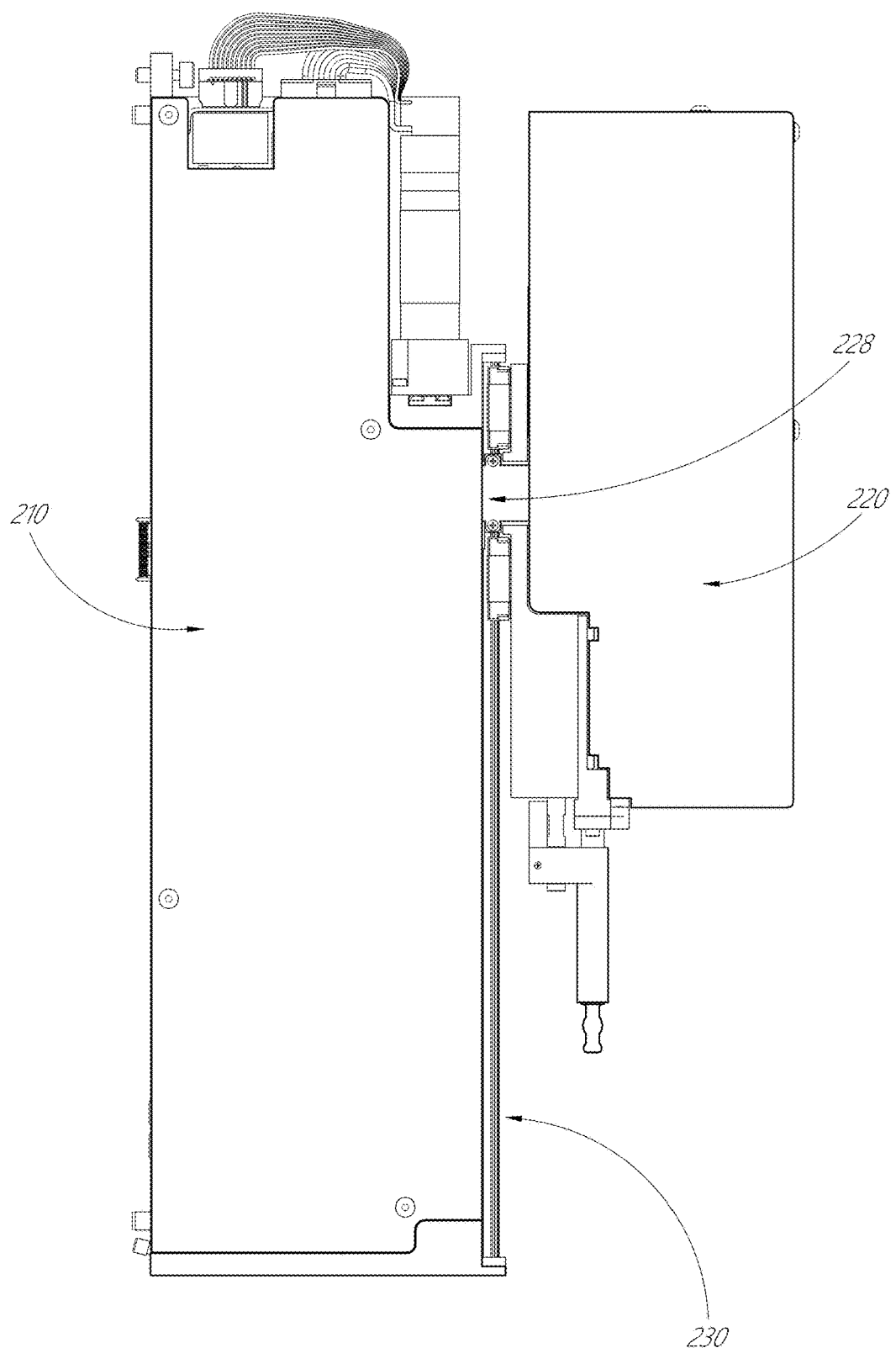
Figure 24:
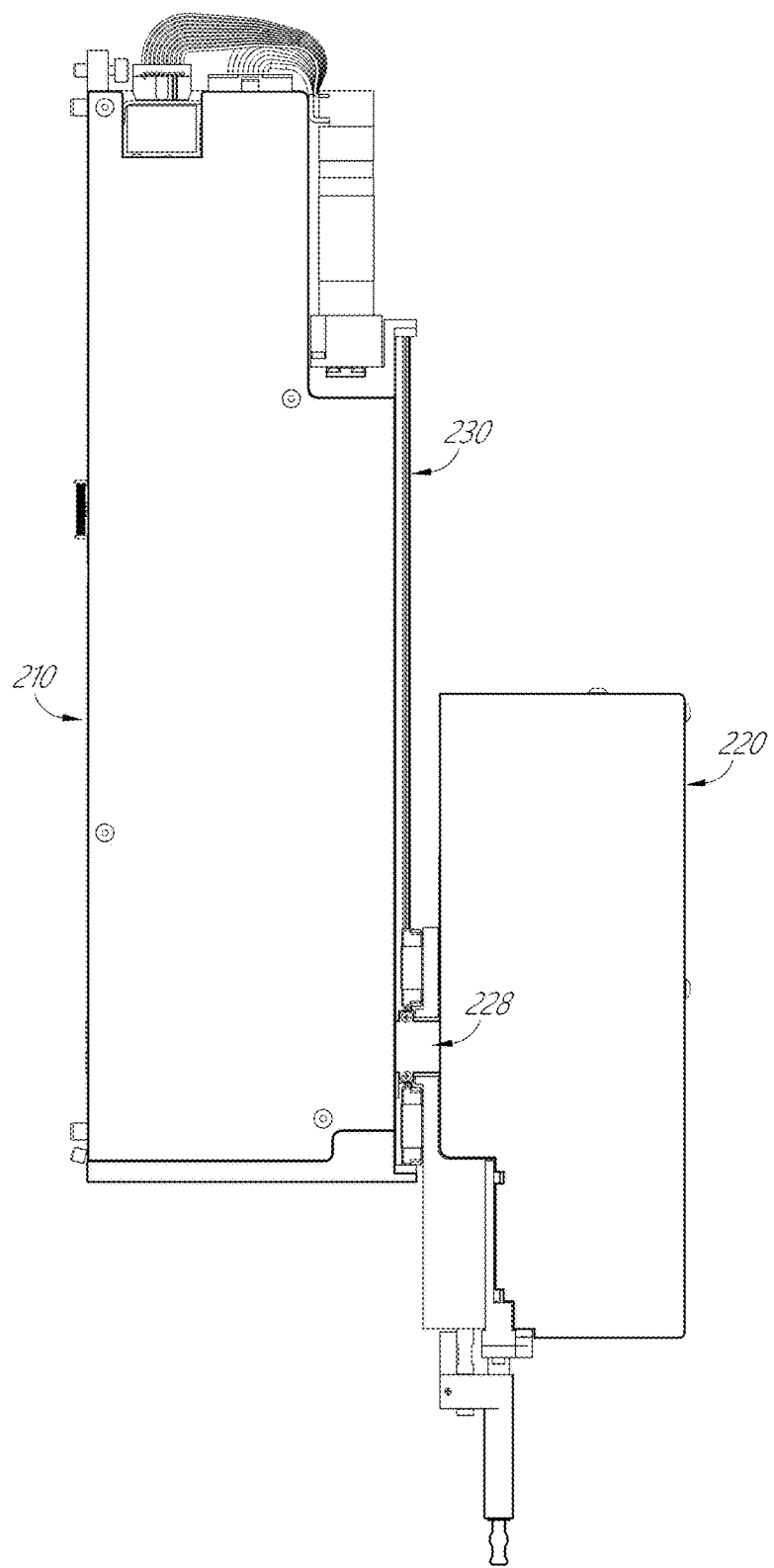
Figure 25:
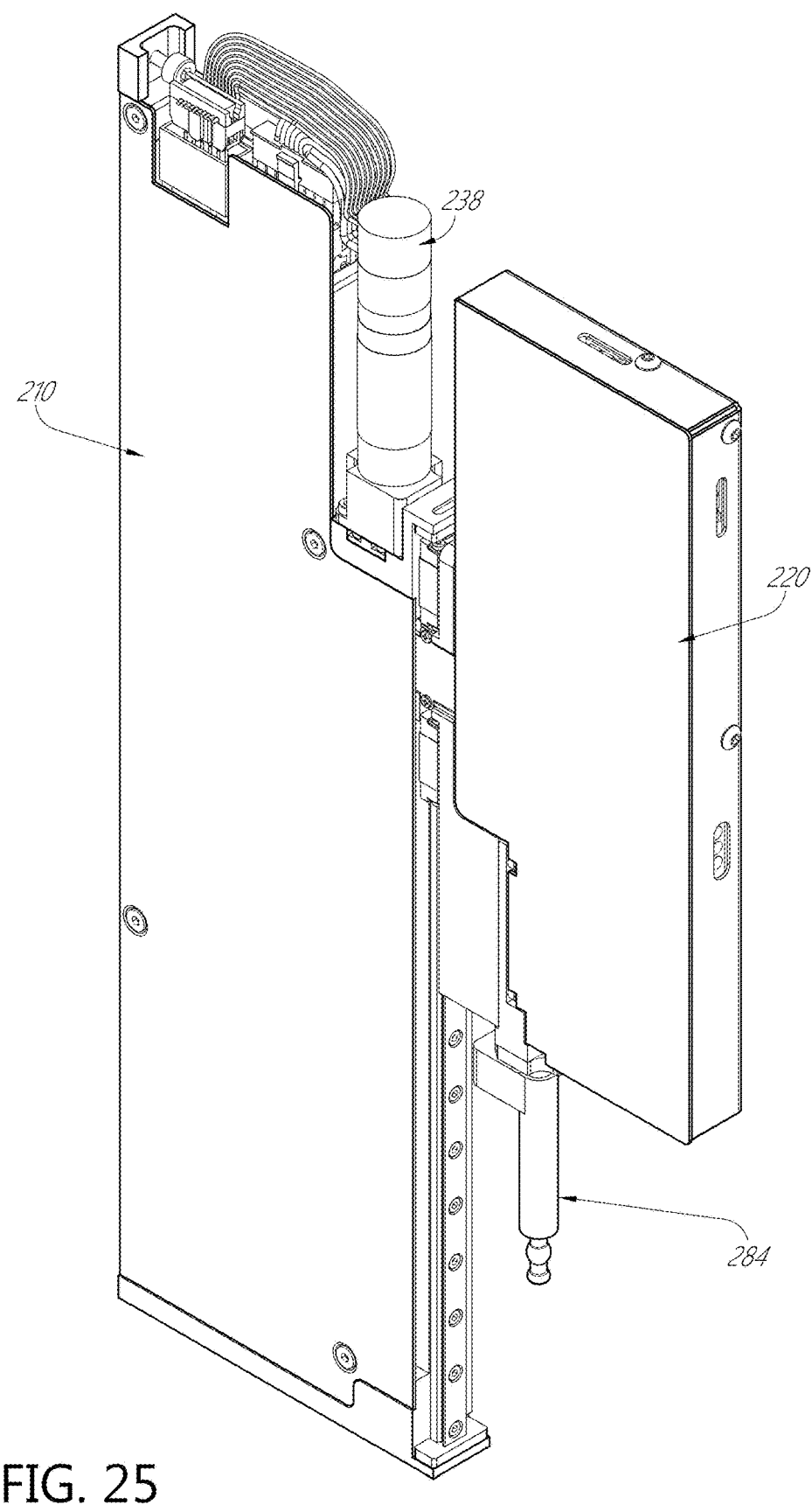
Figure 26:
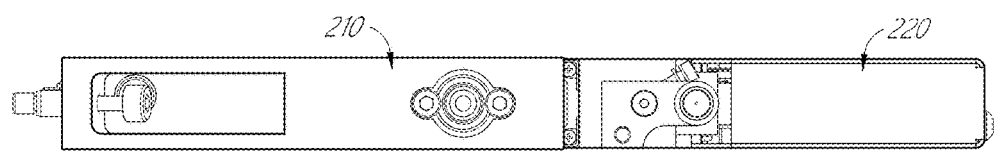
Figure 27:
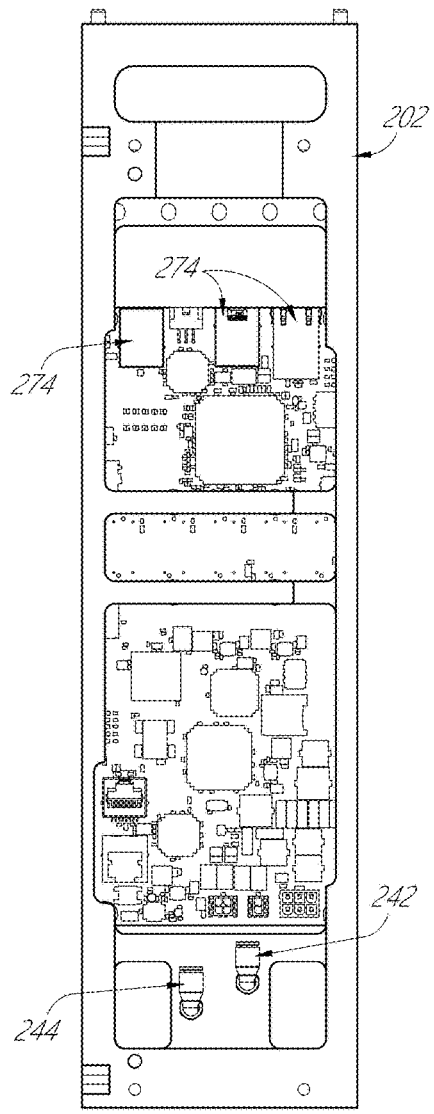
Figure 28:
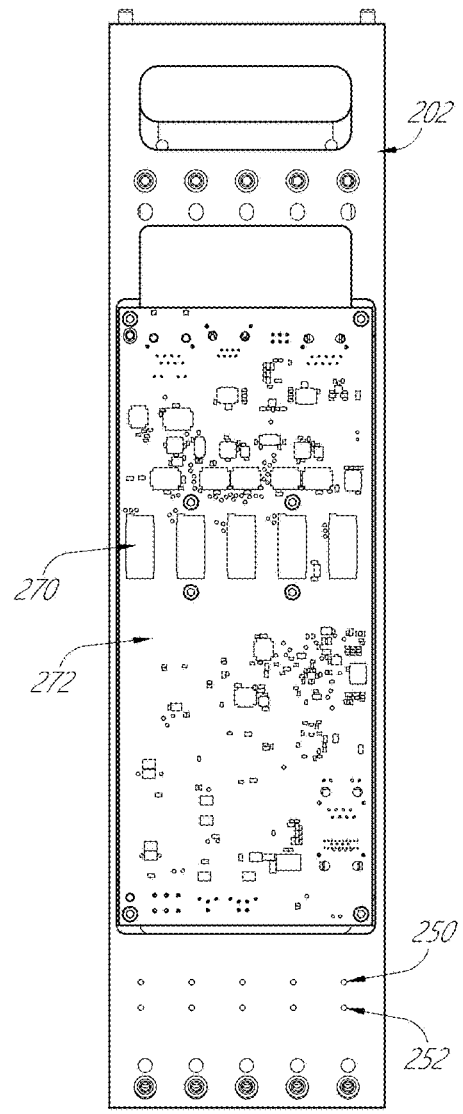
Figure 29:
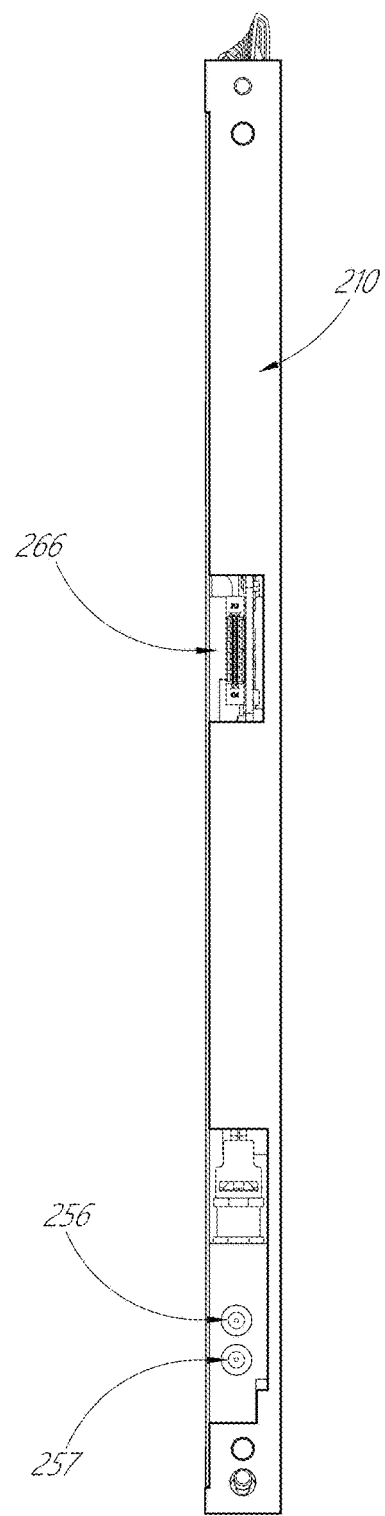

Referring to FIG. 4, the pressure channel 146 is shown extending through the manifold 102. The pressure channel 146 is connected to a pressure cross-channel 150. The pressure cross-channel 150 extends from the pressure channel 146 in the manifold 102 to the base 132 of the pipette channel 110. The pressure cross-channel 150 extends from the front of the manifold 102 to the back of the pipette channel 110. The pressure cross-channel 150 can be perpendicular to the pressure channel 146.

Similarly, the vacuum channel 148 is shown extending through the manifold 102. The vacuum channel 148 is connected to a vacuum cross-channel 152. The vacuum cross-channel 152 extends from the vacuum channel 148 in the manifold 102 to the base 132 of the pipette channel 110. The vacuum cross-channel 152 extends from the front of the manifold 102 to the back of the pipette channel 110. The vacuum cross-channel 152 can be perpendicular to the vacuum channel 148. In some embodiments, one pipette channel 110 can be removed from the liquid dispenser 100 (for example, disconnected from the front 104 of the manifold 102). The corresponding now-exposed pressure cross-channel 150 and vacuum cross-channel 152 may need to be covered. For instance, if one pipette channel 110 is removed, the user may install a blanking plate (not shown) that covers the exposed pressure cross-channel 150 and vacuum cross-channel 152. The blanking plate can include a peg near the top of the blanking plate and a peg near the bottom of the blanking plate. The blanking plate can include a fastener 124 near the top of the blanking plate and a fastener 124 near the bottom of the blanking plate. Other mechanisms configured to cover one or more of the pressure cross-channel 150 and vacuum cross-channel 152 are contemplated includes seals, plugs, adhesives, etc. The pressure cross-channel 150 and vacuum cross-channel 152 can be sealed such that one or more pipette channels 110 can be removed without adversely impacting the aspirate and dispense operations of another pipette channel 110 mated with the manifold 102.

As described herein, the pipette channel 110 is modular allowing the pipette channel 110 to be reversibly secured to and disconnected from the manifold 102. The pressure cross-channel 150 and the vacuum cross-channel 152 are structures in the manifold 102. The pressure cross-channel 150 associated with each pipette channel 110 spans a distance between the pressure channel 146 and a pressure port 156 on the back 114 of the pipette channel 110 when the pipette channel 110 is secured to the front 104 of the manifold 102. The vacuum cross-channel 152 associated with each pipette channel 110 spans a distance between the vacuum channel 148 and a vacuum port 157 on the back 114 of the pipette channel 110 when the pipette channel 110 is secured to the front 104 of the manifold 102. In some embodiments, the liquid dispenser 100 includes one or more features to improve the seal between the pipette channel 110 and the manifold 102. In some embodiments, an o-ring 154 seals a fluidic connection (for transfer of a gas, for example) between the pipette channel 110 and the manifold 102. The o-rings 154 can be located near the pressure cross-channel 150 and the vacuum cross-channel 152.

Embodiments of pressure channels 110 of described herein include an individually-actuatable solenoid valve 158 configured to control the flow of gas from the manifold 102 to the module 120 of the pressure channel 110. One pressure cross-channel 150 and one vacuum cross-channel 152 of the manifold 102 are each connected to the solenoid valve 158 of a corresponding pipette channel 110 when the pipette channel is mated to the manifold 102. The solenoid valve 158 can be located within the base 132 of the pipette channel 110. The solenoid valve 158 acts as a selector between vacuum and pressure.

In a first position, the solenoid valve 158 directs pressurized fluid, such as a gas under pressure, from the pressure cross-channel 150 through a tube 160. The tube 160 extends from the solenoid valve 158 to the module 120. In this first position of the solenoid valve 158, the tube 160 supplies pressurized fluid to the module 120. In some embodiments, pressurized fluid can act on a piston within the module 120 to dispense fluid from the pipette tip 122. In some embodiments, the module 120 can include a second valve (not shown) configured to control the aspirate or dispense operations. The second valve can be a solenoid valve. The second valve uses pressure and/or vacuum to control the aspirate or dispense operations. The module 120 can include a flow sensor to determine how much was aspirated or dispensed.

In a second position, the solenoid valve 158 directs fluid under vacuum, such as a gas under vacuum, from the vacuum cross-channel 152 through the tube 160. In other embodiments, the gas under vacuum is directed through a second tube 162. The tube 162 extends from the solenoid valve 158 to the module 120. In this second position of the solenoid valve 158, the tube 160 (or the tube 162, depending on the implementation) supplies gas under vacuum to the module 120. For instance, gas under vacuum can be supplied to the second valve within the module 120 to aspirate fluid into the pipette tip 122.

The solenoid valve 158 is integrated within the base 132 of the pipette channel 110. Advantageously, if a solenoid valve in a single pipette channel 110 of the liquid dispenser 100 malfunctions, requires maintenance, testing, inspection, or any other process requiring access to the solenoid valve 158, the entire pipette channel 110 with the affected solenoid valve 158 can be removed from the liquid dispenser 100 and replaced with another pipette channel 110. The pipette channel 110 forms a seal with the manifold 102 such that pressure and/or vacuum can be transferred from the manifold 102 to the pipette channel 110. When the pegs are aligned with the manifold during installation of the pipette channel 110, the pressure cross-channel 150 and the vacuum cross-channel 152 create a continuous pathway for gas under pressure and gas under vacuum. The pipette channel 110 and the manifold 102 form a pneumatic connection via the pressure cross-channel 150 and the vacuum cross-channel 152. The pneumatic connection can be a physical connection which is formed when the pipette channel 110 mates with the manifold 102.

The manifold 102 can be a pneumatic manifold to supply fluid under vacuum and pressurized fluid to each pipette channel 110. In some embodiments, the pneumatic solenoid valve 158 is integrated into each pipette channel 110 and acts as a selector between vacuum and pressure. Pneumatic tubing is reduced or eliminated by integrated, modular pathways in the manifold 102 and the pipette channels 110 of the present disclosure. The integrated pathways can be sealed with o-rings at the interface between the manifold 102 and the pipette channels 110. Tubing between the solenoid valve 158 and the pipette channel 110 can be eliminated by placement of the solenoid valve 158 within the base 132 of the pipette channel 110.

The pipette channel 110 can form an electrical connection with the manifold 102. The electrical connection can include a physical connection which is formed when the pipette channel 110 mates with the manifold 102. As shown in FIG. 3, the pipette channel 110 can include an electrical connector 166 on the back side 114 of the pipette channel 110. The electrical connector 166 can be coupled to a circuit board 168 within the pipette channel 110. Each pipette channel 110 can include a circuit board 168 and corresponding electrical connector 166. The manifold 102 can include one or more electrical connectors 170 on the front side 104 of the manifold 102. Each electrical connector 170 is configured to electrically connect to a corresponding circuit board 168 of a pipette channel 110 mated with the manifold 102. The electrical connector 170 can be considered a backplane connector. The manifold 102 can include a circuit board 172. The electrical connectors 166, 170 can allow communication of electrical signals and control signals between the manifold 102 and the pipette channel 110. As described herein, the control signals can be data signals designed to control one or more operations of the pipette channel 110. The electrical signals can include electrical power to the components of the pipette channel 100, such as AC/DC electricity. The electrical connectors 166, 170 can allow communication of electrical signals between the circuit boards 168, 172. The circuit boards 168, 172 can be printed circuit boards. The mating electrical connectors 166, 170 can eliminate or reduce electrical cables and/or connections that are required to form an electrical connection between the manifold 102 and the pipette channels 110. The module 120 can include circuit board 164. The circuit board 164 can be associated with the aspirate and dispense operations. The circuit boards 164, 168, and/or 172 can be electrically connected. In some embodiments, circuit boards 164 and 168 are physically connected via a ribbon cable 176. The ribbon cable 176 can extend along the coupling 128 at the interface between the pipette channel 110 and the module 120. The ribbon cable 176 can transmit control signals and electrical signals. In some embodiments, movement in the Z-direction of the pipette tip 122 engaged to the module 120 is controlled by features housed in the pipette channel 110, for instance, controlled by the circuit board 168. The z-axis control hardware can be located within the pipette channel, for instance on circuit board 168. In some embodiments, the circuit board 164 acts as an interconnect board and also contains the capacitive sense circuit.

The manifold 102 can include one or more additional electrical connectors 174. In FIGS. 1B-4, the manifold includes three electrical connectors 174. The electrical connectors 174 can include different configurations and shapes to accommodate different electrical connections. The electrical connectors 174 can include an Ethernet connection. The Ethernet connection can provide signals to the circuit boards 168, 172. The electrical connectors 174 can include a power connector. The power connector can supply electrical power to the motor 138 and the solenoid valve 158 within each of the pipette channels 110 when they are mated to the manifold 102. The electrical connector 174 can include a module connection. The module connection can control the module 120, for instance the aspirate and dispense operations of the module 120. Other electrical connectors 174 are contemplated. One or more electrical connectors 174 can be located on the front 104, back 106, or sides 108 of the manifold 102. In the illustrated embodiments, all of the electrical connectors 174 are located on the front 104 of the manifold 102. In some embodiments, the number of electrical connectors 174 does not depend on the number of pipette channels 110. For instance, in the illustrated embodiment, three electrical connectors 174 are included regardless of the maximum number of pipette channels 110 the manifold 102 can accept.

The pipette channel 110 can be designed to accommodate internal wiring and tubing. The pipette channel 110 can house the tubes 160, 162 extending from the solenoid valve 158 to the module 120. The pipette channel 110 can include a ribbon cable 176 which transmits electrical signals and control signals. The electric signals can include signals from the electrical connectors 174. The ribbon cable 176 can extend from the electrical connector 166 on the back side 114 of the pipette channel to the module 120. The tube 160, the tube 162 (if included), and the ribbon cable 176 can each include a bend 178. The bends 178 in the tube 160, 162 and the ribbon cable 176 are shown in an upward position in FIG. 4. The upward position of the bends 178 in the tubes 160, 162 and the ribbon cable 176 corresponds to an upward position of the module 120. As the module 120 moves downward, the bends 178 in the tubes 160, 162 and in the ribbon cable 176 move downward within the base 132 of the pipette channel 110. The bends 178 in the tubes 160, 162 and in the ribbon cable 176 can be accommodated within a groove 180 in the base 132 of the pipette channel 110.

In the illustrated embodiment, the five pipette channels 110 are located to the left of the electrical connectors 174, the inlet pressure port 142, and the inlet vacuum port 144. Implementations of manifold 102 described herein can be configured to accept additional pipette channels 110, which may increase the width of the manifold in the X-direction. Decreasing the number of pipette channels 110 the manifold 102 is configured to accept may decrease the width of the manifold 102 in the X-direction. The pipette channels 110 can be arranged such that the pipette tips 122 are aligned. The distance between adjacent pipette tips 122 can be designed to accommodate the spacing of the associated containers for the aspirate and dispense operation. In the illustrated embodiments, the pipette tips 122 are 18 mm apart center to center. The associated containers are 9 mm apart center to center. Accordingly, in this non-limiting arrangement, the pipette tips 122 can engage every other container (e.g., a first subset of the containers) in a first position. The liquid dispenser 100 can be moved 9 mm to the right or left in the X-direction to engage every other container (e.g., a second subset of the containers).

In an embodiment not shown, features of manifold 102 can be incorporated within a plurality of pipette channels 110 that are permanently secured in a stacked formation adjacent to each other, thereby eliminating the manifold 102. The electrical connector 166 of each pipette channel 110 can be located on a side 116 of the pipette channel 110 to communicate signals to and from adjacent pipette channels 110. The pressure channel 146 can extend through the stacked pipette channels 110. The vacuum channel 148 can extend through the stacked pipette channels 110. One or more o-rings 154 can seal the pressure channel 146 and/or vacuum channel 148 between the stacked pipette channels 110. The pressure channel 146 and vacuum channel 148 can connect to pressure cross-channels 150 and vacuum cross-channels 152 as described herein.

Embodiments described herein advantageously enable independent movement of each of a plurality of modules 120 along the Z-axis direction, allowing each of a plurality of samples to be independently and simultaneously aspirated and dispensed within the liquid dispenser 100. In configurations that include more than one pipette channel, each of the plurality of pipette channels includes an individually-actuatable coupling 128 that moves along a ball screw 136 to translate the module 120 (independently of other modules 120) relative to the base 132 of the pipette channel 110.

Embodiments described herein also advantageously reduce pneumatic tubing to modular, individually-actuatable pipette channels. Independently operating multiple pipette channels 110 positioned next to each other would typically require multiple pneumatic tubes running to each pipette channel 110 from a common pneumatic pressure and vacuum source. The common pneumatic pressure and vacuum source can be a remotely mounted solenoid valve manifold. The remotely mounted solenoid valve manifold makes it difficult to route the tubing to each pipette channel 110. In such an arrangement, the pneumatic tubes running to each pipette channel 110 would be both visible and cumbersome. The multiple pneumatic tubes may impede motion, such as motion of the liquid dispenser along a gantry. The remotely mounted solenoid valve manifold would require much longer tubing or multiple sections of tubing to span from the remotely mounted solenoid valve manifold to each pipette channel 110. In contrast, liquid dispensers described herein reduce pneumatic tubing down to two pneumatic tubes connecting to the manifold 102; that is, one pneumatic tube (not shown) connecting to the inlet pressure port 142 and one pneumatic tube (not shown) connecting to the inlet vacuum port 144. Each pipette channel 110 is supplied pressurized gas and gas under vacuum through the pressure channel 146 and vacuum channel 148, respectively. This eliminates separate pneumatic tubing to each pipette channel 110. In other embodiments, separate pneumatic tubing is supplied to each pipette channel 110. In some embodiments, a separate piece of pneumatic tubing 160, 162 is provided inside each pipette channel 110 that connects the module 120 to the solenoid valve 158. Such embodiments are still advantageous over systems using a remotely mounted solenoid manifolds because the tubing 160, 162 is very short and self-contained inside the pipette channel 110 and module 120.

Advantageously, embodiments described herein also reduce electrical connections to modular, individually-actuatable pipette channels. Independently operating multiple pipette channels 110 positioned next to each other would typically require multiple electrical cables running to each pipette channel 110 from a common controller. The embodiments described herein reduce electrical cables down to three electrical connectors 174 connecting to the manifold 102. Each pipette channel 110 is electrically connected to the electrical connectors 174. For instance, signals from the Ethernet connection are sent to each pipette channel 110 that is interchangeably mated to the manifold 102. For another example, signals from the module connection are sent to each module 120 of the plurality of pipette channels 110 that are interchangeably mated to the manifold 102. This eliminates separate cabling to each pipette channel 110. In other embodiments, separate electrical connections are provided to each pipette channel 110.

Embodiments described herein also eliminate pneumatic tubing between the solenoid valve 158 and the pipette channel 110. Typically, a separate pneumatic solenoid manifold would be mounted in close proximity to the pipette channels 110. Pneumatic tubing would connect the solenoid manifold to each pipette channel 110. In contrast, in some embodiments of the present disclosure, the solenoid valve 128 is integrated within the pipette channel 110. Each pipette channel 110 can include a solenoid valve 158. This eliminates the separate solenoid manifold and the associated pneumatic tubing running from the separate solenoid manifold to each pipette channel 110. In other embodiments of the present disclosure, the solenoid valves 158 are not located within the pipette channels 110. The solenoid valves can be located in the manifold 102. Pneumatic cross-channels similar to those described above can connect the solenoid valves in the manifold 102 to channels in the pipette channels 110 mated to the manifold 102. In these alternative embodiments, pneumatic tubing is still eliminated because pneumatic cross-channels between the manifold 102 and the modular, individually-actuatable pipette channels 110 are formed when the pipette channels 110 are mated to the manifold 102.

One advantage of some embodiments described herein includes independent operation of each pipette channel 110. In some embodiments, each pipette channel 110 can independently control the Z-movement of the pipette module 120. In some embodiments, each pipette channel 110 can independently control the aspirate and/or dispense operations of the pipette module 120. In some embodiments, each pipette module 120 is controlled independently. In some embodiments, two or more pipette modules 120 can move simultaneously, in the same or different operations. In some embodiments, each pipette channel 110 includes one or more solenoid valves 158 which selects between vacuum and pressure. In some embodiments, the second valve within the module 120 independently controls aspirate and dispense operations.

Another advantage of some embodiments described herein includes smaller overall package size. The modular pipette channels 110, 210, 310, 410 described herein can be compact. In one non-limiting example, a single pipette channel 110, 210, 310, 410 in accordance with the present disclosure is 0.689 inches (or 17.5 mm) wide in the X-direction, 7.020 inches (or 178.3 mm) deep in the Y-direction, and 13.228 inches (or 336 mm) tall in the Z-direction. Implementations of the manifold 102, 202, 302, 402 described herein can be compact. In one non-limiting example, the manifold 202 in accordance with the present disclosure is 3.8583 inches (or 98 mm) wide in the X-direction, 2.0472 inches (or 52 mm) deep in the Y-direction, and 15.1969 inches (or 386 mm) tall in the Z-direction. In one non-limiting example, the manifold 402 in accordance with the present disclosure is 3.295 inches (or 83.7 mm) wide in the X-direction, 0.8268 inches (or 21 mm) deep in the Y-direction, and 13.2283 inches (or 336 mm) tall in the Z-direction. The module 120, 220, 320, 420 can be compact. In one non-limiting example, a module 120, 220, 320, 420 in accordance with the present disclosure is 0.6693 inches (or 17 mm) wide in the X-direction, 3.0551 inches (or 77.6 mm) deep in the Y-direction, and 10.2441 inches (or 260.2 mm) tall in the Z-direction including the tip adaptor 118, 218, 318, 418. As a result of the compact nature of pipette channels, manifolds, and modules described herein, the lengths of tubing and/or wiring can be reduced. In some embodiments, faster switching between vacuum and pressure can be accomplished due to the close proximity of the solenoid valve 158 to the module 120.

Still another advantage of embodiments described herein includes the modularity of the pipette channels 110. One or more pipette channels 110 can be removed and/or replaced without removing one or more adjacent pipette channels 110. In some embodiments, there is an ability to quickly swap out individual pipette channels 110.

Advantages described above with reference to the liquid dispenser 100 illustrated in FIGS. 1B-4 are also applicable to other liquid dispensers of the present disclosure, for example liquid dispenser 1, liquid dispenser 200, liquid dispenser 300, liquid dispenser 400, and liquid dispenser 500 described in detail below.

FIGS. 5-34 show views of a liquid dispenser 200 according to another embodiment of the present disclosure. The liquid dispenser 200 can include features that are substantially similar to features described above with reference to the liquid dispenser 100. For example, the liquid dispenser 200 can include the features of a manifold 202, with a front 204, a back 206, and sides 208. The liquid dispenser 200 can include the features of one or more pipette channels 210, with a front 212, back 214, and sides 216. The liquid dispenser 200 can include the features of a module 220 with a flange 226, a coupling 228, a pipette tip 222, and a tip adapter 218. The liquid dispenser 200 can include the features of a track 230 and a base 232. The liquid dispenser 200 can include the features of a nut 234 configured to interact with a ball screw 236, a motor 238, and a bearing 240. The liquid dispenser 200 can include the features of an inlet pressure port 242, an inlet vacuum port 244, a pressure channel 246, a vacuum channel 248, a pressure cross-channel 250, a vacuum cross-channel 252, a pressure port 256, a vacuum port 257, and one or more o-rings 254. The liquid dispenser 200 can include the features of a solenoid valve 258, and one or more tubes 260, 262. The liquid dispenser 200 can include the features of a connector 266 and circuit board 268 of the of the pipette channel 210. The liquid dispenser 200 can include the features of a connector 270 and circuit board 272 of the manifold 202. The liquid dispenser 200 can include the features of a circuit board 264 of the module 220. The liquid dispenser 200 can include the features of electrical connectors 274. The liquid dispenser 200 can include the features of a ribbon cable 276, a bend 278, and a groove 280. The liquid dispenser 200 can include any of the features of the liquid dispensers described herein.

In this non-limiting embodiment, the inlet pressure port 242 and the inlet vacuum port 244 of the liquid dispenser 200 are located on the back 206 of the manifold 202. The electrical connectors 274 are also located on the back 206 of the manifold 202. Embodiments of liquid dispensers described herein that employ this configuration advantageously reduce the width of the liquid dispenser 200 along the X-direction. The circuit board 264 of the module 220 can be shorter in the Z-direction than the embodiment in FIGS. 1B-4. The circuit board 264 and the module 220 can be enclosed in a housing.

Figure 30:
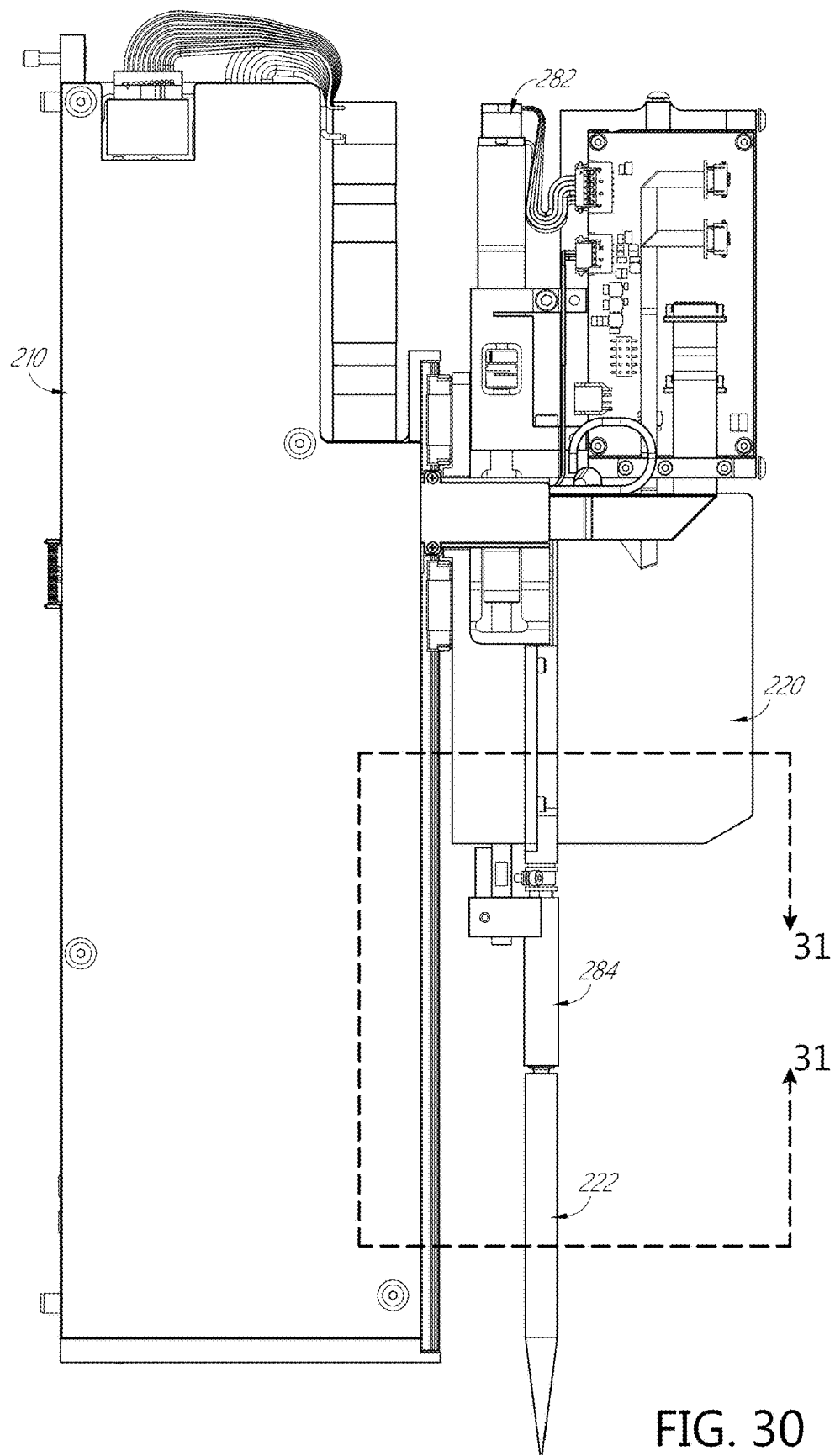
Figure 31:
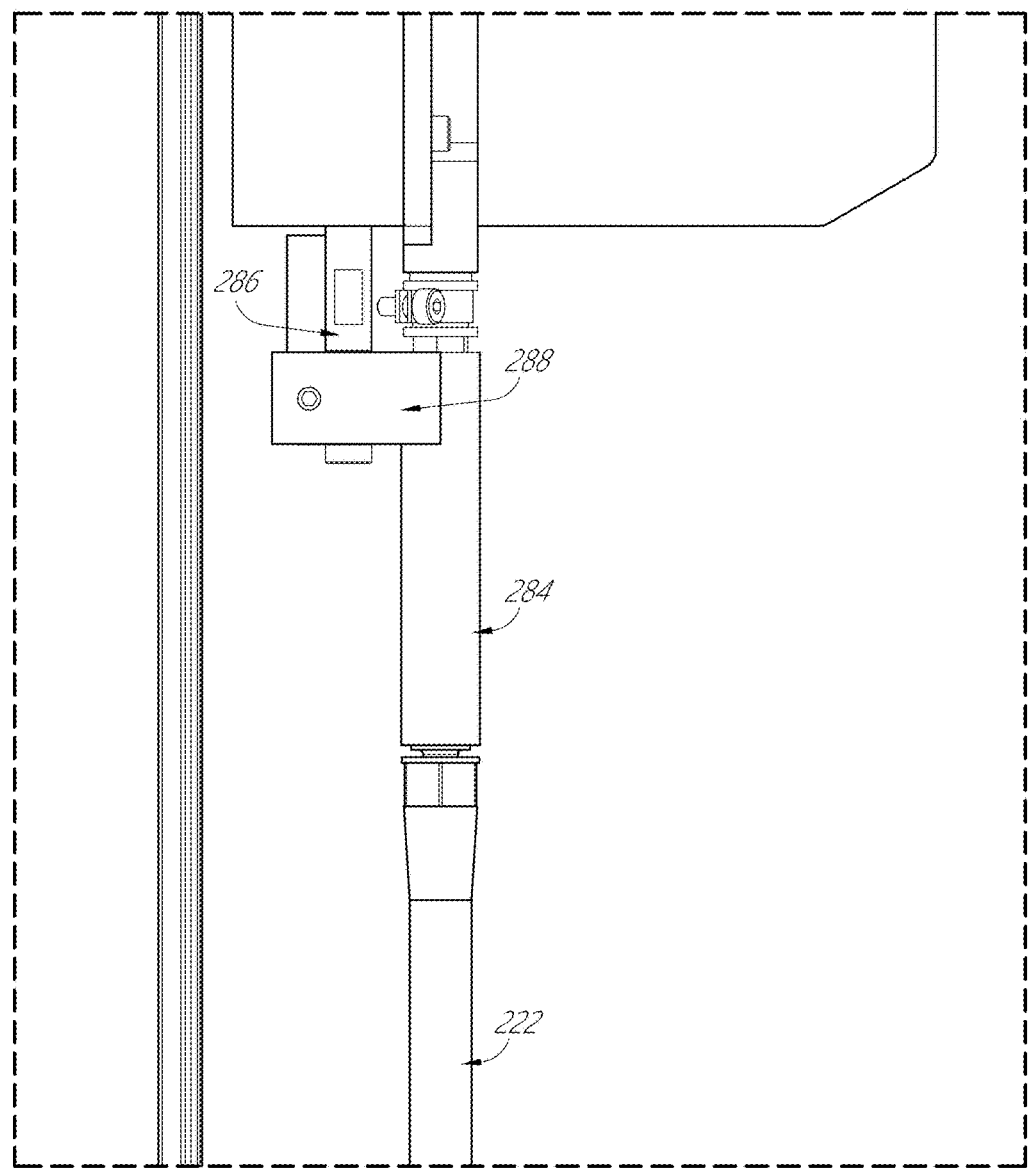
Figure 32:
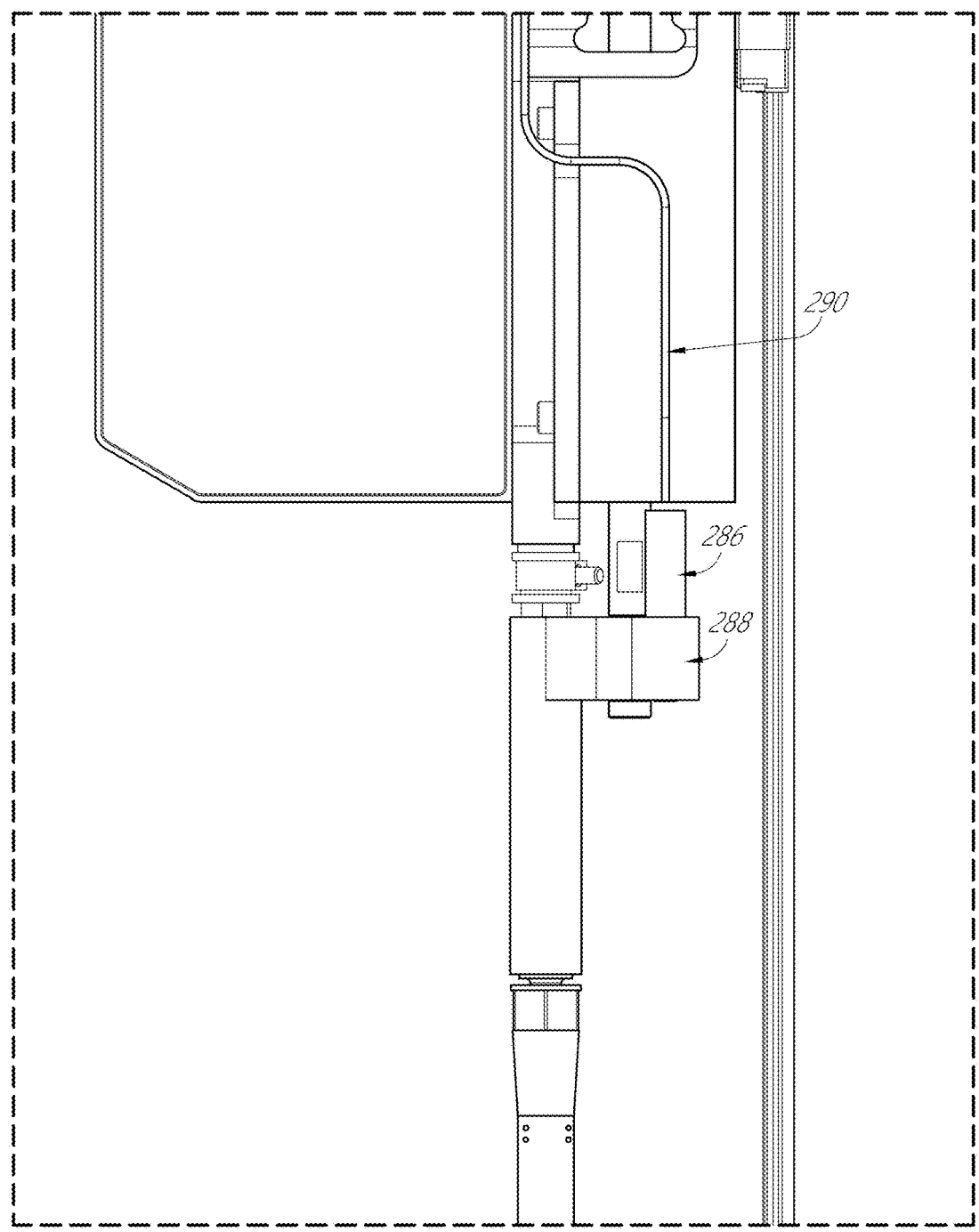
Figure 33:
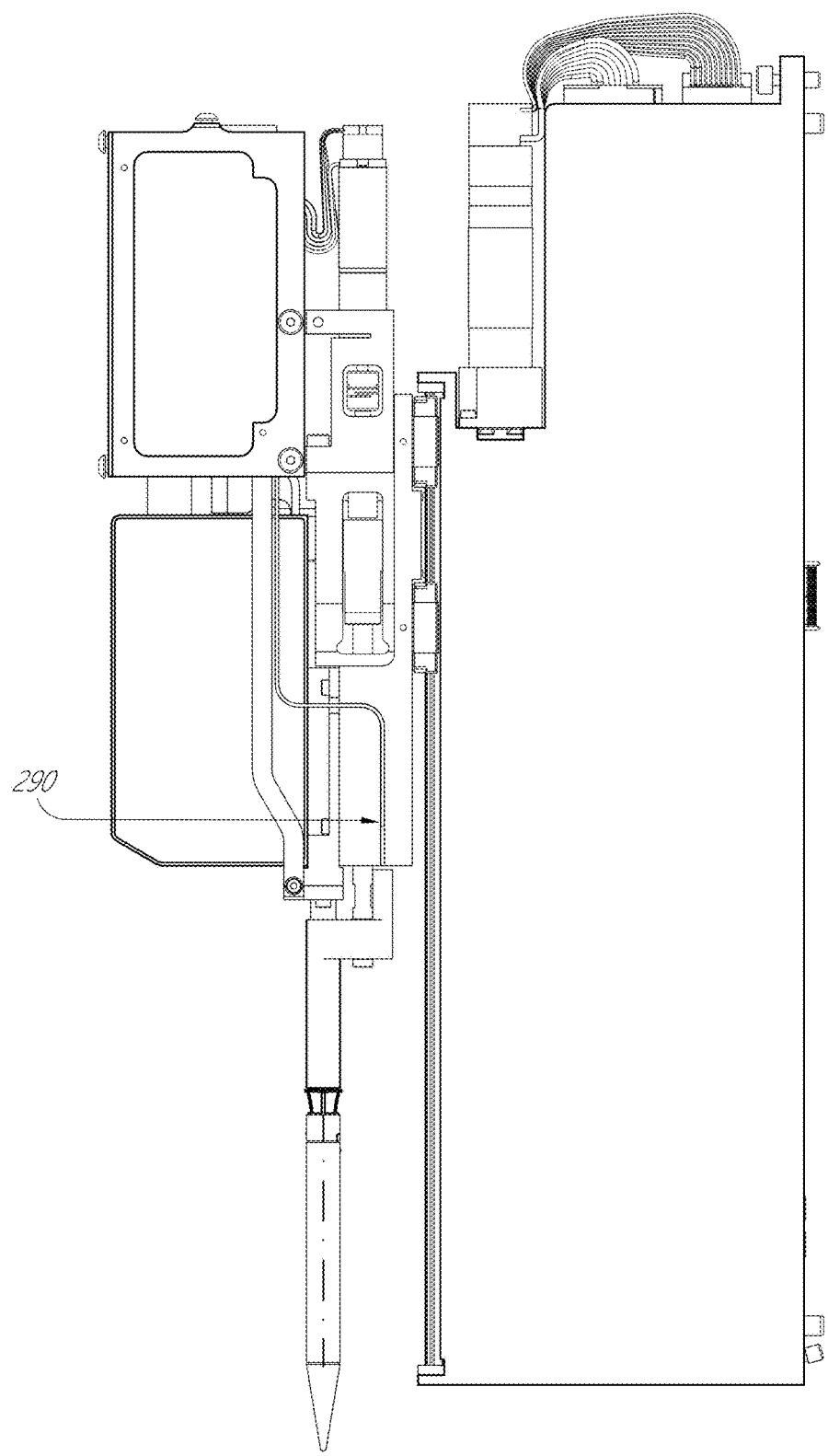

The liquid dispenser 200 can include a mechanism configured to eject a single pipette tip of a plurality of pipette tips 222, as shown in FIGS. 30-31. The liquid dispenser can include a tip eject motor 282. The tip eject motor 282 can be connected to a translating sleeve 284 that encases a portion of the tip adapter 218. The tip eject motor 282 can rotate which exerts a downward force on the sleeve 284, causing it to move in the Z-direction relative to the tip adapter 218. The downward force on the sleeve 284 overcomes a friction fit between the pipette tip 222 and the tip adapter 218 such that the pipette tip 222 is ejected or disengaged from the tip adapter 218.

The liquid dispenser 200 can include features which sense whether a pipette tip 222 is engaged with the module 220. The liquid dispenser 200 can include a sensor 286. In some embodiments, the sensor 290 is a REED sensor which senses a magnetic field. A component associated with the pipette tip 222 such as the sleeve 284 can include a magnet 286. A pipette tip 222 is engaged when the motor 238 drives the entire module 220 down to engage the pipette tip 222. The motor 238 in this implementation is the main z-axis motor. When the module 220 engages the pipette tip 222, the sleeve 284 translates upward from contact with the pipette tip 222 to allow the pipette tip 222 to engage the tip adapter 218. To engage a pipette tip 222, the module 220 translates downward in the Z-direction and pushes down on the pipette tip 222 until the pipette tip 222 snaps on, forms a friction fit, or otherwise engages the tip adapter 218. When a pipette tip 222 is loaded on the module 220 and the sleeve 284 is in this first, "engaged" position, the magnet 286 is in close proximity to the sensor 290. The pipette tip 222. can he ejected as described herein. The pipette tip 222 can become inadvertently disengaged during operation of the liquid dispenser 200. In such instances, the sleeve 284 and the magnet 286 fall downward in the Z-direction under the influence of gravity, causing the magnet 286 to be located further away from the sensor 290 than when the sleeve 284 was in the first "engaged" position before the pipette tip 222 became disengaged. The sensor 290 can indicate whether a pipette tip 222 is engaged with the sleeve 284 based on the distance between the sensor 290 and the magnet 286. The sensor 290 can determine whether a pipette tip 222 is present on the tip adapter 218.

The liquid dispenser 200 can include features which provide capacitive sense. Capacitive sensing is performed by an electrical circuit that is located on the small board (not shown) on the module 220. The board is connected via a wire, cable, or flex circuit to the tip adapter 218. When the tip adapter 218 makes contact with a liquid or other object, the circuit sees a change. The tip adapter 218 can be electrically isolated from the rest of the module 220, except for the wire going to the circuit board. The liquid dispenser 200 can include other features which determine liquid levels such as liquid levels in the pipette tip. The capacitive sense circuit can determine the Z-direction height or distance of the module 220 relative to a container containing a sample to be dispensed or aspirated. The liquid dispenser 200 can be configured to sense or receive a signal indicating, and in some cases store, information on the Z-direction height, for instance the height to associated containers. The liquid dispenser 200 can be configured to sense or receive signals indicating, and in some cases, store information on multiple heights associated with different containers. The liquid dispenser 200 can return to a stored height during aspirate and dispense operations. Other embodiments of liquid dispensers described herein, such as but not limited to liquid dispenser 100, liquid dispenser 300, liquid dispenser 400, and liquid dispenser 500, can also include capacitive sense features.

Figure 34A:
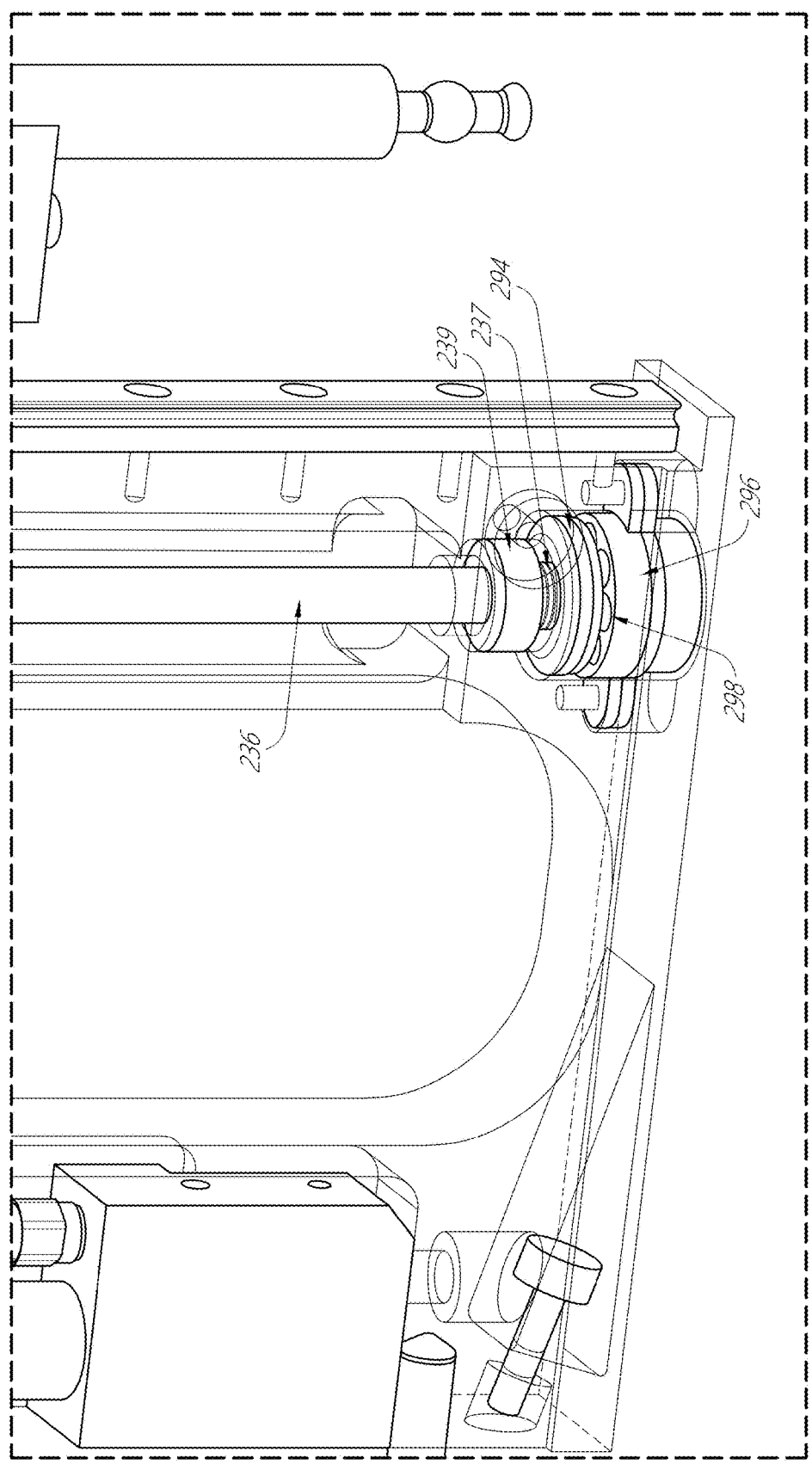
Figure 34B:
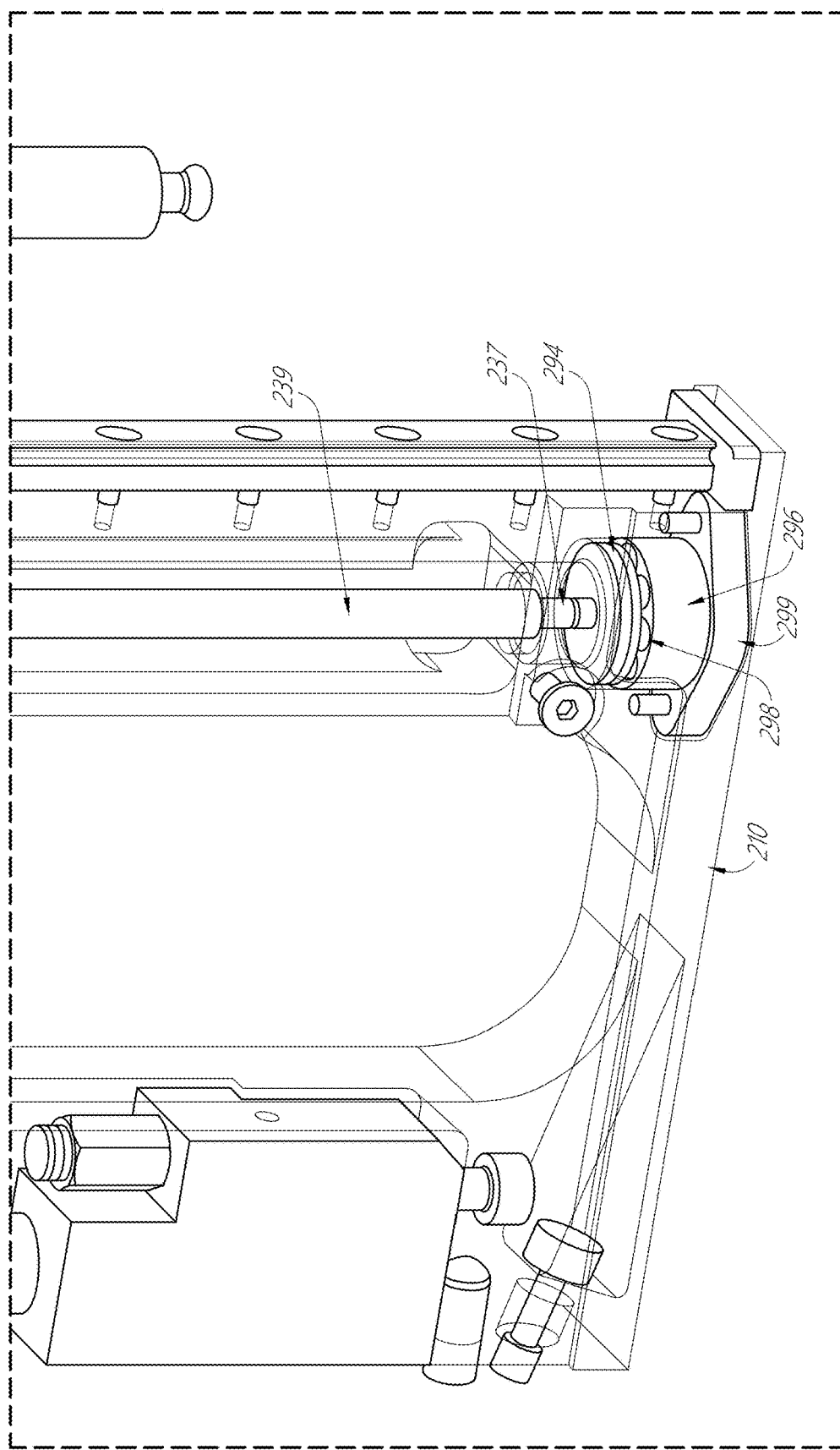

The liquid dispenser 200 can include features which provide magnetic braking such as a hysteresis brake, as shown in FIGS. 34A and 34B. The ball screw 236 can include or be coupled to a disc 294. The ball screw 236 can include a coupling portion 237. In FIG. 34A, the coupling portion 237 is threaded. The coupling portion 237 can be inserted into a threaded bore of the disc 294. The coupling portion 237 can be inserted into a threaded bore of a bearing 239. The bearing 239 can facilitate alignment between the ball screw 236 and the disc 296. In FIG. 34B, the coupling portion 237 includes one or more grooves. In some embodiments, the disc 294 includes one or more projections designed to engage the grooves. In some embodiments, the disc 294 includes a mechanism designed to couple the coupling portion 237 with the disc 294. Other configurations of coupling the ball screw 236 and the disc 294 are contemplated. In some embodiments, the ball screw 236 and the disc 294 are rotational coupled such that rotation of the ball screw 236 causes rotation of the disc 294.

The bearing 239 or other portion of the pipette channel 210 can include a disc 296. The disc 296 can include one or more magnets 298. In some embodiments, a plurality of magnets 298 in the disc 296 can all have the same polarity. In some embodiments, the magnets 298 in the disc 296 have the opposite polarity. In some embodiments, the magnets 298 in the disc 296 have alternating polarity. In some embodiments, adjacent magnets 298 can have opposite polarity. The disc 294 can be a hysteresis disc. In some embodiments, only the disc 296 includes magnets 298. During rotation of the ball screw 236 under the influence of the motor 238, the motor 238 overcomes a magnetic force created by the magnetic interaction of the discs 294, 296. When the motor 238 stops, the magnets 298 in the disc 296 are attracted to disc 294. The magnetic force is sufficient to apply a torque to the ball screw 236 to reduce and/or prevent rotation of the ball screw 236. The magnetic force can be sufficient to reduce and/or prevent the free-fall of the coupling 228 along the track 230 in the event of loss of electrical power to the pipette channel 210. Other embodiments of liquid dispensers described herein, such as but not limited to liquid dispenser 100, liquid dispenser 300, liquid dispenser 400, and liquid dispenser 500, can also include magnetic braking features. FIG. 34B shows a modified design in which the disc 296 can be coupled to or integrally formed with a block 299. The block 299 can anchor the disc 296 to the pipette channel 210. The block 299 can include an attachment section for coupling with pegs or fasteners. The attachment section can include one or more curved corners. The block 299 can be polygonal or generally polygonal. In the illustrated embodiment, the block 299 is diamond shaped with rounded corners.

Figure 34C:
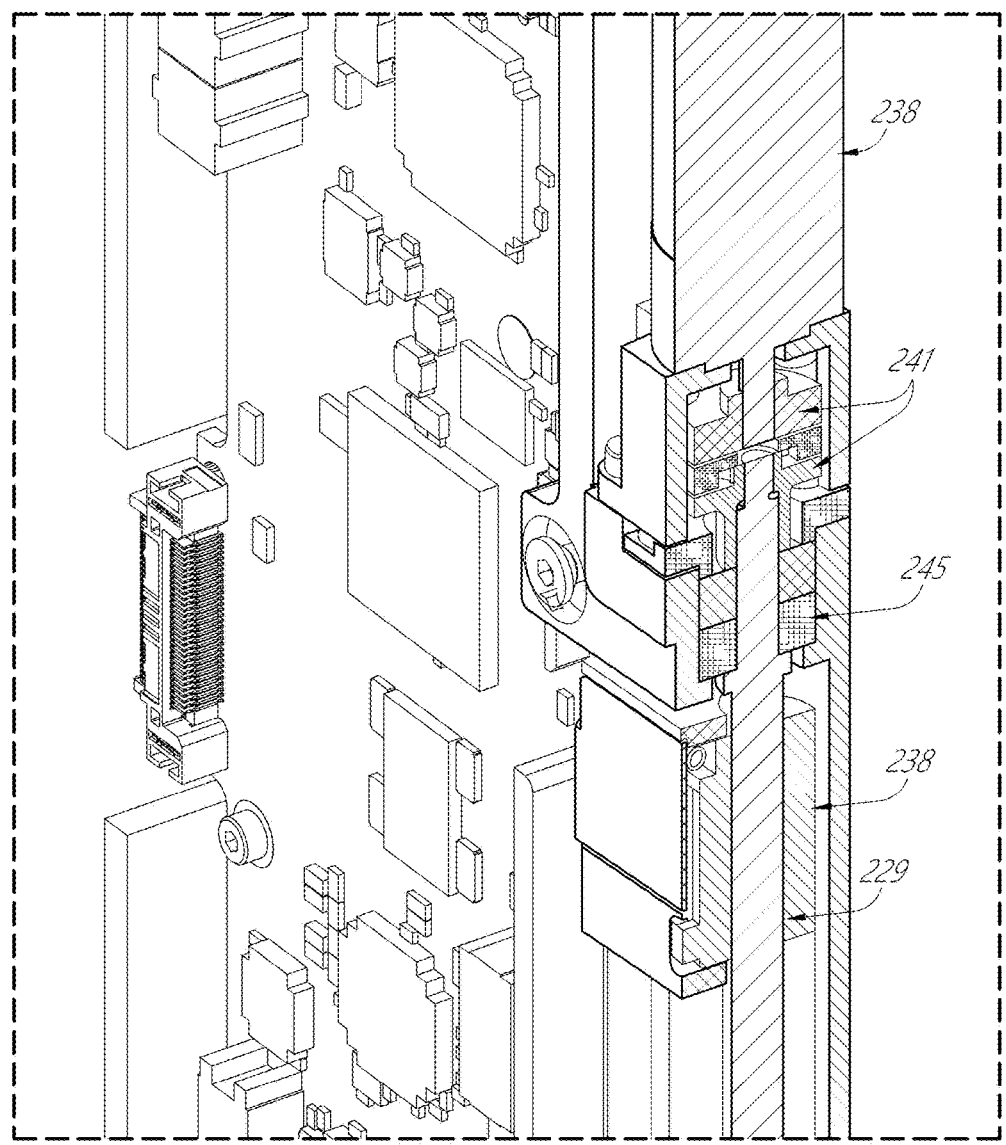
Figure 34D:
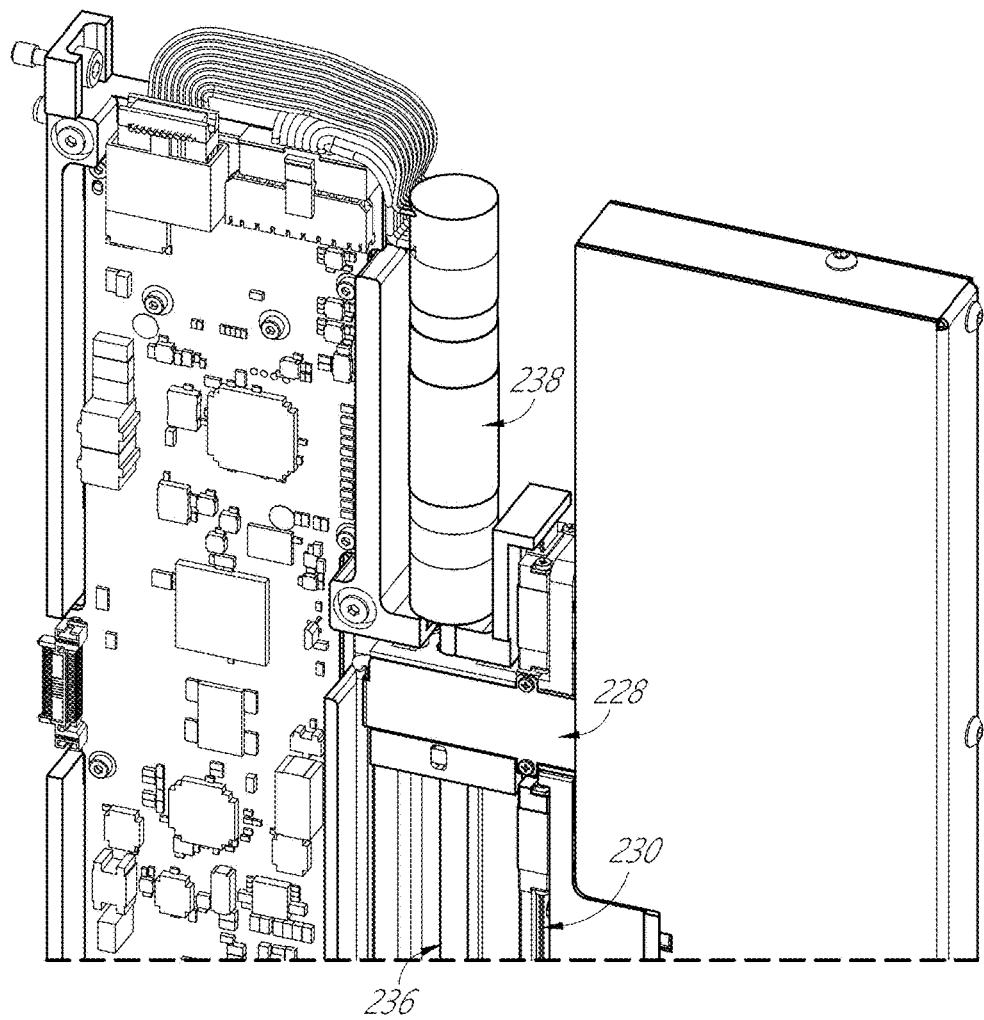

FIGS. 34C and 34D show other features of the liquid dispenser. The ball screw 236 can be rotated with a motor 238. The coupling 228 can include a nut which includes a bore 229. In some embodiments, a plurality of ball bearings (not shown) are arranged around the bore 229 inside the nut, which reduce friction when interacting with the ball screw. The ball bearing s can rotate within a helical groove of the ball screw 236. As one example, as the ball screw 236 rotates, a ball bearing travels around the ball screw 236 within the groove of the ball screw 236 and a groove in the nut. When the ball bearing reaches the top of the nut, the ball bearing is fed down a channel in the coupling 228 (not shown) toward the bottom of the nut. The ball screw 236 can be rotated in the opposite direction such that the ball bearing is fed up the channel in the coupling 228. FIGS. 34C and 34D show how the coupling 228 is attached to the ball screw 236. FIGS. 34C and 34D also show how the motor 238 and the ball screw 236 are coupled. In some embodiments, the pipette channel 210 can include an integrated ball screw assembly which can include one or more of the motor 238, an encoder, and the ball screw 236. some embodiments, the motor 238 and the encoder are coupled as an assembly or integrally formed.

FIG. 34C shows a shaft coupling 241. The shaft coupling 241 couples the shaft of the ball screw 236 and the shaft of the motor 238. The shaft coupling 241 can allow for a degree of misalignment between the ball screw 236 and the motor 238. The shaft coupling 241 accounts for misalignment between the ball screw 236 and the shaft of the motor 238. The shaft coupling 241 can tolerate some angular misalignment. The shaft coupling 241 can be designed to handle axial misalignment between the bail screw 236 and the motor 238. In some embodiments, the shaft coupling 241 can allow a misalignment of 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, between 0-5 degrees, between 0-10 degrees, etc.

The liquid dispenser 200 can include one or more bearings 245. The bearings 245 can support the end of the ball screw 236. The bearings 245 can include a matched set of angular contact bearings. The bearings 245 can support the ball screw 236 in both the radial and axial directions. In some embodiments, the bearing 245 allows the ball screw to rotate without translation. In some embodiments, the bearing 245 reduces axial misalignment between the motor 238 and the ball screw 236.

As described herein, the coupling 228 can include a portion that interacts with the ball screw 236 and a portion that interacts with the track 230. FIG. 34D shows an embodiment of these two portions. In some embodiments, the coupling 228 can be a floating coupling that allows the connection between the track 230 and the ball screw 236 to self-adjust or float. The floating coupling provides flexibility to prevent binding if the track 230 and the ball screw 236 are not perfectly aligned. In some embodiments, a bearing supports the ball screw axially and radially. In some embodiments, one or more bearings are integrated with the motor 238. In other embodiments, one or more bearings are separate components from the motor 238.

Embodiments of the magnetic brake described herein advantageously limit undesirable movement of the pipette tip. Another advantage is that the magnetic brake limits damage to the pipette tip. In addition, embodiments of the magnetic brake described herein advantageously provide greater drive accuracy. Still another advantage is that the magnetic brake allows controlled movement of the pipette tip relative to a container. In some embodiments, the magnetic brake functions to limit movement of the pipette tip. In some embodiments, the force produced by the magnetic brake limits downward or upward movement of the module 220 when the motor 238 stops.

FIGS. 35-55 show views of a liquid dispenser 300 according to another embodiment of the present disclosure. The liquid dispenser 300 can include features that are substantially similar to features described above with reference to the liquid dispenser 100 and the liquid dispenser 200. For example, the liquid dispenser 300 can include the features of a manifold 302, with a front 304, a back 306, and sides 308. The liquid dispenser 300 can include the features of one or more pipette channels 310, with a front 312, back 314, and sides 316. The liquid dispenser 300 can include the features of a module 320 with a flange 326, a coupling 328, a pipette tip (not shown but similar to pipette tips 122, 222), and a tip adapter 318. The liquid dispenser 300 can include the features of a track 330 and a base 332. The liquid dispenser 300 can include the features of a nut 334 configured to interact with a ball screw 336, a motor 338, and a bearing 340. The liquid dispenser 300 can include the features of an inlet pressure port 342, an inlet vacuum port 344, a pressure channel 346, a vacuum channel 348, a pressure cross-channel 350, a vacuum cross-channel 352, a pressure port 356, a vacuum port 357, and one or more o-rings 354. The liquid dispenser 300 can include the features of a solenoid valve 358, and one or more tubes 360, 362. The liquid dispenser 300 can include the features of a connector 366 and circuit board 368 of the of the pipette channel 310. The liquid dispenser 300 can include the features of a connector 370 and circuit board 372 of the manifold 302. The liquid dispenser 300 can include the features of a circuit board 364 of the module 320. The liquid dispenser 300 can include the features of electrical connectors 374. The liquid dispenser 300 can include the features of a ribbon cable 376, a bend 378, and a groove 380. The liquid dispenser 300 can include features that eject the pipette tip including a tip eject motor 382 and a sleeve 384. The liquid dispenser 300 can include any of the features of the liquid dispensers described herein.

In this non-limiting embodiment, the pipette module 320 is mounted adjacent to a side 316 of the pipette channel 310 along the X-axis of the liquid dispenser 300. Embodiments of liquid dispensers described herein that employ this configuration advantageously decrease the depth of the pipette channel 310 along the Y-axis. Embodiments of liquid dispensers described herein that employ this configuration can increase the width of the pipette channel 310 along the X-axis. The back 314 of the pipette channel 310 is configured to mate with the front 304 of the manifold 302, as described herein.

Figure 39:
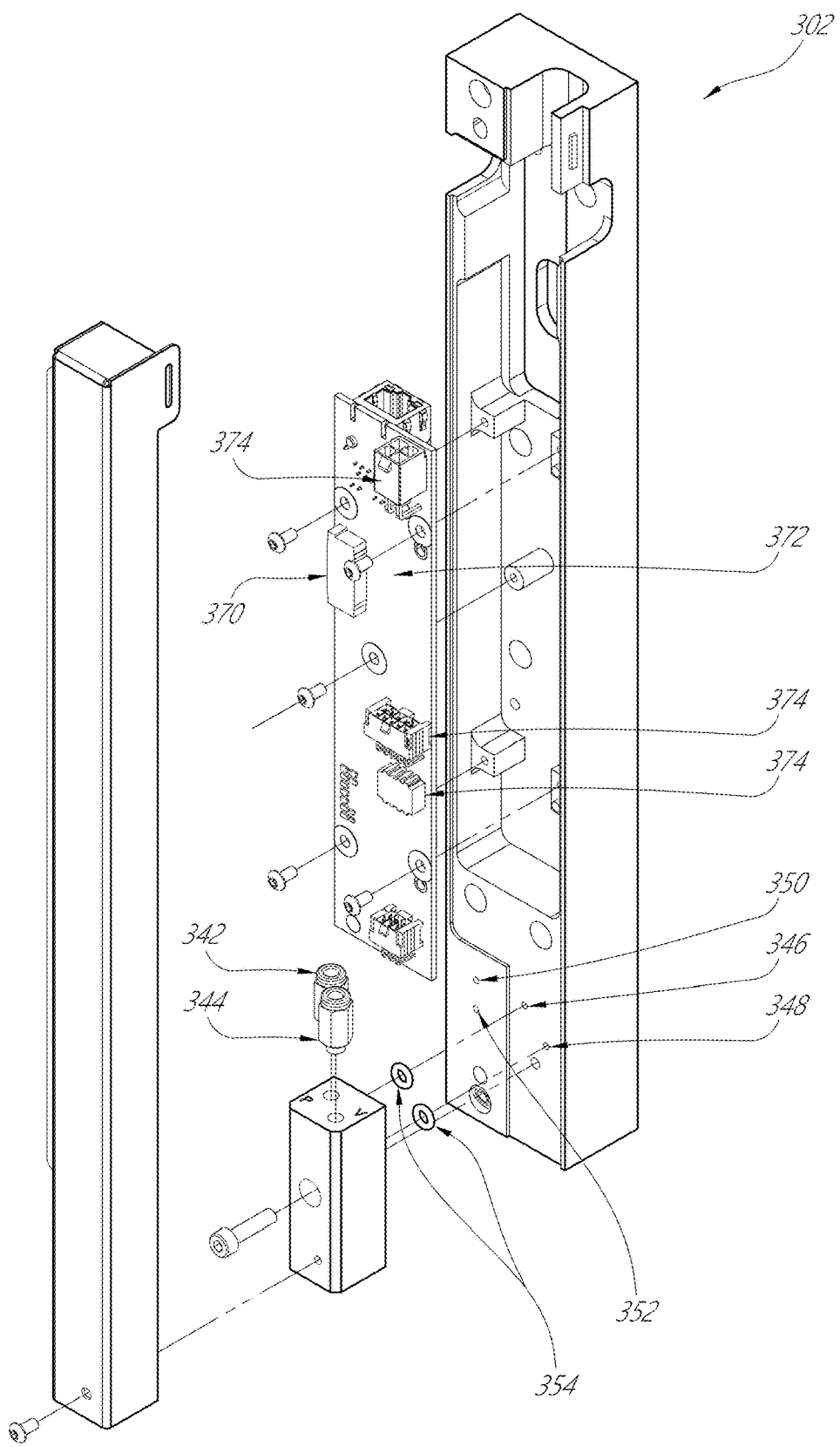
Figure 40:
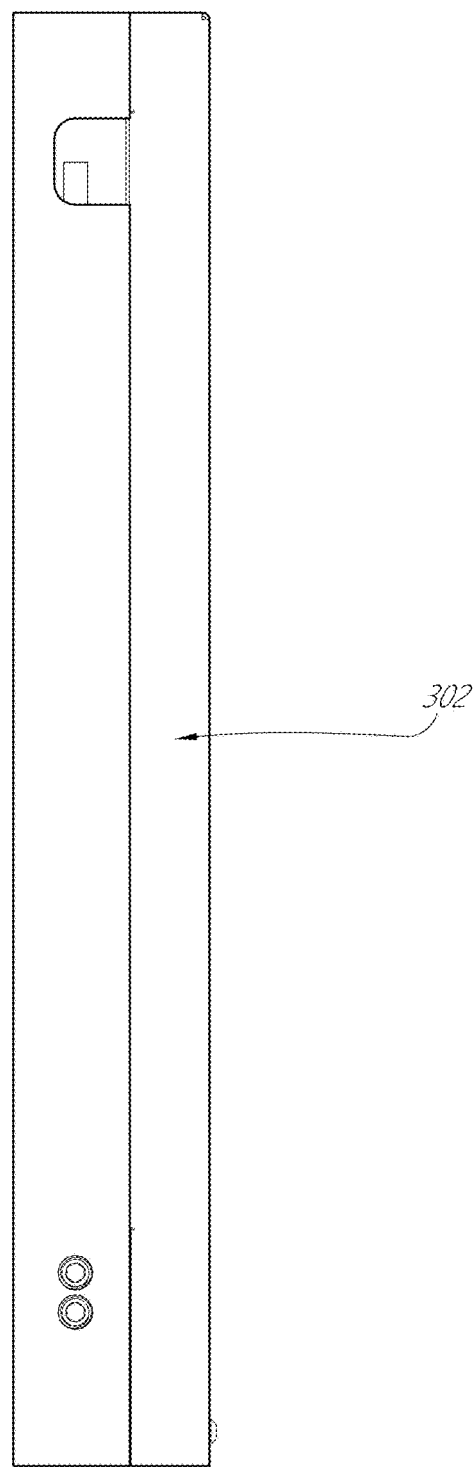
Figure 41:
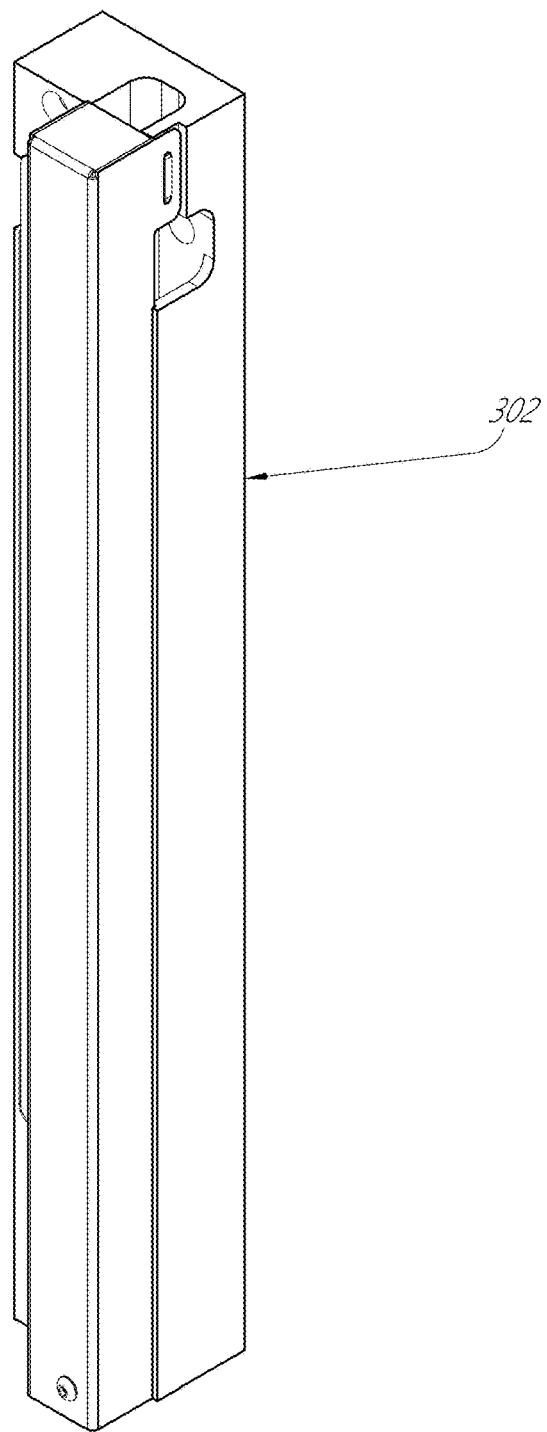
Figure 42:
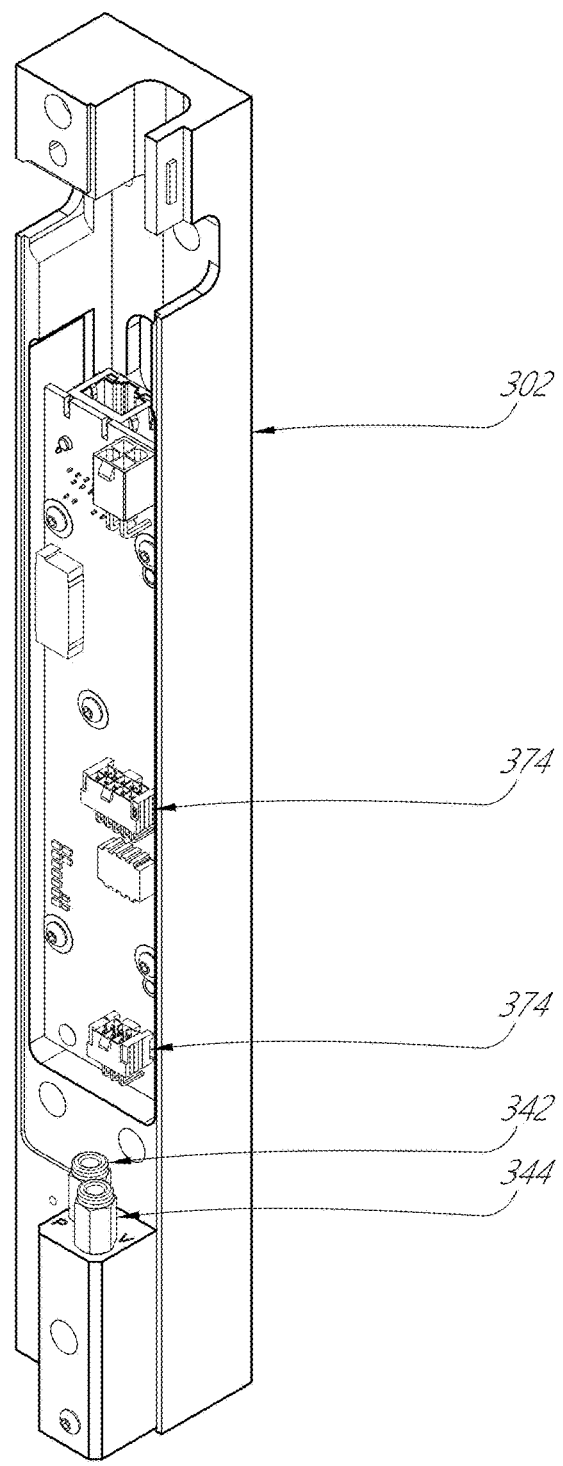
Figure 43:
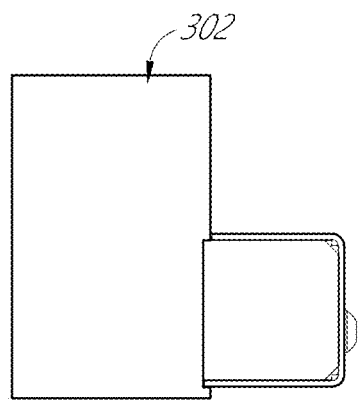
Figure 44:
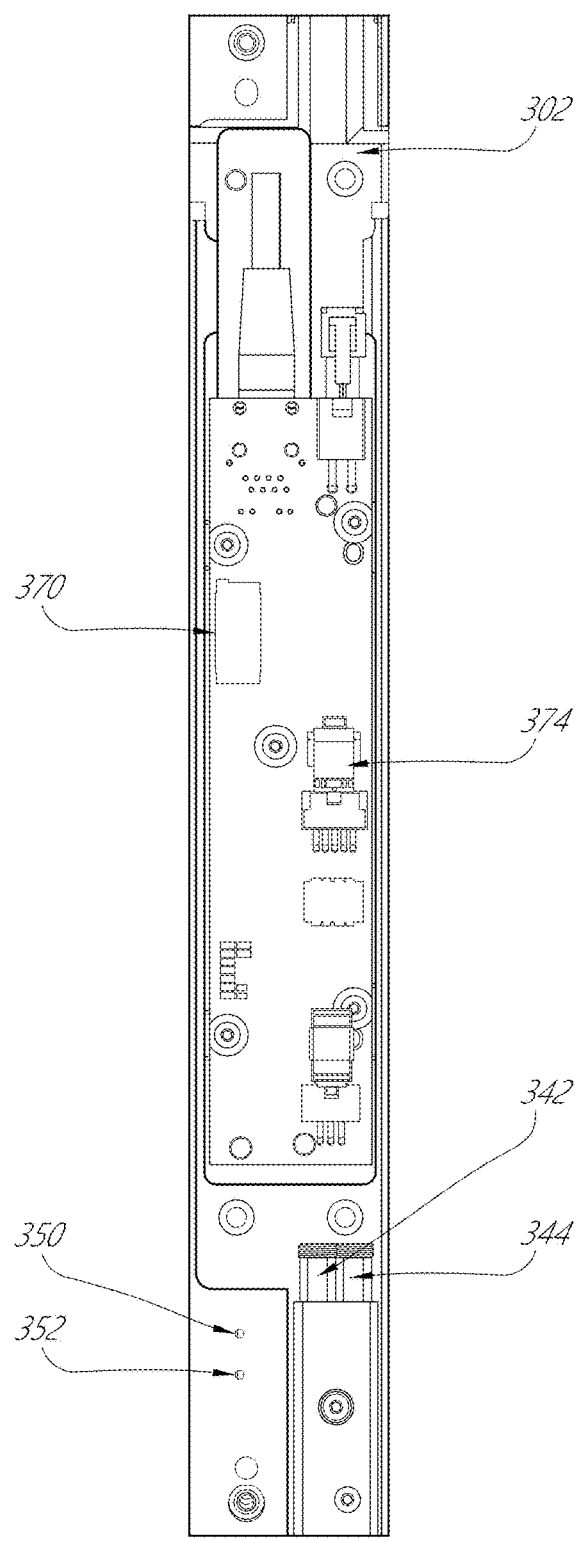
Figure 45:
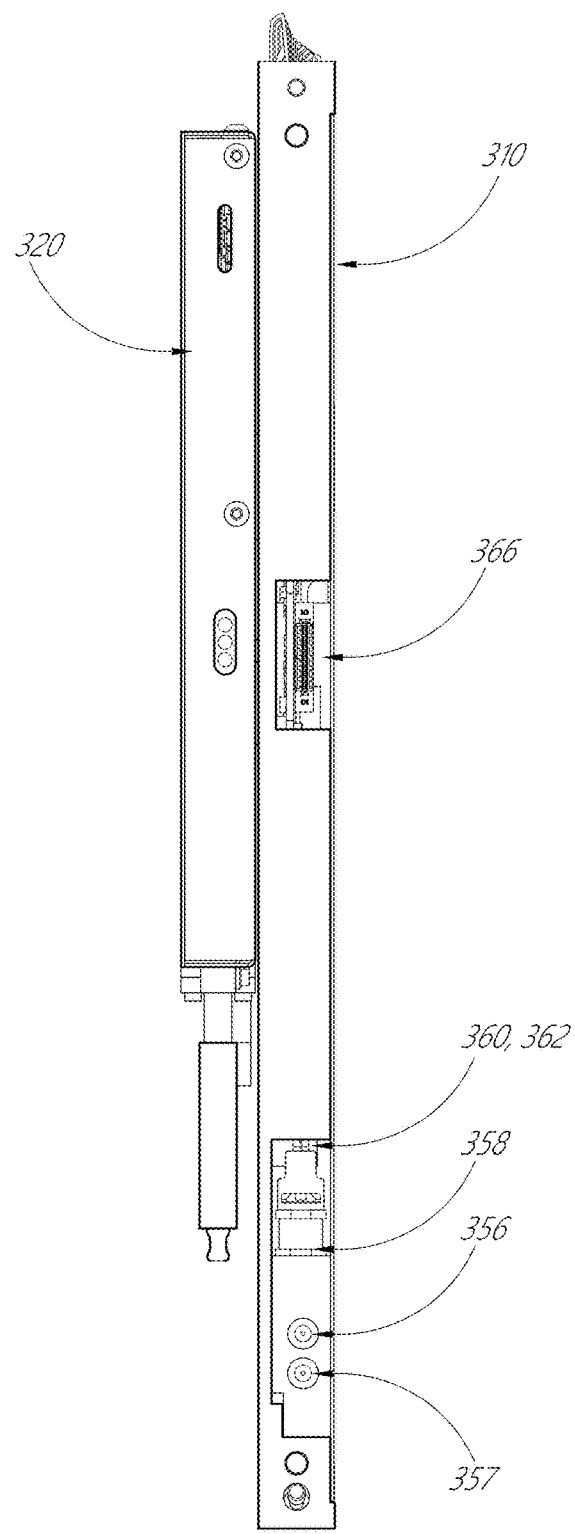
Figure 46:
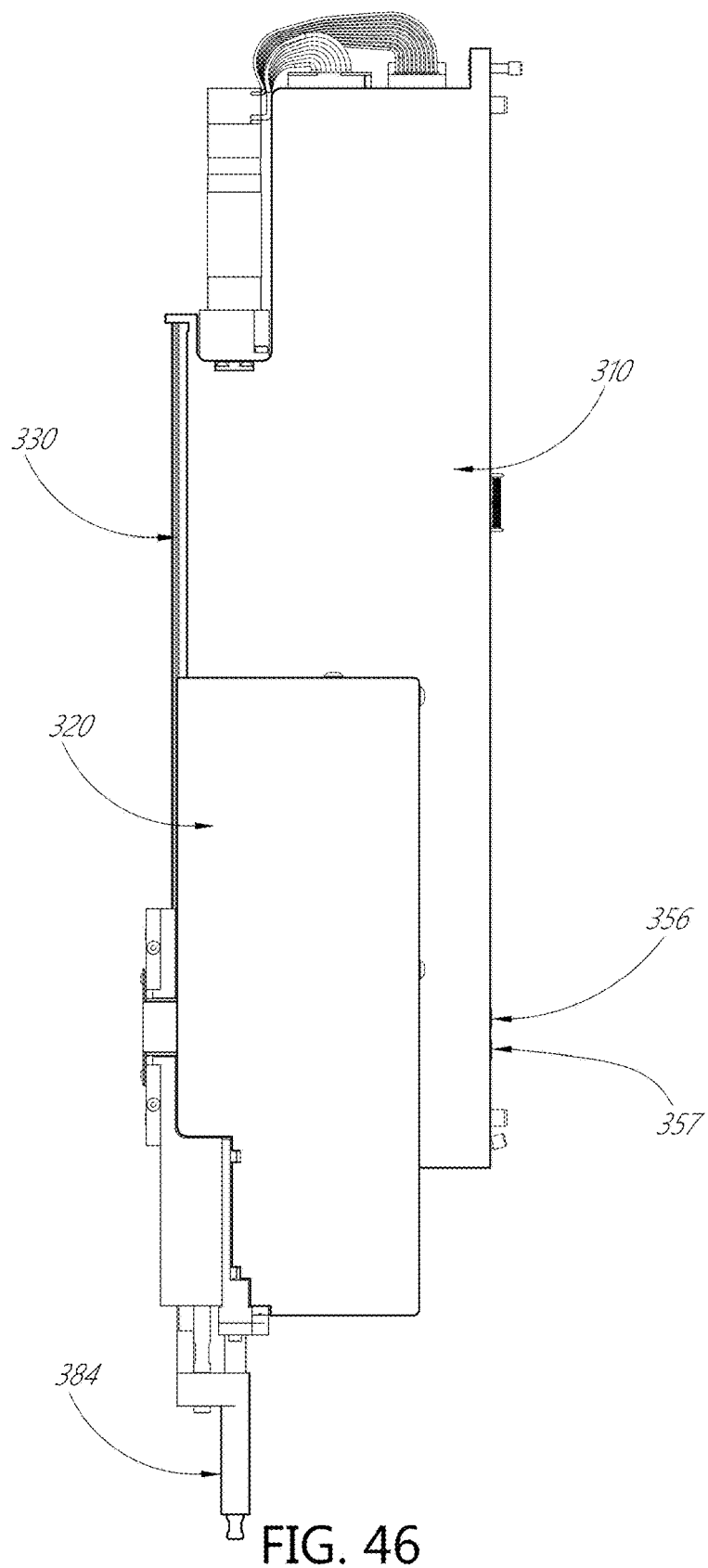
Figure 47:
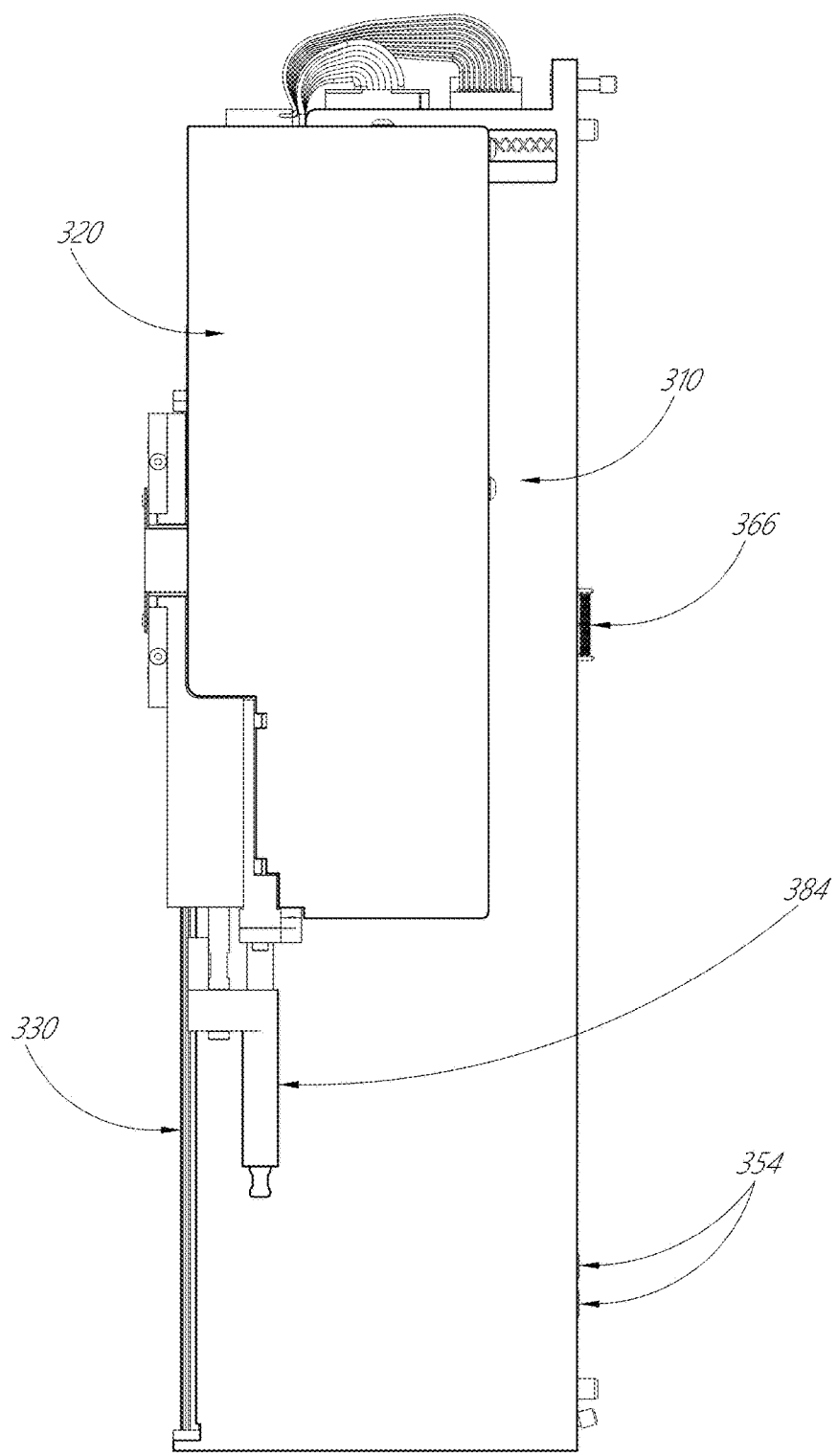
Figure 48:
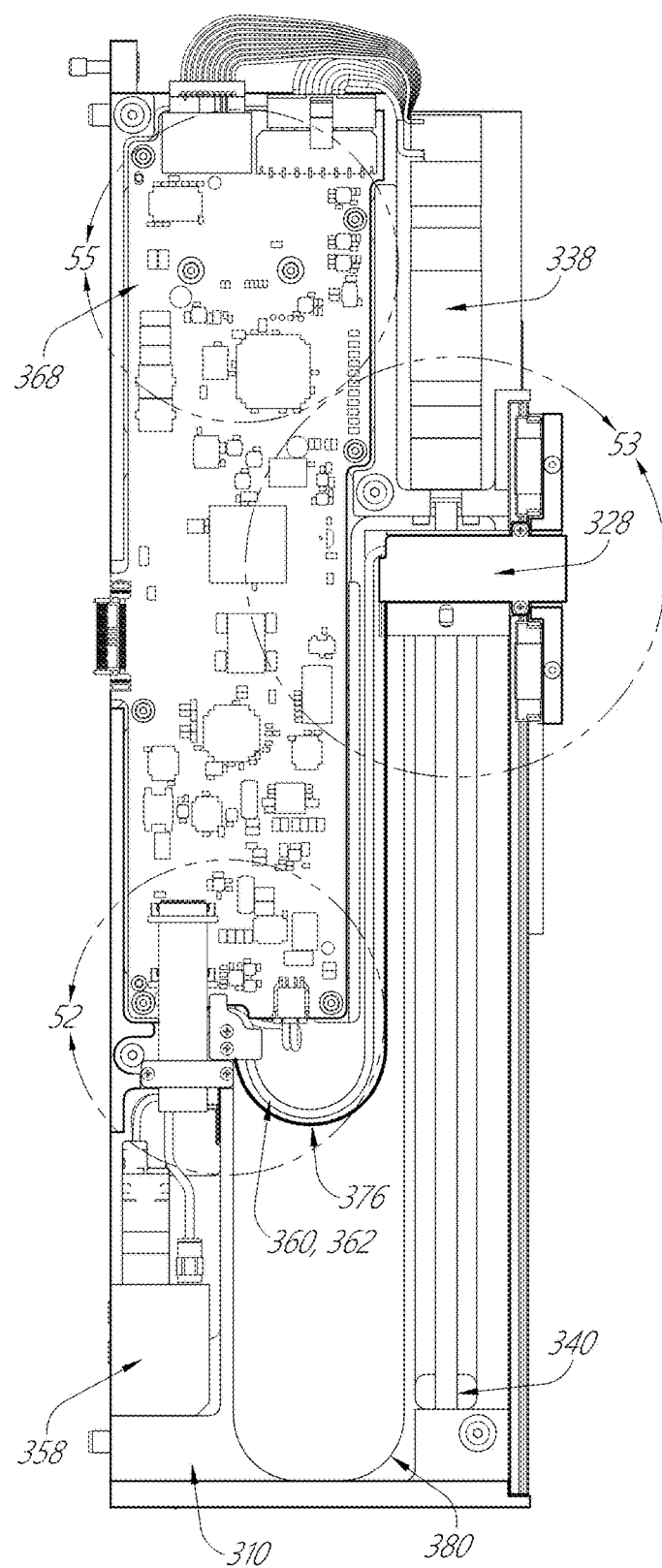
Figure 49:
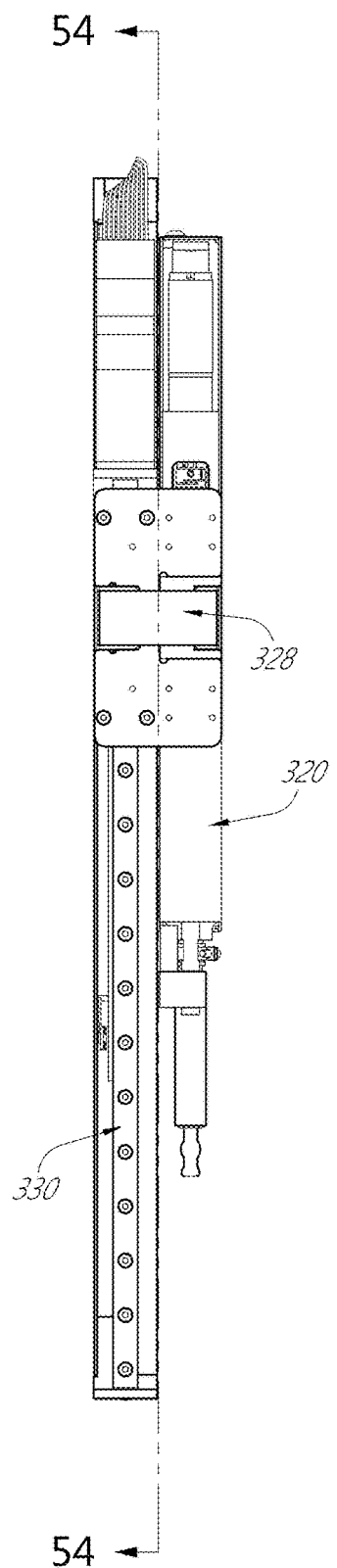
Figure 50:
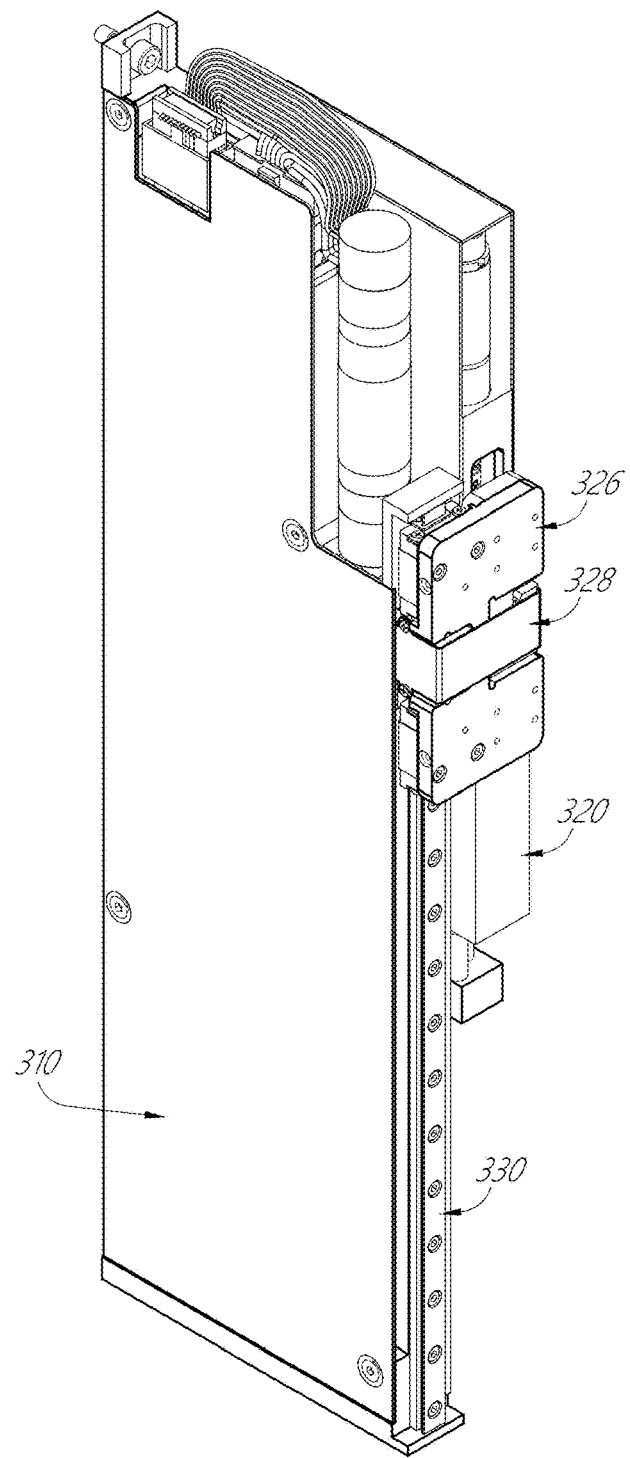
Figure 51:
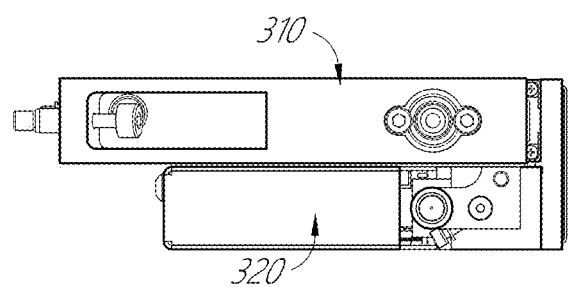
Figure 52:
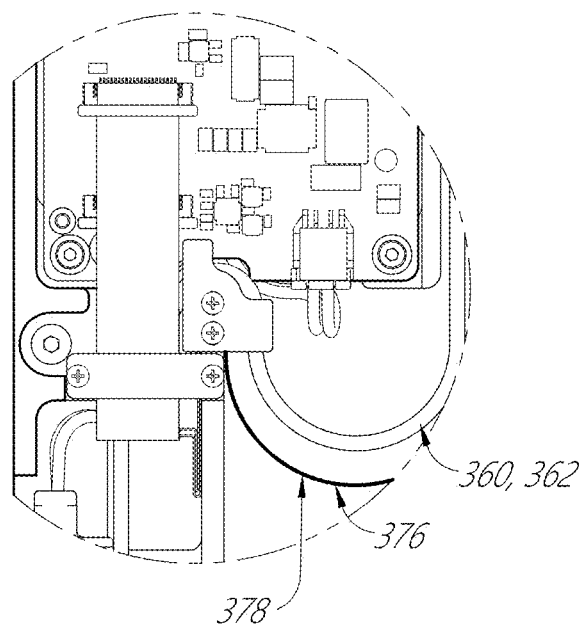
Figure 53:
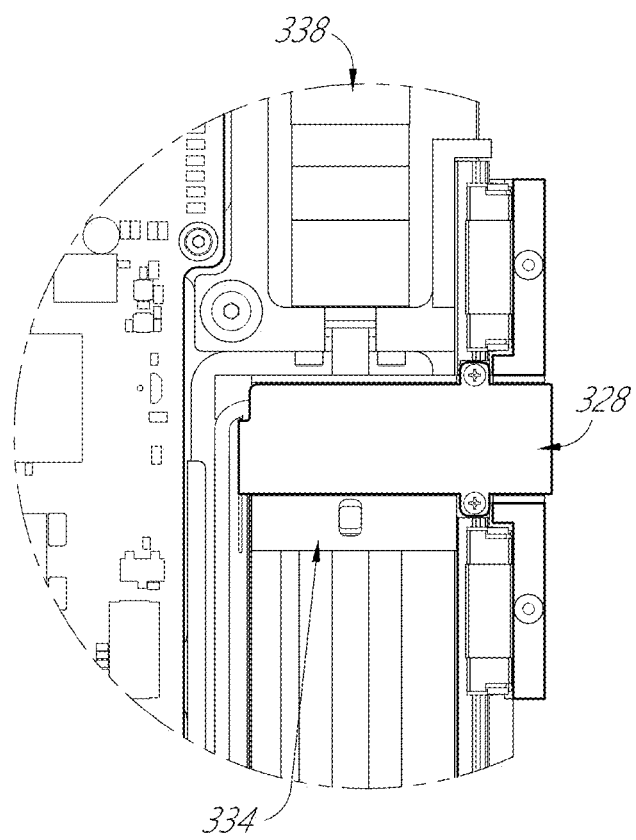
Figure 54:
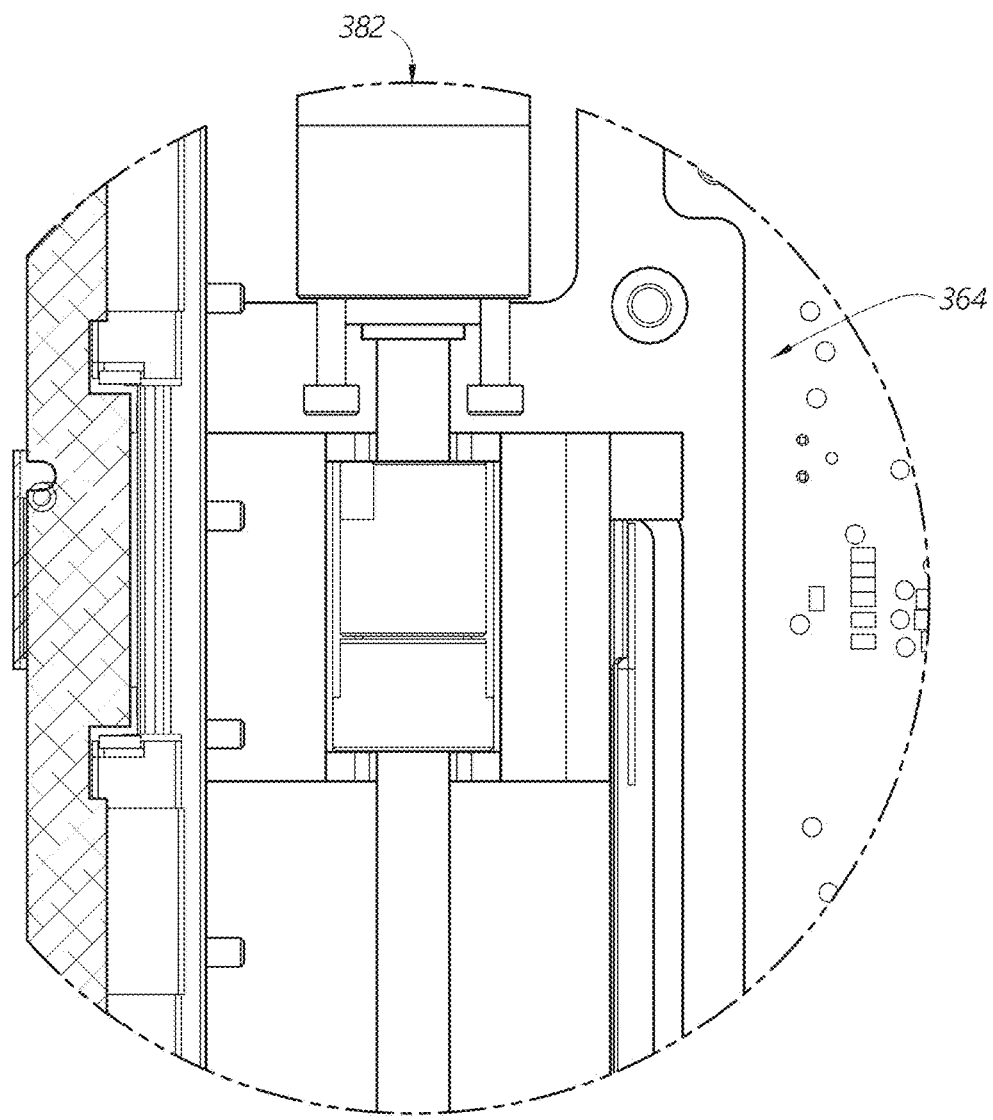
Figure 55:
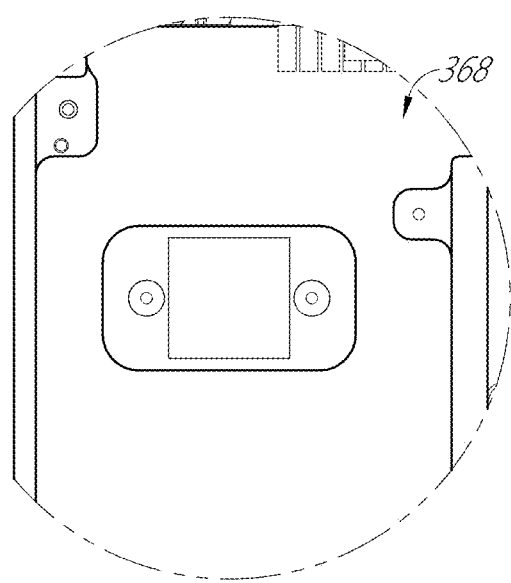

FIG. 39 shows an exploded view of the manifold 302. The aspirate and dispense operations of the module 320 can be controlled, in part, by application of gas pressure or gas under vacuum. The manifold 302 can include the inlet pressure port 342. The manifold 302 can include the inlet vacuum port 344. The inlet pressure port 342 can be located on the front 312 of the manifold 302. The inlet vacuum port 344 can be located on the front 312 of the manifold 302. The inlet pressure port 342 and the inlet vacuum port 344 can be enclosed in a housing as shown. The electrical connectors 374 can be located on the front 312 of the manifold 302. The electrical connectors 374 can also be enclosed in a housing as shown.

The pressure channel 346 and the vacuum channel 348 within the manifold 302 can be non-linear, for instance, having one or more bends or curves along the length of the channel, such as but not limited to an L-shaped or U-shaped channel. The pressure cross-channel 350 and the vacuum cross-channel 352 within the manifold 302 can be non-linear. The pressure channel 346 and the vacuum channel 348 can extend from the inlet pressure port 342 and inlet vacuum port 344 to the pressure cross-channel 350 and the vacuum cross-channel 352, respectively. The pressure channel 346, the vacuum channel 348, the pressure cross-channel 350 and the vacuum cross-channel 352 can be designed in any way in order to align with the pressure port 356 and the vacuum port 357 of the pipette channel 310.

The manifold 302 is configured to accept one or more pipette channels 310. The liquid dispenser 300 in the illustrated embodiment is configured to accept one pipette channel 310, but other configurations are contemplated. The pipette channel 310 can be fixed in position to the manifold 302 during operation of the pipette module 320, for instance by the pegs 324. The inlet pressure port 342 can supply gas under pressure to one pressure cross-channel 350. The inlet vacuum port 344 can supply gas under vacuum to one vacuum cross-channel 352.

The pipette module 320 is mounted adjacent to a side 316 of the pipette channel 310. The flange 326 and the coupling 328 can be shaped to accommodate this configuration. In some embodiments, the flange 326 and/or the coupling 328 are perpendicular to the module 320. The flange 326 can be fixedly attached to a coupling 328. The coupling 328 is movable along a track 330. The movement of the coupling 328 causes movement of the module 320 in the Z-direction relative to the track 330. The track 330 is fixedly attached to a base 332 of the pipette channel 310. The base 332 of the pipette channel is stationary relative to manifold 302. The movement of the coupling 328 causes movement of the module 320 in the Z-direction relative to the base 332 of the pipette channel 310 and the manifold 302. The coupling 328 can interact with a ball screw 336, as described herein with reference to other embodiments of the present disclosure.

Figure 56:
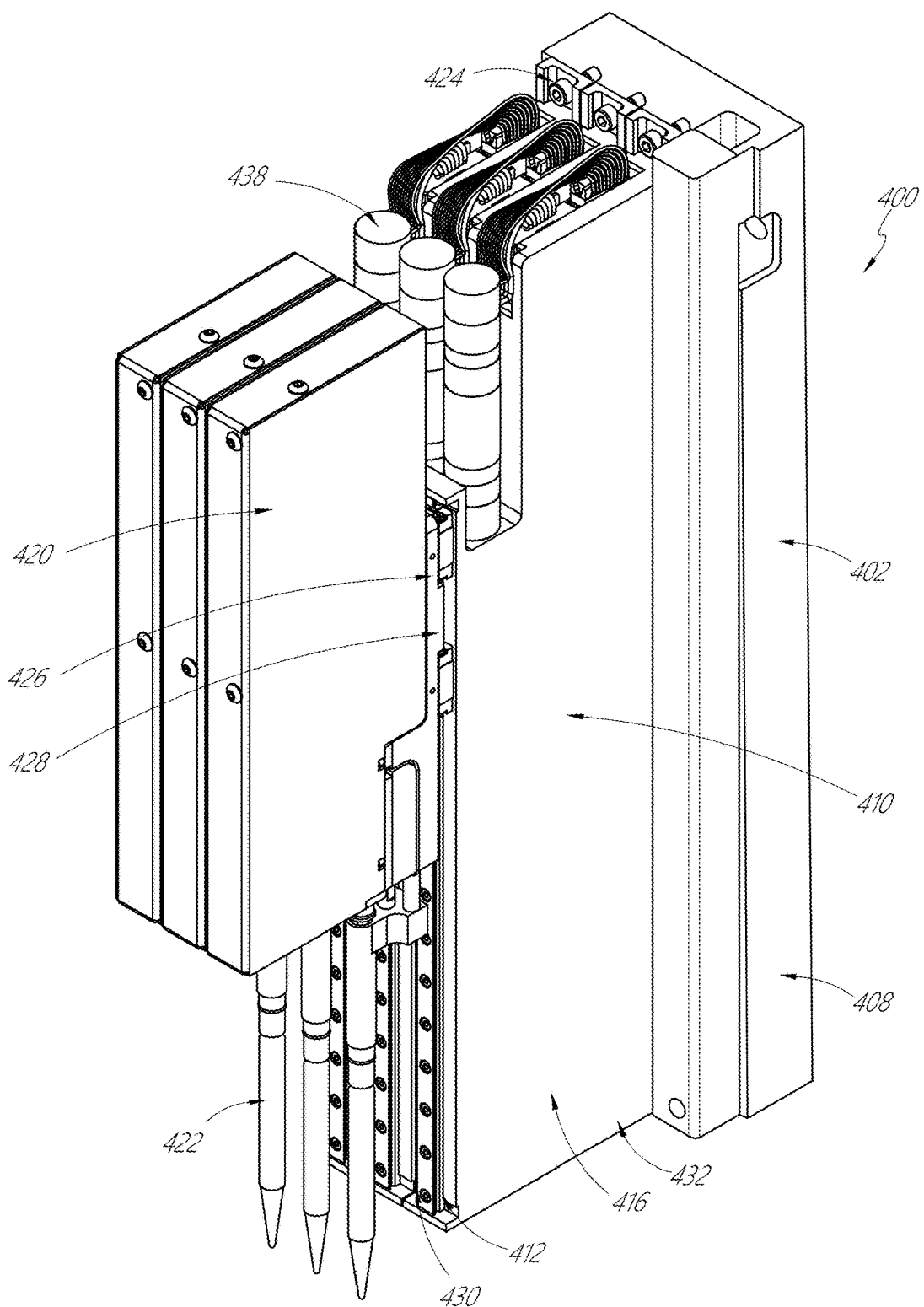
FIGS. 56-57 show views of a liquid dispenser according to a fifth embodiment.
Figure 57:
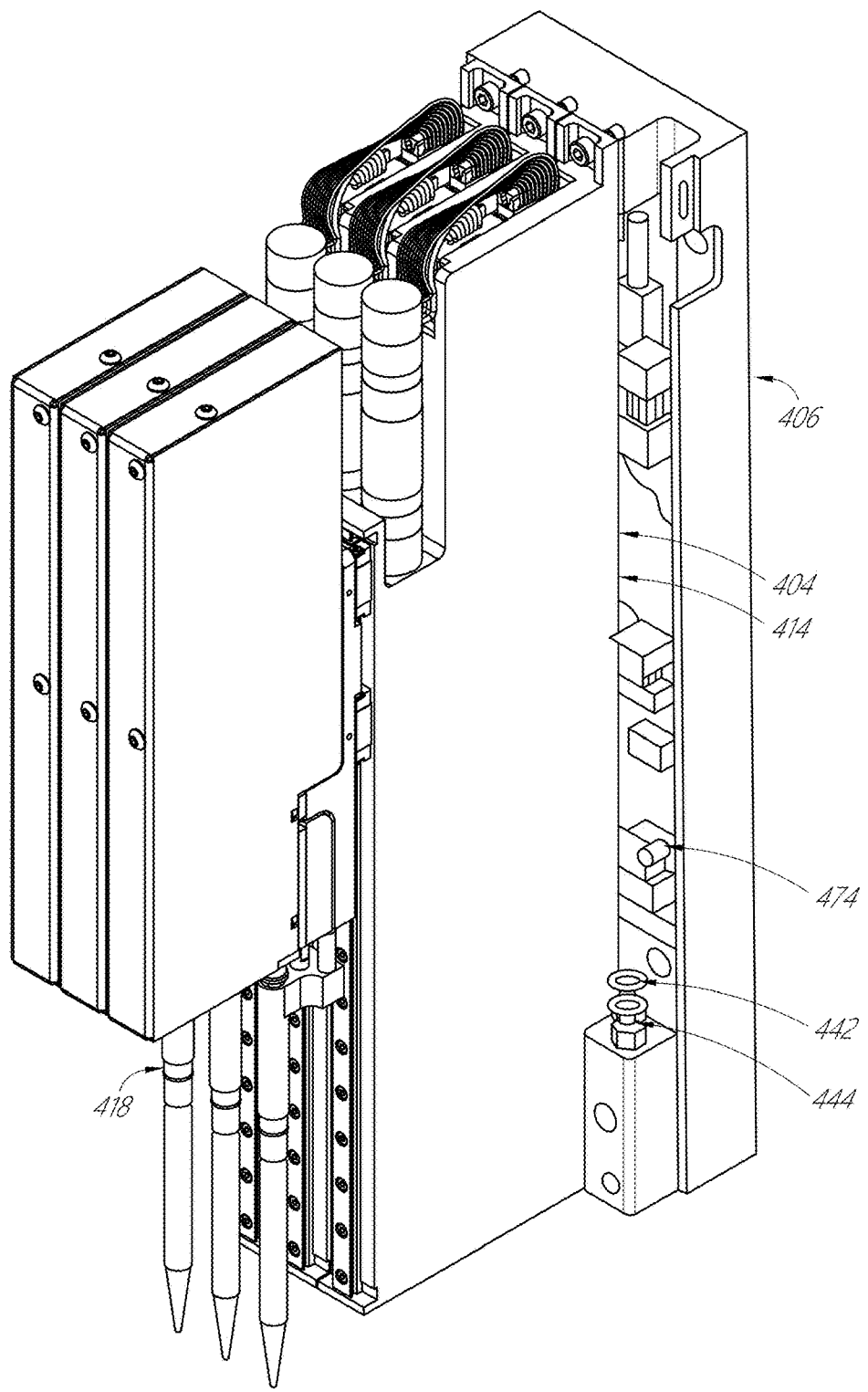

FIGS. 56-57 show views of a liquid dispenser 400 according to another embodiment of the present disclosure. The liquid dispenser 400 can include features that are substantially similar to features described above with reference to the liquid dispenser 100, the liquid dispenser 200, and the liquid dispenser 300. For example, the liquid dispenser 400 can include the features of a manifold 402, with a front 404, a back 406, and sides 408. The liquid dispenser 400 can include the features of one or more pipette channels 410, with a front 412, back 414, and sides 416. The liquid dispenser 400 can include the features of a module 420 with a flange 426, a coupling 428, a pipette tip 422, and a tip adapter 418. The liquid dispenser 400 can include the features of a track 430 and a base 432. The liquid dispenser 400 can include the features of a nut configured to interact with a ball screw, a motor 438, and a bearing. The liquid dispenser 400 can include the features of an inlet pressure port, an inlet vacuum port, a pressure channel, a vacuum channel, a pressure cross-channel, a vacuum cross-channel, a pressure port, a vacuum port, and one or more o-rings. The liquid dispenser 400 can include the features of a solenoid valve, and one or more tubes. The liquid dispenser 400 can include the features of a connector and circuit board of the of the pipette channel 410. The liquid dispenser 400 can include the features of a connector and circuit board of the manifold 402. The liquid dispenser 400 can include the features of a circuit board of the module 420. The liquid dispenser 400 can include the features of electrical connectors. The liquid dispenser 400 can include the features of a ribbon cable, a bend, and a groove. The liquid dispenser 400 can include any of the features of the liquid dispensers described herein.

Although certain features are not shown in FIGS. 56-57, example implementations of these features are described above with reference to liquid dispensers 1, 100, 200, and 300. For example, the nut, the ball screw, the bearing, the inlet pressure port, the inlet vacuum port, the pressure channel, the vacuum channel, the pressure cross-channel, the vacuum cross-channel, the pressure port, the vacuum port, the one or more o-rings, the solenoid valve, one or more tubes, the connector of the manifold, the circuit board of the manifold, the circuit board of the module, the electrical connectors, the ribbon cable, the bend, and the groove are not shown in FIGS. 56-57, but it will be understood that example implementations of these features are described above with reference to liquid dispensers 1, 100, 200, and 300 and are applicable to the liquid dispenser 400.

In some embodiments, the liquid dispenser 400 can include pipette channels 410 similar to pipette channels 210. In some embodiments, the liquid dispenser 400 can include manifold 402 similar to manifold 302. The manifold 402 is configured to accept one or more pipette channels 410. The inlet pressure port 442 can supply gas under pressure to one or more pressure cross-channels. The inlet vacuum port 444 can supply gas under vacuum to one or more vacuum cross-channels.

Example Liquid Dispensers According to the Present Disclosure

Figure 58:
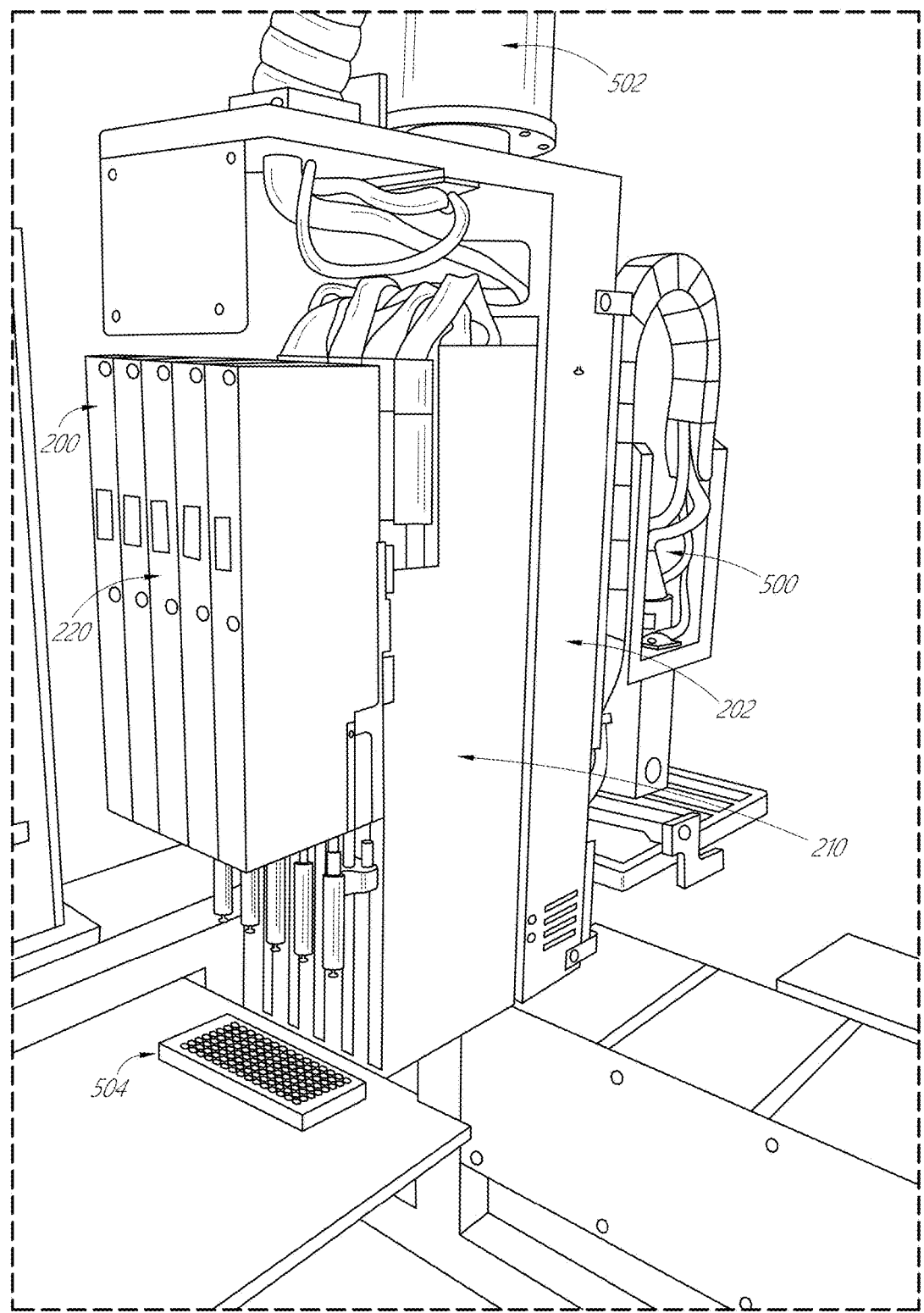
FIGS. 58-60 show views of the third embodiment.
Figure 59:
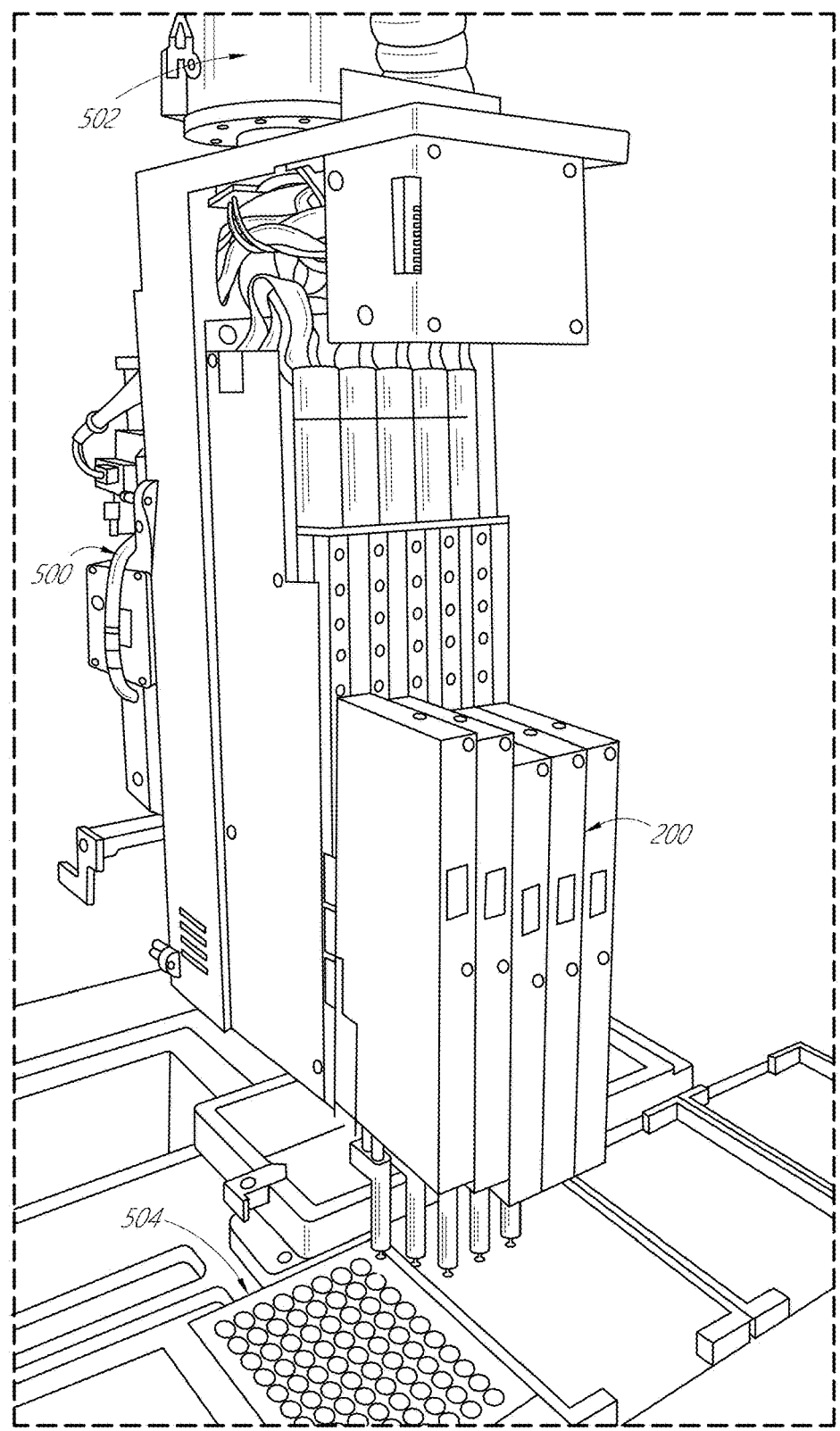
Figure 60:
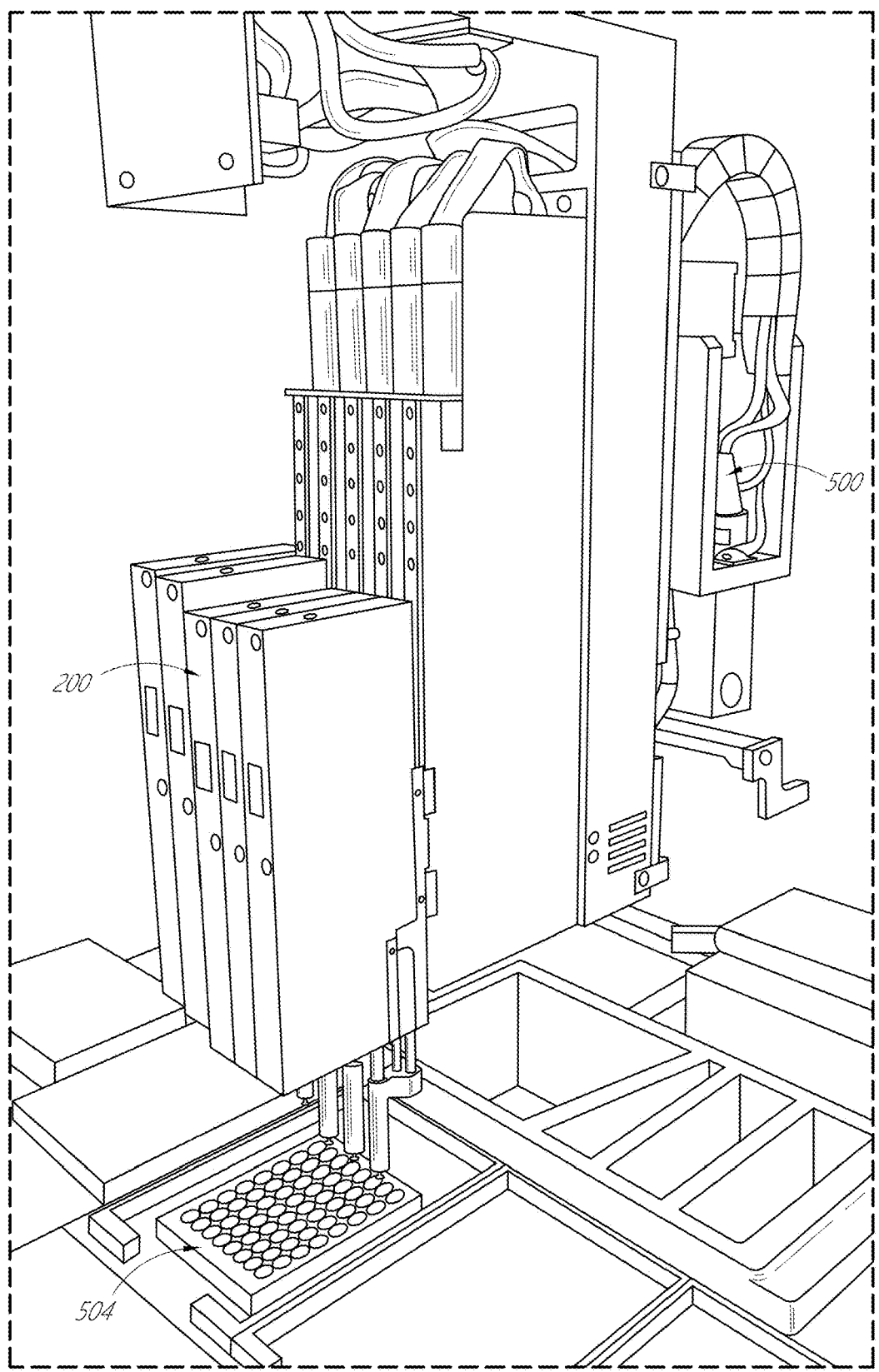
Figure 63:
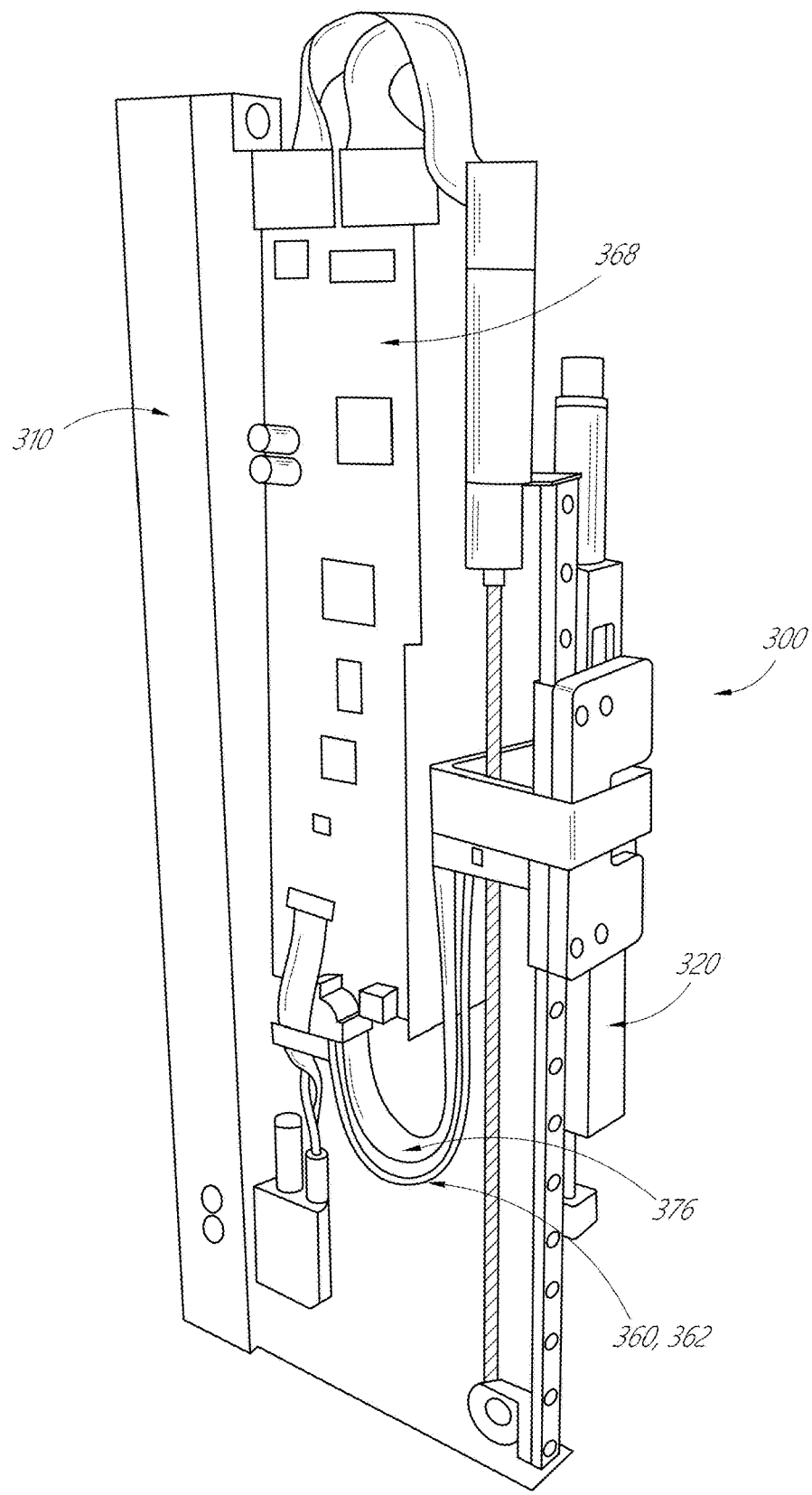
Figure 64:
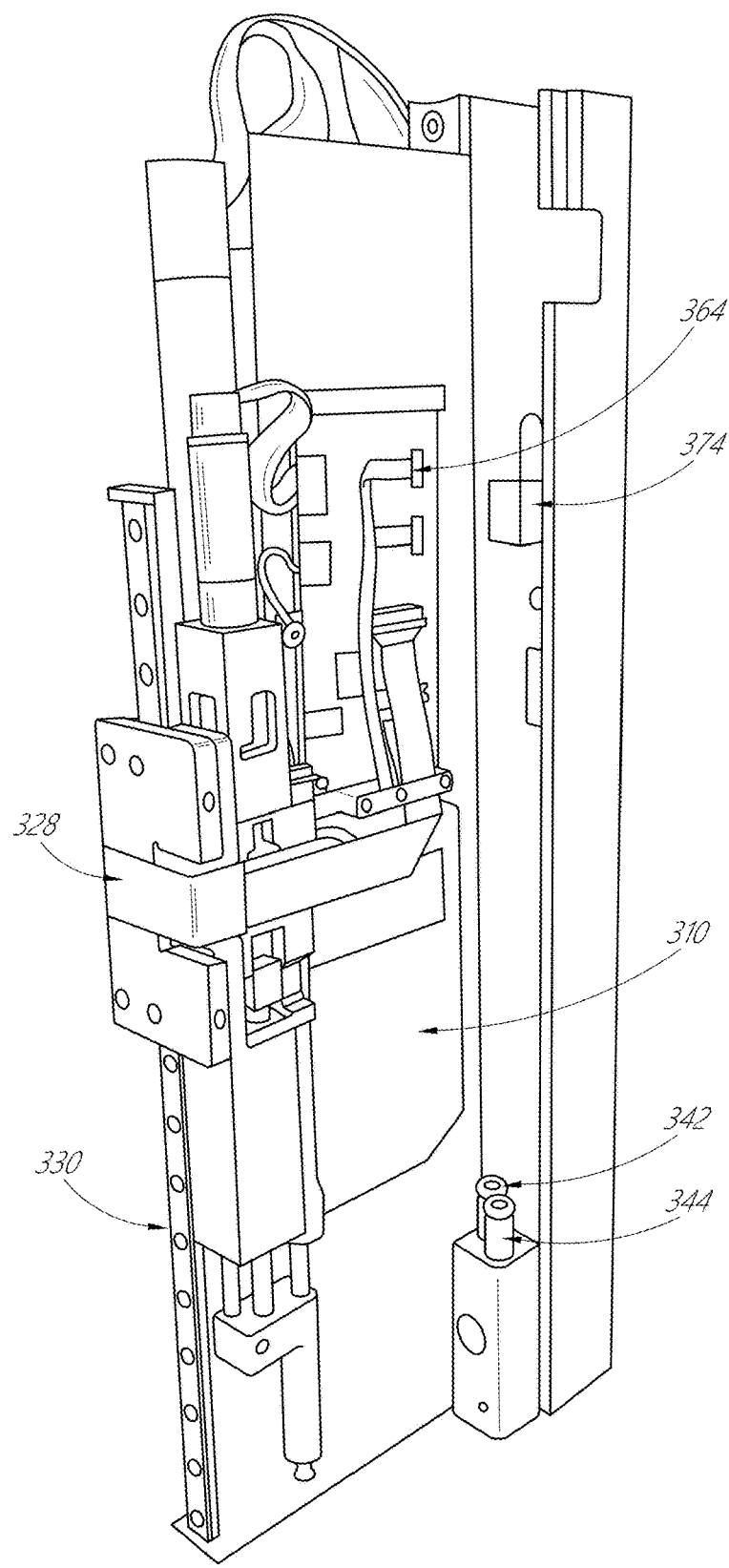

FIGS. 58-60 show views of the liquid dispenser 200 described above operably coupled to a robot 500. The robot 500 in this implementation is a separate robotic assembly that is used to perform various functions within a diagnostic testing system, for example pick up PCR plates in this example diagnostic testing system. The robot 500 travels with the liquid dispenser 200. In some embodiments, the robot 500 does not control the motion of the liquid dispenser. In some embodiments, the liquid dispenser 200 and the robot 500 are coupled to a robotic gantry (not shown) that has three degrees of freedom. The degrees of freedom can include movement in the X direction, Y direction, and rotation. In FIG. 58, the column 600 can connect to the robotic gantry (not shown). Any of the liquid dispensers described herein can be operably coupled to a robot 500. The manifolds 102, 202, 302, 402 can be coupled to a robotic arm of robot 500 which can move the manifold in space. The motion of the robotic arm can have six degrees of freedom. For example, the robotic arm can include 1 degree of translational freedom, 2 degrees of translational freedom, 3 degrees of translational freedom, 1 degree of rotational freedom, 2 degrees of rotational freedom, 3 degrees of rotational freedom, or any combination of these.

FIGS. 61-64 show views of interior portions of some features of the liquid dispenser 300 described above. The pipette channel 310 can be designed to accommodate internal wiring and tubing. The pipette channel 310 can include the tubes 360, 362 extending from the solenoid valve 358 to the module 320. The pipette channel 310 can include a ribbon cable 376 which transmits electrical signals and control signals. The ribbon cable 376 can extend from the connector 366 to the module 320. The tubes 360, 362, and the ribbon cable 376 can each include a bend 378. The bends 378 are shown in a downward position in FIG. 61. The downward position of the bends 378 in the tubes 360, 362 and the ribbon cable 376 corresponds to a downward position of the module 320. The bends 378 are shown in an upward position in FIG. 62. The upward position of the bends 378 corresponds to an upward position of the module 320. As the module 320 moves downward along the track 330 in the Z-direction, the bends 378 in the tubes 360, 362 and the ribbon cable 376 move downward within the base 332 of the pipette channel 310. The bends 378 can be accommodated within a groove 380 in the base 332 of the pipette channel 310.

In some embodiments, movement in the Z-direction of the pipette tip engaged to the module 320 relative to the manifold 302 is controlled by features housed in the pipette channel 310. The module 320 can include the flange 326. The flange 326 can be fixedly attached to the coupling 328. The coupling 328 is movable along the track 330. The movement of the coupling 328 in the Z-direction causes movement of the module 320 in the Z-direction relative to the track 330. The movement of the coupling 328 in the Z-direction causes movement of the module 320 in the Z-direction relative to the base 332 of the pipette channel 310.

The coupling 328 can include the nut 334. The nut 334 is configured to interact with the ball screw 336. The nut 334 can include ball bearings which reduce friction when interacting with the ball screw 336. In other embodiments, the nut 334 is threaded and interacts with a lead screw (not shown), rather than the ball screw 336 of this embodiment. The ball screw 336 can be rotated with the motor 338. As the ball screw 336 is rotated, the coupling 328 translates along the ball screw 336. The coupling 328 is guided along the track 330 in the Z-direction. Rotation of the ball screw 336 in a first direction causes the coupling 328 to translate downward in the Z-direction along the track 330. Rotation of the ball screw 336 in a second, opposite direction causes the coupling 328 to translate upward in the Z-direction along the track 330.

Additional Features of Liquid Dispensers Described Herein

The liquid dispensers described herein can be configured to carry out pipetting operations in parallel, with each pipette channel acting independently to aspirate and dispense liquid. Each pipette channel has the ability to move its corresponding pipette tip along the z-axis of the liquid dispenser independently of movement of another pipette tip mounted in the liquid dispenser. Thus, a liquid dispenser, as described herein, is an assembly of pipette channels that together cooperate to carry out such pipetting operations on solutions. The liquid dispenser thus, typically, can pick up and disengage pipette tips as needed, as well as aspirate quantities of liquid up into, and dispense those quantities of liquid from, such pipette tips. The motions and operation of the liquid dispenser is typically controlled by a processor such that pipetting operations can be automated. Advantageously, the liquid dispenser can be configured to align pipette tips, e.g., with containers or cartridge inlet holes.

Advantageously, the liquid dispenser can be configured so that the module circuit board, sensors (for example, but not limited to, sensors to detect presence of pipette tips and sensors to detect force exerted on pipette tips during pipetting), the tip eject motor, the sleeve, the pipette tip and other items, move as a unit as the module, thereby minimizing the number of control lines that move across the instrument during use, reducing the likelihood that such control lines will become tangled during motion of the module, and increasing the likelihood that the module will remain in communication with other components that are fixed at various points within a preparatory or diagnostic apparatus such as the base of the pipette channel and the manifold.

The layout of the components in the figures is for convenience only, and one of skill in the art would appreciate that other arrangements are possible, depending upon environment and other factors. The electrical components including the motors, pumps, and valves, can receive instructions from a processor (not shown). The processor can be located on the liquid dispenser or can be remote from the liquid dispenser.

Embodiments of liquid dispensers described herein can also include a sensor configured to sense when vertical motion of the module is obstructed, and to provide a suitable signal directly to a processor (not shown), or indirectly (not shown) via printed circuit board. The sensor can be mounted on the module or on another component of the pipette channel.

Optionally included within the liquid dispenser is a scanner (not shown). The scanner can be configured to read information (for example, but not limited to, sample and patient information), from one or more of a container holding a liquid, a sample tube, a reagent holder, a microfluidic cartridge, or any other container. The scanner can be electrically connected directly (not shown) to a processor, or indirectly via a printed circuit board.

Embodiments of liquid dispensers described herein include pneumatic solenoid valves, but other valves are contemplated. The valve can be associated with each pipette channel, and serve to control operation of each module such as by, for example, controlling when to reduce pressure, thereby causing a aspirating operation, or to increase pressure, thereby causing a dispense operation. Each valve is connected to (including being in fluid communication with) the module via one or more internal tubes which extend from the valve to the module.

The manifold of liquid dispensers described herein can be connected to a pump (not shown) via an air-line or tubing (not shown) to the inlet pressure port and inlet vacuum port. As described herein, the inlet pressure port and inlet vacuum port are connected via one or more channels and cross-channels in the manifold to ports in the pipette channel. The ports in the pipette channel supply gas under pressure and gas under vacuum to a valve located within the pipette channel. Each pipette channel contains an independently controllable solenoid valve that selectively diverts air from the pump to the module associated with the pipette channel, and therefore to a corresponding pipette tip.

Operation of liquid dispenser is typically controlled by one or more circuit boards (PCB), including circuit board 164 within the module 120. The PCB additionally can receive electrical signals from electrical connectors, including electrical connectors 170. Thus, the aspirate and dispense operations can be precisely controlled, by signals from the PCB, so that accurate volumetric control is achieved. In some embodiments, calibration of the liquid dispenser is required so that the amount of time to force or to aspirate gas that is required to dispense or aspirate a desired volume of liquid is known. Thus, according to one example, the time between a valve opening and valve closing, as controlled by signals, is known and can be incorporated into the control software. The liquid dispense operations can be controlled by the hardware and software located within the liquid dispenser. In some embodiments, the liquid dispense operations can be controlled by the hardware and software located within the module 120.

The module 120 can include the second valve, as described herein. The module 120 can include a pump (not shown) and a motor (not shown) controlling its action. In some embodiments, the pump includes a translating plunger controlled by a stepper motor, which receives electrical signals and/or control signals as input. The module 120 can include any hardware and/or software configured to complete aspirate and dispense operations, The above-described embodiments have been provided by way of example, and the present disclosure is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present development is not intended to be limited by the disclosed embodiments.

Embodiments of the pipette channel described herein are advantageously modular in design and thus compatible with any number of manifolds and modules. In the illustrated embodiments, the manifold can include one or more locations that accept a pipette channel. The locations on the manifold that accept a single pipette channel can be considered lanes. Each manifold can include one or more lanes (e.g., one lane, two lanes, three lanes, four lanes, five lanes, six lanes, a plurality of lanes, etc.). In some embodiments, the manifold includes two or more lanes. In some embodiments, each lane is adjacent to another lane. In some embodiments, each lane is configured to accept a pipette channel in a single orientation.

In some embodiments, each lane is configured to accept any pipette channel of a plurality of pipette channels. As one example, the pipette channel initially in one lane can be moved to another lane. In some embodiments, each lane is configured to accept a specific pipette channel. As one example, a pipette channel configured to perform aspirate and dispense operations only on reagents can be accepted into a specific lane or one of a plurality of specific lanes of the manifold. The reagents may be aspirated and dispensed from tubes that only contain reagents and do not contain sample swabs (such as a swab tip). As another example, a pipette channel configured to perform aspirate and dispense operations only on samples can be accepted into a specific lane or one of a plurality of specific lanes of the manifold. The samples may be aspirated and dispensed from tubes that contain samples and sample swabs (such as a swab tip). The ability to configure a manifold to accept one type of pipette channel in a first lane (for example, a pipette channel configured to aspirate and dispense fluids from reagent tubes) and to also accept a second, different type of pipette channel in a second lane (for example, a pipette channel configured to aspirate and dispense fluid from sample tubes) is particularly advantageous. In one example described in greater detail below, a pipette channel configured to perform aspirate and dispense functions on fluids in reagent tubes require the associated pipette tip to be coupled to the tip adapter with less force than a pipette channel configured to perform aspirate and dispense functions on fluids in sample tubes.

In some embodiments, a lane can be defined by one or more structures on the manifold. The lane can be defined by one or more openings configured to accept fasteners of the pipette channel. The lane can be defined by one or more openings configured to accept pegs of the pipette channel. The lane can be defined by an electrical connector configured to electrically connect to a corresponding electrical connector of a pipette channel mated with the manifold. In some embodiments, the lane can encompass only one electrical connector. The lane can be defined by the pressure channel configured to pneumatically connect to a corresponding pressure cross-channel of a pipette channel mated with the manifold. In some embodiments, the lane can encompass only one pressure channel. The lane can be defined by the vacuum channel configured to pneumatically connect to a corresponding vacuum cross-channel of a pipette channel mated with the manifold. In some embodiments, the lane can encompass only one vacuum channel.

In some embodiments, a lane can be configured to accept one or more components of the liquid dispenser. The lane can be defined by the location configured to accept a pipette channel. In some embodiments, each lane is configured to accept a single pipette channel. In some embodiments, a lane is configured to accept only one pipette channel. The lane can be defined by the location configured to accept a module. In some embodiments, each lane is configured to accept a single module. In some embodiments, a lane is configured to accept only one module.

In some embodiments, a lane and the one or more components of the liquid dispenser accepted thereon can be considered a unit. In some embodiments, a unit can be defined by function. The unit can be defined by the ability to perform aspirate and dispense operations. Two units of a liquid dispenser can perform the same aspirate and dispense operations simultaneously. Two units of a liquid dispenser can perform different aspirate and dispense operations simultaneously. Two units of a liquid dispenser can perform the same aspirate and dispense operations simultaneously. Two units of a liquid dispenser can independently control aspirate and dispense operations. Two units of a liquid dispenser can include two modules which independently perform aspirate and dispense operations. Two units of a liquid dispenser can independently control movement in the Z-direction. Two units of a liquid dispenser can include two valves which can independently select between vacuum and pressure. In one example, a unit includes a lane of the manifold and a selectively receivable component received in the lane. The selectively receivable component can include a pipette channel, a pipette module, a pipette channel coupled to a pipette module, or a blanking plate.

Advantageously, embodiments of the systems and methods described herein include the ability to control movements of the liquid dispenser, and in some cases to control movements of certain components the liquid dispenser independent of other components. In the illustrated embodiment, each pipette channel coupled to the manifold moves as a unit with the manifold. In some embodiments, the manifold can move in the X-direction, along the width of the manifold. The movement of the manifold in the X-direction causes movement in the X-direction of each pipette channel coupled to the manifold. In some embodiments, the manifold can move in the Y-direction, along the thickness of the manifold. The movement of the manifold in the Y-direction causes movement in the Y-direction of each pipette channel coupled to the manifold. In some embodiments, the manifold can move in the Z-direction, along the height of the manifold. The movement of the manifold in the Z-direction causes movement in the Z-direction of each pipette channel coupled to the manifold. In some embodiments, a pipette channel can move in the Z-direction independently of movement of the manifold. In some embodiments, a pipette channel coupled to the manifold can move in the Z-direction in the same direction as movement of the manifold. In some embodiments, a pipette channel coupled to the manifold can move in the Z-direction in the opposite direction as movement of the manifold.

In some embodiments, an advantage is the ability to mount the manifold to any of a variety of gantry systems with no or very little modification of the manifold. In some embodiments, the manifold is coupled to a gantry that is controlled by one or more belt drives. In some embodiments, the gantry is controlled by one or more stepper motors. In some embodiments, the gantry is controlled by one or more linear motors. In one example, a liquid dispenser system includes three manifolds, each mounted on a separate rail configured to travel along the Y-axis of the system. In such embodiments, the linear motors advantageously allow the multiple manifolds mounted on separate Y-direction rails to move along the same X-direction rail. In some embodiments, an advantage is that the linear motors allow three manifolds mounted on three separate Y-direction rails to move along the same X-direction rail.

In some embodiments, the pipette channel is calibrated for a specific function. In some embodiments, the pipette channel is configured in shape or design for a specific function. In some embodiments, the pipette channel is configured for a specific lane assignment. The pipette channel can dictate the lane where the pipette channel is placed. In some embodiments, two pipette channels coupled to a manifold have the same calibration settings. In some embodiments, two pipette channels coupled to a manifold have different calibration settings. In some embodiments, two pipette channels of two or more liquid dispensers have the same calibration settings. In some embodiments, two pipette channels of two or more liquid dispensers have different calibration settings.

In some embodiments, an advantage is the ability to select between two pipette channels with different calibration settings related to volume. A manifold can include one pipette channel with a selected calibration setting, multiple pipette channels configured with the same selected calibration setting, or multiple pipette channels configured with different selected calibration settings. As one example, a pipette channel can include be calibrated to dispense smaller volumes than another pipette channel mounted to the same manifold. As another example, a pipette channel can be calibrated to dispense greater volumes than another pipette channel mounted to the same manifold. In some embodiments, a pipette tip is mounted to a pipette channel configured to dispense 1 mL, of liquid. In some embodiments, a pipette tip is mounted to a pipette channel configured to dispense 5 mL of liquid. In some embodiments, a pipette tip is mounted to a pipette channel configured to dispense between 0.5 mL and 1 mL of liquid. In some embodiments, a pipette tip is mounted to a pipette channel configured to dispense between 1 mL and 5 mL of liquid. A plurality of pipette channels, each independently configured to dispense a particular volume, or range of volumes, can be selected and mounted to a manifold based on the particular liquid dispensing requirements of the system in which the manifold is installed.

In some embodiments, an advantage is the ability to select between two pipette channels with different calibration settings related to pressure. A manifold can include one pipette channel with a selected calibration setting, multiple pipette channels configured with the same selected calibration setting, or multiple pipette channels configured with different selected calibration settings. In some embodiments, a pipette tip is mounted to a pipette channel configured to dispense a liquid at 500 millibar. In some embodiments, a pipette tip is mounted to a pipette channel configured to dispense a liquid at between 250 millibar and 750 millibar. In some embodiments, a pipette tip is mounted to a pipette channel configured to dispense a liquid at less than 750 millibar. In some embodiments, a pipette tip is mounted to a pipette channel configured to dispense a liquid at less than 500 millibar. In some embodiments, a pipette tip is mounted to a pipette channel configured to dispense a liquid at less than 250 millibar. In some embodiments, the pressure is set by a pressure controller. The pressure controller can provide vacuum and pressure to the manifold. The pressure controller can provide instructions to control the vacuum and pressure supplied to the manifold. In some embodiments, all pipette channels coupled to a single manifold are provided with gas at the same pressure. For example, the system may include one pressure controller that feeds gas to the manifold, and all pipette channels coupled to the manifold are provided with gas at the same pressure. The pressure controller can change the pressure of the gas provided to all pipette channels coupled to the manifold.

Figure 65A:
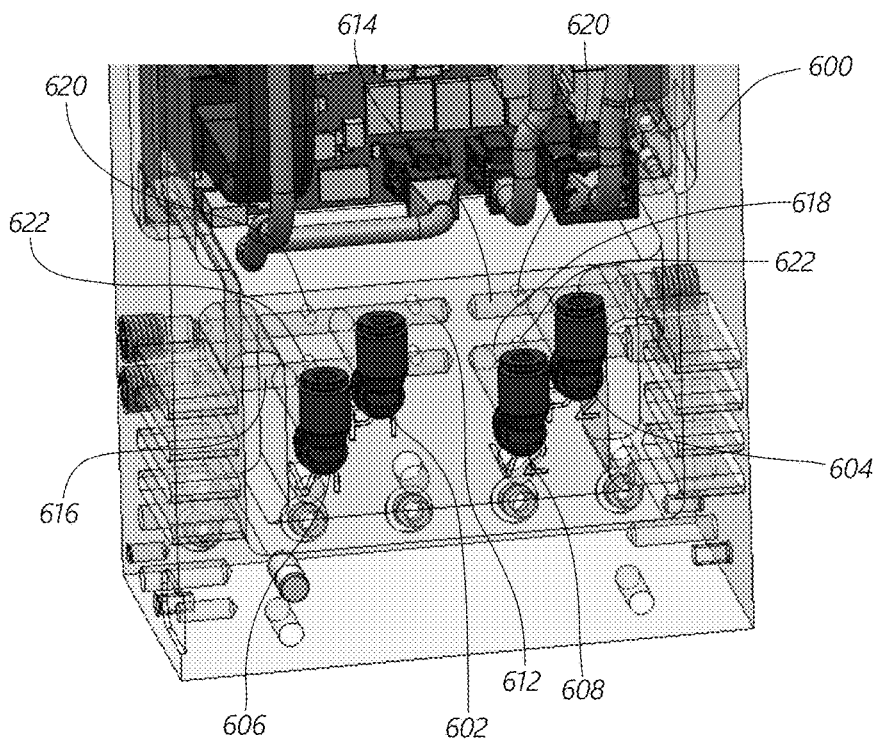
FIGS. 65A-65B show views of a manifold.
Figure 65B:
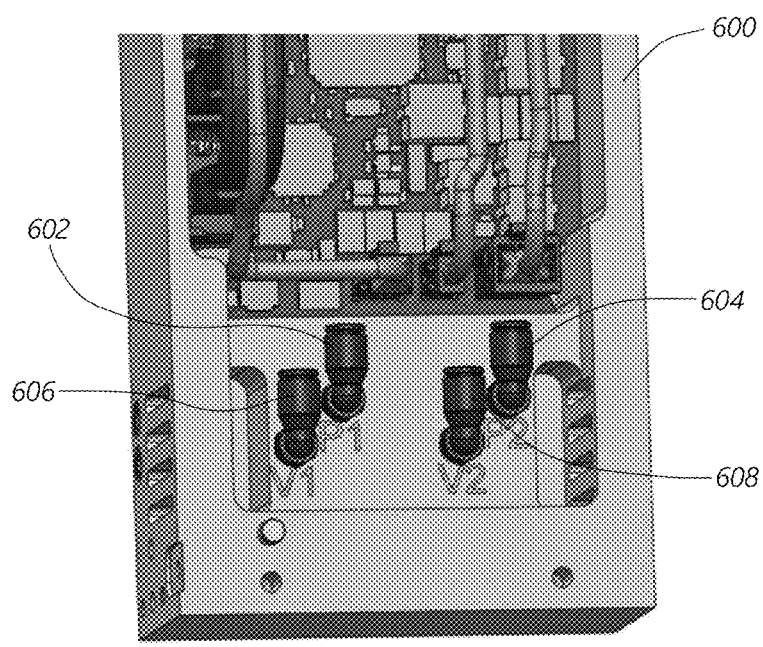

FIGS. 65A-65B illustrate an embodiment of the manifold 600, the features of which can be used in combination with any manifold described herein. In some embodiments, the manifold 600 is designed to provide gas to a first set of pipette channels coupled to a single manifold at a first pressure and to simultaneously provide gas to a second, different set of pipette channels coupled to the same single manifold at a second, different pressure. There are several ways to implement a manifold configured to supply gas under varying pressure. For example, the system can include two or more separate pressure controllers simultaneously providing gas at different pressures to the same single manifold. Other configurations are possible. Instead of one pressure inlet and one vacuum inlet, there could be a plurality of pressure inlets and/or a variety of vacuum inlets. For example, in some embodiments, there are two pressure sources and two vacuum sources connected to corresponding inlets e.g., pressure inlet 602, pressure inlet 604, vacuum inlet 606, and vacuum inlet 608 of the manifold 600. Each pressure source is connected to a single pressure channel and each vacuum source is connected to a single vacuum channel, such that the manifold has two pressure channels 612, 614 and two vacuum channels 616, 618. The manifold is split so the first pressure source and the first vacuum source supply gas to a first set of lanes of the manifold. The second pressure source and the second vacuum source supply gas to a second, different set of lanes of the manifold. The manifold can be divided in various combinations. In some embodiments, the pipette channels that receive gas from the same pressure channel and the same vacuum pressure channel are adjacent. The mating cross-channels, pressure cross-channel 620 and vacuum cross-channel 622, for the vacuum and pressure channels can be the same locations as other embodiments described herein. The cross-channels 620, 622 can be in the same position regardless of the number or location of the pressure channels and vacuum channels located within the manifold.

In an alternative embodiment (not illustrated), the manifold includes a first pressure channel that is physically and fluidically isolated from a second pressure channel, both of which are physically and fluidically isolated from a vacuum channel in the manifold. The valve of the pipette channel is coupled to the first pressure channel, the second pressure channel, and the vacuum channel and is designed to switch between the channels to divert gas at a first pressure from the first pressure channel, divert gas at a second, higher pressure from the second pressure channel, or divert gas under vacuum to the dispense head. In some embodiments, the valve of the pipette channel can be designed to switch between two or more vacuum channels in the manifold. Thus, in some embodiments, the valve of the pipette channel can be designed to switch between three or more channels supplying gas under pressure and/or gas under vacuum. In some embodiments, to allow each valve to switch between three channels, the pipette channel includes two solenoid valves in each pipette channel to distribute gas under pressure or gas under vacuum. The options for three gas sources include, but are not limited to, two pressure sources and one vacuum source; one pressure source and two vacuum sources, etc. For two pressure sources and two vacuum sources, the pipette channel may include three solenoid valves in each pipette channel to distribute gas under pressure or gas under vacuum. The manifold can be coupled to other types of pressure sources that separately supply gas under pressure and gas under vacuum to the valves in two or more pipette channels. A plurality of pipette channels, each independently configured to dispense a liquid at a different pressure, or range of pressures, can be selected and mounted to a manifold based on the particular liquid dispensing requirements of the system in which the manifold is installed.

In some embodiments, an advantage is the ability to select between two pipette channels with different calibration settings related to speed. A manifold can include one pipette channel with a selected calibration setting, multiple pipette channels configured with the same selected calibration setting, or multiple pipette channels configured with different selected calibration settings. As one example, a pipette channel can include a calibration for faster aspirate and dispense operations than another pipette channel, such as for high speed operations. As one example, a pipette channel can include a calibration for slower aspirate and dispense operations than another pipette channel.

In some embodiments, an advantage is the ability to select between two pipette channels with different calibration settings related to force. A manifold can include one pipette channel with a selected calibration setting, multiple pipette channels configured with the same selected calibration setting, or multiple pipette channels configured with different selected calibration settings. As one example, a pipette channel can be calibrated to engage or disengage a pipette tip with greater force than another pipette channel mounted to the same manifold. In one non-limiting implementation, a first pipette channel that interacts with one or more samples is configured to engage a pipette tip with greater force to prevent inadvertent disengagement of the pipette tip from the tip adapter by swabs within a sample tube. In another non-limiting example, a second pipette channel that interacts with reagents in reagent tubes is configured to engage a pipette tip with lesser force than the first pipette channel, because the second pipette channel will not interact with objects in a reagent tube that may inadvertently disengage the pipette tip, such as a sample swab.

Figure 35:
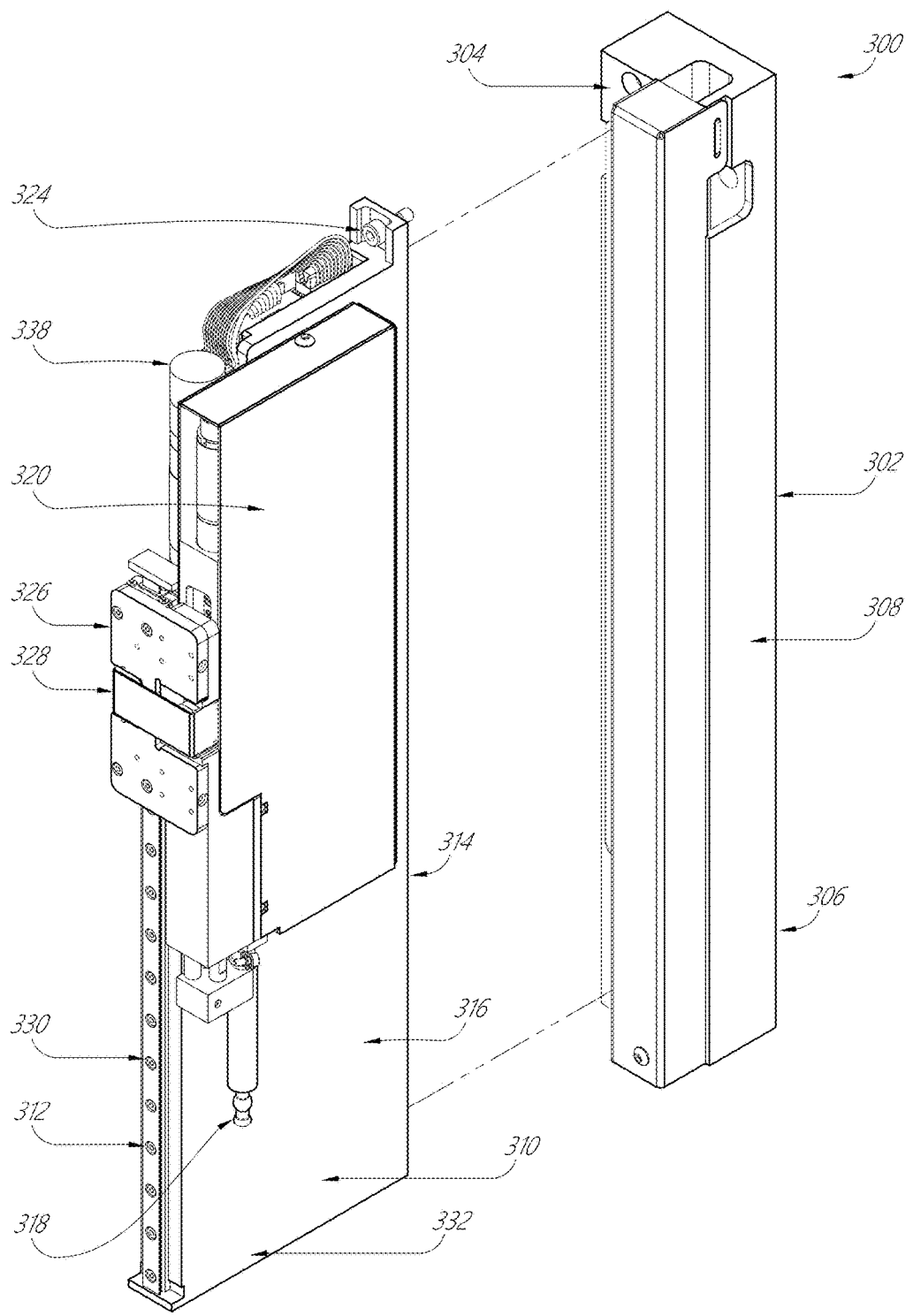
FIGS. 35-55 show views of a liquid dispenser according to a fourth embodiment.
Figure 36:
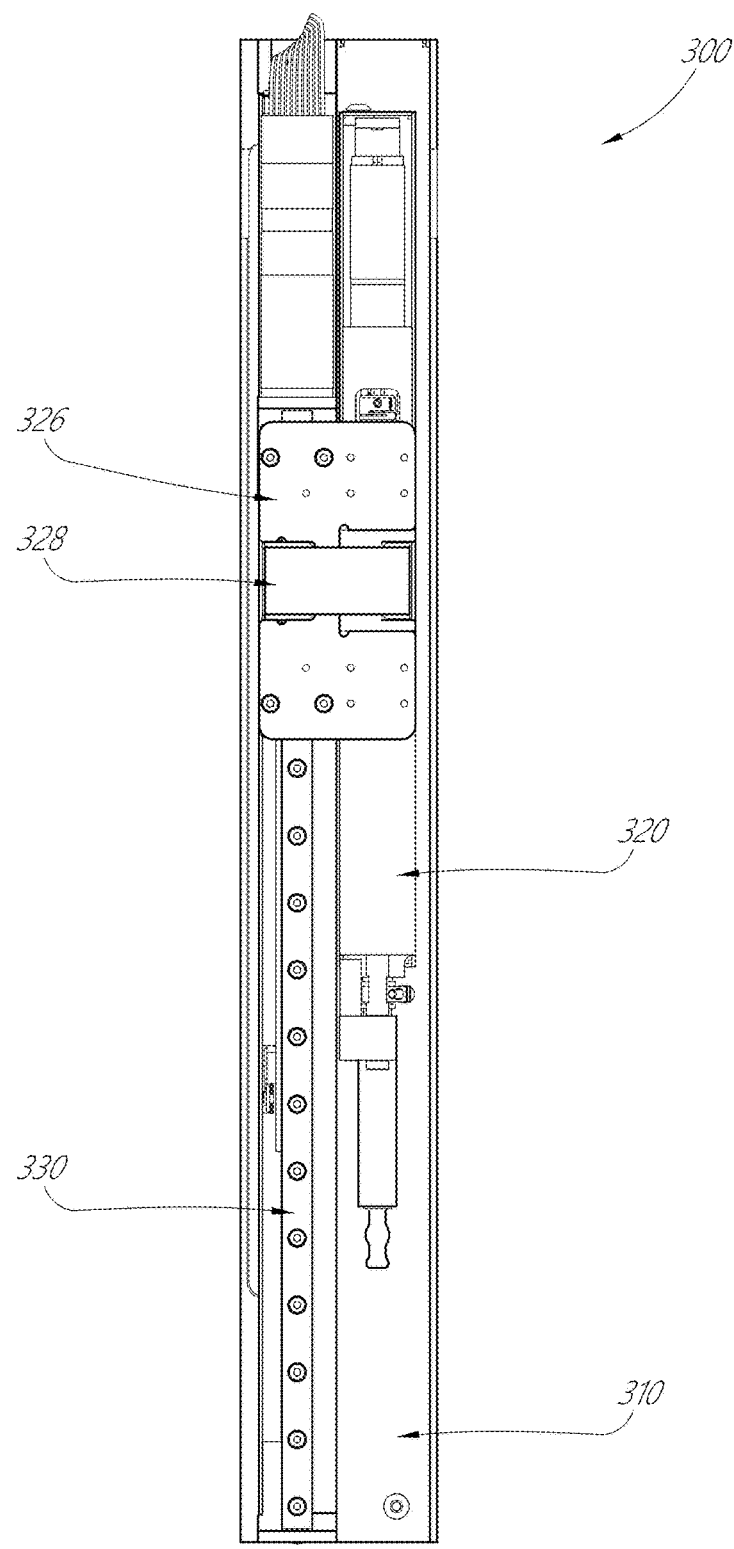
Figure 37:
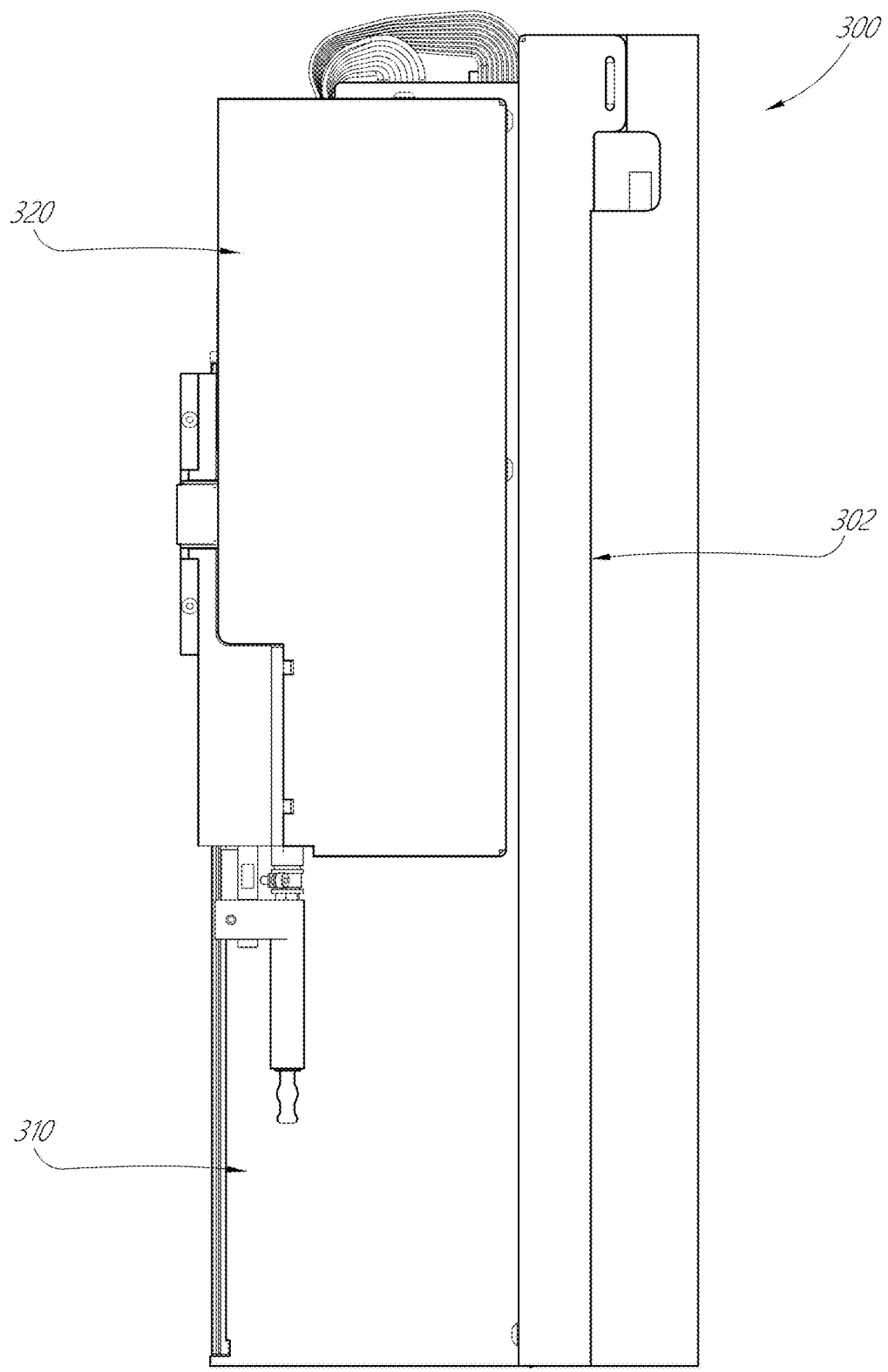
Figure 38:
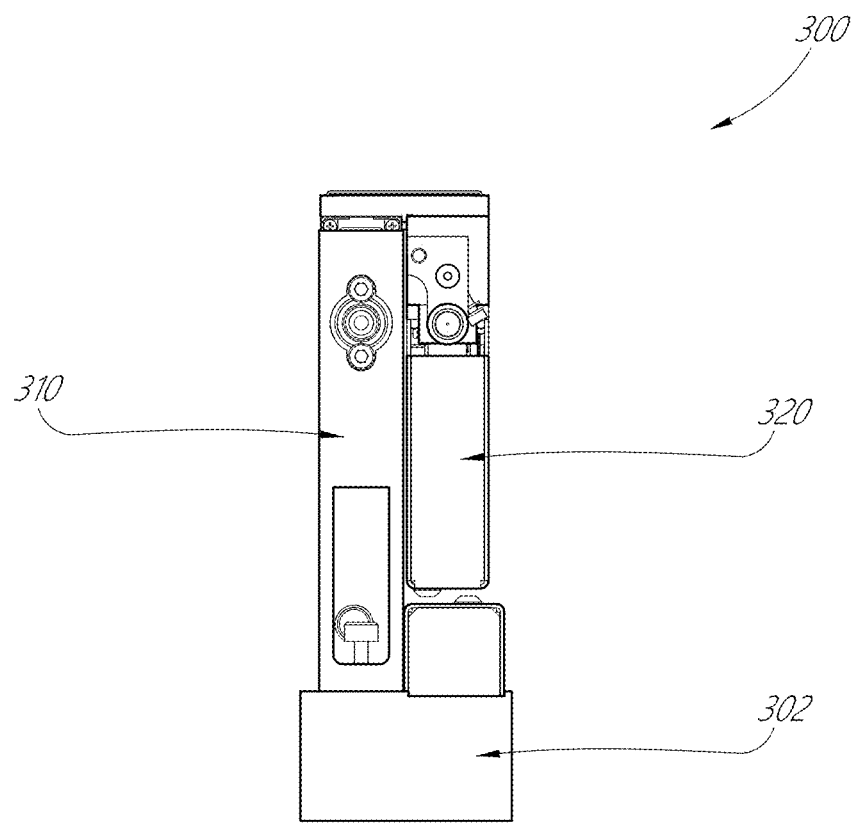

In some embodiments, an advantage is the ability to select between two pipette channels with different configurations. As one example, the two pipette tips can have different configurations related to differently sized pipette tip adapters. A manifold can include one pipette channel with a selected calibration setting, multiple pipette channels configured with the same selected calibration setting, or multiple pipette channels configured with different selected calibration settings, in some embodiments, two pipette channels can include different tip adapters. As one example, a pipette channel can include a larger tip adapter for a larger pipette tip than another pipette channel. As another example, a pipette channel can include more features than another, lower cost pipette channel. As another example, the two pipette channels can have a different configuration of the pipette module, for example, as shown in FIG. 35 where the pipette module 320 is mounted adjacent to a side 316 of the pipette channel 310 along the X-axis of the liquid dispenser 300.

In some embodiments, an advantage is the ability to design a liquid dispenser configured to accept two or more pipette channels that have different features, such as but not limited to different calibration settings or configurations. In some embodiments, the two or more different pipette channels can have the same configuration of electrical connectors designed to mate with the electrical connectors of the manifold. In some embodiments, the two or more different pipette channels can have the same configuration of pneumatic connections. In some embodiments, the two or more different pipette channels can have one or more different dimensions (e.g., height, thickness, width). In some embodiments, the two or more different pipette channels can have different modules. In some embodiments, the two or more different pipette channels can accept differently sized pipette tips some embodiments, the two or more different pipette channels can have different tip adapters. In some embodiments, the two or more different pipette channels can be calibrated to dispense fluids in different ways, such as but not limited to calibrated to dispense different volumes of fluid or calibrated to dispense fluid at different pressures. In some embodiments, two or more different pipette channels are configured to be accepted on any lane of the manifold.

In some embodiments, an advantage is the ability to design a manifold including two or more different lanes wherein each lane is configured to accept pipette channels that are the same. In some embodiments, the two or more different lanes can have the same configuration of electrical connectors within the lane. In some embodiments, the two or more different lanes can have the same configuration of pneumatic connection. In some embodiments, the two or more different lanes can have one or more different dimensions (e.g., height, thickness, width). In some embodiments, an advantage is the ability to design a manifold including two or more different lanes wherein each lane is configured to accept a pipette channel that is different from pipette channels mounted in other lanes.

In some embodiments, an advantage is the ability to design a system including two or more different liquid dispensers with different manifolds, the different manifolds having certain features in common and certain features which are different. In one example, one lane of each of the two or more different manifolds can have the same configuration of electrical connectors within the lane. In another example, one lane of each of the two or more different manifolds can have the same configuration of pneumatic connections. In some embodiments, one lane of each of the two or more different manifolds in the same system can have one or more different dimensions (e.g., height, thickness, width).

In some embodiments, an advantage is the ability to design a manifold configured to accept a specific number of pipette channels. In one implementation, the liquid dispenser includes one pipette channel but is configured to include more than one pipette channel. In another implementation, the liquid dispenser is configured to include only one pipette channel. In another implementation, the liquid dispenser includes three pipette channels but is configured to include more than three pipette channels. In another implementation, the liquid dispenser is configured to include only three pipette channels. In yet another implementation, the liquid dispenser includes five pipette channels but is configured to include more than five pipette channels. In another implementation, the liquid dispenser is configured to include only five pipette channels.

In some embodiments, an advantage is the ability to control the flow of a gas with a valve within a pipette channel. In the illustrated embodiments, a pipette channel includes an individually-actuatable solenoid valve. In some embodiments, the solenoid valve is a low pressure solenoid valve. In some embodiments, the solenoid valve is rated for less than 30 psi. In some embodiments, the solenoid valve is rated for less than 20 psi. In some embodiments, the solenoid valve is rated for less than 10 psi. In some embodiments, the solenoid valve is rated for between 5 and 10 psi. In some embodiments, the solenoid valve is rated for between 1 and 15 psi. In some embodiments, the solenoid valve is rated for between 1 and 20 psi. In some embodiments, the solenoid valve is optimized for low pressure applications. In some embodiments, the solenoid valve includes a diaphragm seal. In some embodiments, the solenoid valve includes a flexible seal. In the illustrated embodiments, the solenoid valve is located within a housing of the pipette channel. The solenoid valve is configured to control the flow of a gas from the manifold to the module of the pipette channel. The solenoid valve acts as a selector between vacuum and pressure.

In some embodiments, an advantage is the ability to control aspirate and dispense operations within a pipette channel. In some embodiments, a module of the pipette channel can include a second valve configured to control the aspirate and dispense operations. The second valve uses pressure and vacuum from the solenoid valve of the pipette channel to control the aspirate or dispense operations. Advantageously, in some systems described herein, each module mounted in a single manifold has simultaneous access to pressure. In some systems described herein, each module mounted has simultaneous access to vacuum. In some embodiments, each pipette channel includes an independent air-line that connects the module to the solenoid valve of the pipette channel. The air-lines described herein can accept any suitable gas, such as but not limited to atmospheric air or nitrogen. In the illustrated embodiment, an independent line that connects the module to the solenoid valve is enclosed within the housing of the pipette channel. In some embodiments, the independent line supplies both pressure and vacuum from the manifold to the module.

In some embodiments, an advantage is that each module includes an independent coupling to the manifold. In the illustrated embodiment, each pipette channel includes a single module. In the illustrated embodiment, each module is coupled to a single lane of the manifold. As described herein, each lane can include an independent electrical connection for the module. As described herein, each lane can include an independent pneumatic connection for the module.

In some embodiments, an advantage is the ability to have a system that can be tailored for a particular process. Systems described herein can be tailored for the demands of a laboratory. As one example, the system can be tailored based on the number of liquid dispensers employed. In some embodiments, a system can include one liquid dispenser, two liquid dispensers, three liquid dispensers, four liquid dispensers, five liquid dispensers, six liquid dispensers, seven liquid dispensers, eight liquid dispensers, nine liquid dispensers, ten liquid dispensers, etc. In some embodiments, each liquid dispenser includes a single manifold. In some embodiment, each manifold includes one or more pipette channels. In some embodiments, each pipette channel includes a single pipette module.

Systems described herein can be advantageously designed by a user that selects the number of liquid dispensers and the number of pipette channels. Two liquid dispensers of the system can have the same number of pipette channels (e.g., a system including two liquid dispensers each having one pipette channel, a system including two liquid dispensers each having two pipette channels, a system including two liquid dispensers each having three pipette channels, a system including two liquid dispensers each having four pipette channels, or a system including two liquid dispensers each having five pipette channels, etc.). Two liquid dispensers of the system can have a different number of pipette channels (e.g., a system including a liquid dispenser with one pipette channel in combination with a liquid dispenser with two pipette channels, three pipette channels, four pipette channels, or five pipette channels; a system including a liquid dispenser with two pipette channels in combination with a liquid dispenser with three pipette channels, four pipette channels, or five pipette channels; a system including a liquid dispenser with three pipette channels in combination with a liquid dispenser with four pipette channels or five pipette channels, a system including a liquid dispenser with four pipette channels in combination with a liquid dispenser with five pipette channels, etc.)

In some embodiments, an advantage is the ability to have two or more liquid dispensers of a system perform the same function. In some methods of use, two or more liquid dispensers of a system can receive instructions from a processor. The two or more liquid dispensers of a system can receive the same instructions to perform the same method. As one example, the two or more liquid dispensers can move in the same pattern of movements. As one example, the two or more liquid dispensers can perform the same method over the same period of time. As one example, one or more pipette channels of the two or more liquid dispensers can perform the same aspirate and dispense operations.

In some implementations, an advantage is the ability to have two or more liquid dispensers of a system perform different functions. Two or more liquid dispensers of a system can receive instructions from a processor. The two or more liquid dispensers of the system can receive different instructions to perform different methods. As one example, one liquid dispenser of a system can interact with one or more biological samples of one or more patients contained in sample tubes. Another liquid dispenser of the system can interact with one or more reagents contained in reagent tubes. The two or more liquid dispensers of the system can include different calibration settings, as described herein. As one example, the liquid dispenser of the system that interacts with one or more biological samples may be calibrated to require a greater force to engage and disengage pipette tips than the liquid dispenser of the system that interacts with one or more reagents. An advantage is that the greater force may reduce the disengagement of pipette tips due to swabs within the sample tubes. In some embodiments, the pipette channel that interacts with one or more biological samples may require at least 5 pounds of force to engage or disengage a pipette tip to a tip adapter. In some embodiments, the pipette channel that interacts with one or more biological samples may require at least 10 pounds of force to engage or disengage a pipette tip to a tip adapter. In some embodiments, the pipette channel that interacts with one or more reagents contained in reagent tubes may require less than 5 pounds of force to engage or disengage a pipette tip to a tip adapter. In some embodiments, the pipette channel that interacts with one or more reagents contained in reagent tubes may require less than 10 pounds of force to engage or disengage a pipette tip to a tip adapter.

Liquid dispensers described herein can be advantageously tailored for a particular process. In some embodiments, two pipette channels coupled to a manifold are similar or identical. As one example, two or more pipette channels of a liquid dispenser can perform the function (e.g., both pipette channels interact with one or more samples in sample tubes, both pipette channels interact with one or more reagents in reagent tubes, etc.). As another example, two or more pipette channels of a liquid dispenser can have the same shape or configuration. As a further example, two or more pipette channels of a liquid dispenser can have the same calibration settings.

In some embodiments, two pipette channels coupled to a manifold have different features. As one example, two or more pipette channels of a liquid dispenser can perform different functions (e.g., a pipette channel interacts with one or more samples in sample tubes and a pipette channel coupled to the same manifold interacts with one or more reagents in reagent tubes). As another example, two or more pipette channels of a liquid dispenser can be configured with different calibration settings. The pipette channel that interacts with one or more biological samples in sample tubes may be calibrated to engage and disengage pipette tips with a greater force than the pipette channel of the liquid dispenser that interacts with one or more reagents in reagent tubes. As a further example, two or more pipette channels of a liquid dispenser can have a different shape or configuration. As still another example, a liquid dispenser can have mixed-purpose pipette channels.

Processors in systems described herein can send instructions related to the pipette channel and the lane. In some embodiments, the processor sends instructions to each lane, and the components coupled to the lane, independently of instructions sent to another lane of the manifold. In some embodiments, the processor sends instructions to two or more lanes, and the components coupled to the two or more lanes, simultaneously. In some embodiments, the system may require identification of each pipette channel mounted to the manifold. In some embodiments, the system may require identification of each pipette channel mounted to the manifold and the corresponding lane in which each pipette channel is mounted.

In some embodiments, the processor sends instructions that direct the one or more pipette channels coupled to a manifold to transfer a sample from a container to another container. In some embodiments, the instructions employ a pipette channel of one or more pipette channels of a liquid dispenser to transfer a reagent from a container to another container, The instructions can include instructions to: employ the pipette channel to transfer a sample from a sample container to a reagent holder; employ the pipette channel to transfer a sample from a sample container to a microfluidic network; employ the pipette channel to direct a sample from the sample container to one or more additional containers; contact the pipette tip to a sample; contact the pipette tip to a reagent; to place the pipette tip in a container; to disengage or discard a used pipette tip and to engage an unused pipette tip. In various embodiments, a computer program product includes computer readable instructions thereon for operating one or more liquid dispensers. In some embodiments, a computer program product includes computer readable instructions thereon for causing the system to perform various aspirate and dispense operations.

Liquid dispensers described herein can recognize a pipette channel coupled to the manifold. In some embodiments, an advantage is the ability of a liquid dispenser to perform verification and validation of a pipette channel coupled to the manifold. In some embodiments, an advantage is the ability of a liquid dispenser to direct instructions to a single pipette channel of two or more pipette channels based on information obtained during a verification and validation process. In some embodiments, an advantage is the ability of a liquid dispenser to recognize which lane(s) of the manifold has a pipette channel mounted in the lane. In some embodiments, an advantage is the ability of a liquid dispenser to direct instructions to a lane of two or more lanes based on information about which lane(s) have a pipette channel mounted in the lane.

Liquid dispensers described herein advantageously reduce machine down time. Down time may require the system to stop operating and be powered down. The system may be powered down for any number of reasons, including but not limited to the liquid dispenser (or a component of the liquid dispenser) not operating properly; routine maintenance; to change a pipette channel mounted to the manifold to a pipette channel having different features; or to change a calibration setting of a pipette channel already mounted to the manifold. As one example, replacing one pipette channel of a liquid dispenser described herein can take less than one minute. In some methods of use, replacing one pipette channel of a liquid dispenser can take less than five minutes. In some methods of use, replacing one pipette channel of a liquid dispenser can take less than three minutes. In contrast, replacing a dispense head in a traditional liquid dispenser may include connecting and disconnecting pneumatic connections, connecting and disconnecting electrical connections, and/or connecting and disconnecting hardware connections. Replacing a dispense head in a traditional liquid dispenser can take over an hour. An advantage is a reduction in machine down time by over 95%. In some embodiments, the liquid dispenser described herein is configured to be operational 24 hours a day, seven days a week. In some embodiments, the liquid dispenser described herein is configured to be rapidly repaired in order to be operational nearly 24 hours a day, seven days a week.

In some embodiments, the method of replacing one pipette channel can include the step of unscrewing one or more fasteners. In some embodiments, the fasteners are two screws. In some embodiments, the two screws are captive screws. An advantage is that the screws remain with the pipette channel which prevents loss of the screws. An advantage is that the screws remain with the pipette channel which prevents use of the incorrect hardware. An advantage is that the captive screws increase the speed in which the pipette channel can be replaced. In some embodiments, the method of replacing one pipette channel can include the step of pulling the pipette channel away from the manifold. In some embodiments, the method of replacing one pipette channel can include the step of disengaging one or more pegs of the pipette channel from the manifold.

In some embodiments, the method of replacing one pipette channel can include the step of aligning one or more pegs of the replacement pipette channel with the manifold. In some embodiments, one or more pegs include two pegs. In some embodiments, one or more pegs engage corresponding openings in the manifold. In some embodiments, aligning one or more pegs of the replacement pipette channel also aligns one or more electrical connectors of the pipette channel with one or more electrical connectors of the manifold. In some embodiments, the one or more pegs extend beyond the electrical connectors of the pipette channel in the y-axis direction. As one example, see FIG. 47. An advantage is that the pegs of the pipette channel engage the manifold before the electrical connectors of the pipette channel engage the manifold. An advantage is that the one or more pegs may prevent damage to the electrical connectors. In some embodiments, aligning one or more pegs of the replacement pipette channel aligns one or more pneumatic connections of the pipette channel with the manifold. In some embodiments, aligning one or more pegs of the replacement pipette channel aligns the pressure channel of the manifold within the pressure cross-channel of the pipette channel. In some embodiments, aligning one or more pegs of the replacement pipette channel aligns the vacuum channel of the manifold within the vacuum cross-channel of the pipette channel. In some embodiments, the method of replacing one pipette channel can include the step of pushing the pipette channel toward the manifold. In some embodiments, the method of replacing one pipette channel can include the step of screwing two screws. In some embodiments, the step of screwing two screws also includes compressing two or more o-rings. An advantage is that an o-ring increases the seal between the pressure channel of the manifold and the pressure cross-channel of the pipette channel. An advantage is that an o-ring increases the seal between the vacuum channel of the manifold and the vacuum cross-channel of the pipette channel.

Embodiments of liquid dispensers described herein advantageously allow features in one lane of the manifold to be blocked when that lane is not in use. In some embodiments, a blanking plate can be installed in a lane of the manifold to block, or seal, features in the lane when a pipette channel is not mounted in the lane. The blanking plate can include one or more pegs. The blanking plate can include one or more screws. The blanking plate can cover the pneumatic connections of a lane, thereby closing off or sealing the pneumatic connections. The blanking plate can cover the one or more electrical connectors of the lane. An advantage is that the blanking plate can prevent damage to features in a lane when they are not in use. In some methods of use, the blanking plate is installed for prototyping. In some methods of use, the blanking plate is installed for troubleshooting. In some methods of use, the blanking plate can be installed to determine whether other lanes of the manifold are in operation. In some methods of use, one or more blanking plates can be installed to isolate a lane.

Systems described herein enable a liquid dispenser to be easily and quickly reconfigured. As one example, the liquid dispenser can be reconfigured if one or more pipette channels become inoperable. In some embodiments, one or more pipette channels can be replaced with a blanking plate. The blanking plate can limit the loss of pressure from the pressure channel of the manifold. The blanking plate can limit the loss of vacuum from the vacuum channel of the manifold. The blanking plate can enable operation of the liquid dispenser with the one or more remaining pipette channels.

In some embodiments, an advantage is the ability to rearrange the remaining pipette channels with respect to the manifold. In some embodiments, two or more pipette channels perform different functions. An advantage is that the user can remove a pipette channel performing a function and replace the pipette channel with a blanking plate. An advantage is that the user can move a pipette channel performing a first function to another location, such as another lane, of the manifold to perform a second, different function.

In some embodiments of pipette channels described herein, o-rings are captive. An advantage is that the o-rings remain with the pipette channel which prevents loss of the o-rings. Another advantage is that the o-rings remain with the pipette channel which prevents use of incorrectly sized o-rings. Captive o-rings can also increase the speed in which the pipette channel can be replaced. In some embodiments, the pipette channel includes a dove-tail o-ring groove. In some implementations, the opening of the o-ring groove is smaller in diameter than the o-ring. In some embodiments, the opening of the o-ring groove includes one or more tapered projections that interlock with the larger diameter of the o-ring once the o-ring is within the o-ring groove.

Systems described herein substantially reduce the likelihood of incorrectly connecting the electrical connectors between the pipette channel and the manifold, reducing the risk of damage to the electrical connectors. In the illustrated embodiments, the electrical connector of the pipette channel is automatically aligned with the electrical connector of the manifold when the pegs of the pipette channel are aligned.

In some embodiments, an advantage is the ability to substantially reduce the likelihood of incorrectly connecting pipette channels to electrical sources. In the illustrated embodiments, the manifold is connected to one or more outside sources (e.g., Ethernet connector, power connector, pipettor communication connector). In the illustrated embodiments, one or more pipette channels are connected to the outside sources via the manifold. In the illustrated embodiments, the manifold includes an internal system to distribute these connections to each of the pipette channels. In contrast, a traditional liquid dispenser may include separate electrical sources for each dispense head or pipettor. For instance, a traditional liquid dispenser having five pipettors may have five or more separate electrical sources. During installation or repair, these separate electrical sources may be connected to the incorrect pipettor or not connected to any pipettor. An advantage is reducing the likelihood of incorrectly connecting electrical sources to one or more pipette channels.

In some embodiments, an advantage is the ability to substantially reduce the likelihood of incorrectly connecting the pneumatic connections between the pipette channel and the manifold. In the illustrated embodiments, the pneumatic connections of the pipette channel are automatically aligned with the manifold when the pegs of the pipette channel are aligned. In the illustrated embodiments, the pressure cross-channel of the pipette channel is automatically aligned with the pressure channel of the manifold when the pegs of the pipette channel are aligned. In the illustrated embodiments, the vacuum cross-channel of the pipette channel is automatically aligned with the vacuum channel of the manifold when the pegs of the pipette channel are aligned.

In some embodiments, an advantage is the ability to substantially reduce the likelihood of incorrectly connecting the pneumatic sources. In the illustrated embodiments, the manifold is connected to one or more outside gas sources (e.g., via the inlet pressure port and the inlet vacuum port). In the illustrated embodiments, one or more pipette channels are connected to pressure and vacuum via the manifold. In the illustrated embodiments, the manifold includes an internal system of channels to distribute pressure and vacuum to each of the pipette channels. In contrast, a traditional liquid dispenser may include separate pneumatic sources independently connected to each dispense head or pipettor. For instance, a traditional liquid dispenser having five pipettors may have five separate pressure sources and/or five separate vacuum sources. During installation or repair, these separate pneumatic sources may be connected to the incorrect pipettor or not connected to any pipettor. An advantage is reducing the likelihood of incorrectly connecting pneumatic sources to one or more pipette channels.

Systems described herein advantageously allow an assembled, modular pipette channel to be supplied to an end user. In the illustrated embodiment, the pipette channel encloses a solenoid valve that controls whether gas under pressure or gas under vacuum is supplied to the module of a pipette channel. In the illustrated embodiment, the pipette channel encloses a secondary valve, such as a solenoid valve, to control aspirate and dispense operations within the module. In some embodiments, an advantage is the ability to return an assembled, modular pipette channel to the manufacturer. Advantageously, systems described herein include the ability to troubleshoot a malfunctioning or inoperative pipette channel apart from the manifold. In some cases, troubleshooting can be performed on a pipette channel that has been removed from the manifold, while the remaining pipette channels mounted to the manifold continue aspirate and dispense operations. In one non-limiting example, a malfunctioning or inoperative pipette channel is disengaged from the manifold in one minute or less, and a new pipette channel (or a blanking plate) is installed in the now-vacated lane of the manifold in one minute or less. Accordingly, in some implementations of systems described herein, a liquid dispenser can experience two minutes or less of downtime to replace a malfunctioning or inoperative pipette channel.

What is claimed is:

1. A liquid dispenser comprising:
   a manifold comprising a vacuum channel, a pressure channel, and a plurality of lanes, each lane comprising an electrical connector, a port to the pressure channel, and a port to the vacuum channel;
   one or more pipette channels, each pipette channel comprising a single dispense head and configured to couple to the electrical connector, the pressure port, and the vacuum port of any one lane of the plurality of lanes; and wherein each pipette channel comprises a first portion that does not move relative to the manifold when the pipette channel is coupled to the manifold and a second portion that moves relative to the manifold when the pipette channel is coupled to the manifold, wherein a valve is enclosed within the first portion of each pipette channel, the dispense head is coupled to the second portion, and a tube connecting the valve and the dispense head is configured to move within the first portion when the second portion moves relative to the first portion.

2. The liquid dispenser of claim 1, wherein the valve is configured to selectively distribute gas under pressure and gas under vacuum from the pressure port and the vacuum port, respectively, to the single dispense head.

3. The liquid dispenser of claim 1, wherein each of the one or more pipette channels are coupled to one lane of the plurality of lanes, and wherein, for each pipette channel, operation of the valve is independently controlled by signals transmitted to the valve via the electrical connector of the one lane to which the pipette channel is coupled.

4. The liquid dispenser of claim 1, wherein each pipette channel comprises an electrical connector, a pressure port, and a vacuum port.

5. The liquid dispenser of claim 4, wherein the electrical connector, the pressure port, and the vacuum port of any pipette channel is configured to couple to the electrical connector, the pressure port, and the vacuum port, respectively, of any one lane of the plurality of lanes.

6. The liquid dispenser of claim 4, wherein the electrical connector, the pressure port, and the vacuum port of the one or more pipette channels do not move relative to the manifold when the electrical connector, the pressure port, and the vacuum port of the one or more pipettes channels are coupled to the manifold.

7. The liquid dispenser of claim 1, wherein the single dispense head of the one or more pipette channels moves relative to the manifold when the one or more pipettes channels are coupled to the manifold.

8. The liquid dispenser of claim 1, comprising a plurality of pipette channels, wherein each lane of the plurality of lanes is configured to couple to any one pipette channel of the plurality of pipette channels.

9. The liquid dispenser of claim 1, wherein the pressure channel and the vacuum channel are physically and fluidically isolated from each other within the manifold.

10. The liquid dispenser of claim 1, wherein the manifold comprises a single pressure channel and a single vacuum channel.

11. The liquid dispenser of claim 1, wherein each pipette channel is configured to selectively couple and uncouple to the electrical connector, the pressure port, and the vacuum port of any one lane of the plurality of lanes.

12. The liquid dispenser of claim 1, wherein a longitudinal axis of each lane of the plurality of lanes is oriented transverse to the pressure channel.

13. The liquid dispenser of claim 1, wherein a longitudinal axis of each lane of the plurality of lanes is oriented transverse to the vacuum channel.

14. The liquid dispenser of claim 1, wherein the one or more pipette channels comprise a plurality of pipette channels, wherein at least one pipette channel of the plurality of pipette channels is coupled to one lane of the plurality of lanes, and wherein at least one lane of the plurality of lanes is not coupled to a pipette channel of the plurality of pipette channels.

15. The liquid dispenser of claim 14, further comprising a cover configured to seal the pressure port and the vacuum port of the at least one lane that is not coupled to a pipette channel of the plurality of pipette channels.

16. The liquid dispenser of claim 1, comprising only one pipette channel, wherein the pipette channel is coupled to one lane of the plurality of lanes, and wherein each of the remaining lanes of the plurality of lanes is not coupled to a pipette channel.

17. The liquid dispenser of claim 1, wherein each lane comprises a single port to the pressure channel and a single port to the vacuum channel.

18. The liquid dispenser of claim 1, comprising a first pipette channel coupled to a first lane of the plurality of lanes and a second pipette channel coupled to a second lane of the plurality of lanes, wherein the single dispense head of the first pipette channel aspirates a fluid at the same time the single dispense head of the second pipette channel dispenses a fluid.

19. The liquid dispenser of claim 1, wherein the one or more pipette channels comprises two pipette channels with different calibration settings related to pressure of gas in the dispense head during aspirate and dispense operations.

20. The liquid dispenser of claim 1, wherein the one or more pipette channels comprises two pipette channels with different calibration settings related to volume of fluid aspirated and dispensed during aspirate and dispense operations.

21. The liquid dispenser of claim 1, wherein the one or more pipette channels comprises two pipette channels with different calibration settings related to speed of aspirate and dispense operations.

22. The liquid dispenser of claim 1, wherein the one or more pipette channels comprise a plurality of pipette channels, wherein at least two of the plurality of pipette channels are identical.

23. The liquid dispenser of claim 1, wherein the one or more pipette channels comprise a plurality of pipette channels, wherein at least two of the plurality of pipette channels are different.

24. The liquid dispenser of claim 23, wherein the at least two different pipette channels have one or more different dimensions.

25. The liquid dispenser of claim 1, wherein each pipette channel comprises a valve operable to control the flow of gas within each pipette channel.

26. The liquid dispenser of claim 1, wherein each pipette channel comprises a valve operable to control the aspirate and dispense operations of the single dispense head of the pipette channel.

27. The liquid dispenser of claim 1, wherein each of the one or more pipette channels are selectively and independently coupled to the manifold.

28. The liquid dispenser of claim 1, wherein the pressure channel comprises a first end and a second end terminating at an inlet pressure port, wherein the inlet pressure port is connected to an external source of gas under pressure, wherein the vacuum channel comprises a first end and a second end terminating at an inlet vacuum port, and wherein the inlet vacuum port is connected to an external source of gas under vacuum.

29. The liquid dispenser of claim 28, wherein the manifold only accepts gas under pressure and gas under vacuum through the inlet pressure port and the inlet vacuum port, respectively.

30. The liquid dispenser of claim 1, wherein the electrical connector of each lane of the plurality of lanes is configured to transmit electrical signals from the manifold to one pipette channel, and wherein each pipette channel is configured, when coupled to the manifold, to be powered independently of any other pipette channel coupled to the manifold by the electrical signals transmitted from the manifold.

31. The liquid dispenser of claim 30, wherein each of the one or more pipette channels is coupled to the manifold, and wherein each of the one or more pipette channels only receives control signals and electrical signals through the electrical connector of the lane to which the respective pipette channel is coupled.

32. The liquid dispenser of claim 1, wherein at least one pipette channel further comprises a magnetic brake.

33. The liquid dispenser of claim 32, wherein the magnetic brake of the at least one pipette channel is configured to reduce free-fall of the single dispense head of the at least one pipette channel in the event of loss of electrical signals.

34. The liquid dispenser of claim 1, wherein at least one pipette channel further comprises a ball screw configured to move the single dispense head of the at least one pipette channel in a vertical direction relative to the manifold.

35. The liquid dispenser of claim 34, wherein the at least one pipette channel further comprises a coupling configured to reduce misalignment of the ball screw.

36. The liquid dispenser of claim 1, comprising a plurality of pipette channels coupled to the manifold, and wherein the pressure channel provides gas under pressure to all pipette channels coupled to the manifold at the same pressure.

37. The liquid dispenser of claim 1, comprising a plurality of pipette channels coupled to the manifold, and wherein the vacuum channel provides gas under vacuum to all pipette channels coupled to the manifold at the same pressure.

38. The liquid dispenser of claim 1, comprising a plurality of pipette channels coupled to the manifold, and wherein the manifold is operable to provide gas under pressure to a first set of pipette channels at a first pressure and to simultaneously provide gas to a second, different set of pipette channels at a second, different pressure.

39. The liquid dispenser of claim 1, wherein each pipette channel is configured to be selectively mounted to the manifold with two screws.

40. The liquid dispenser of claim 39, wherein the two screws are captive to the pipette channel.

41. The liquid dispenser of claim 1, wherein at least one pipette channel comprises one or more pegs configured to align with one or more openings of the manifold.

42. The liquid dispenser of claim 41, wherein the one or more pegs engage the one or more openings of the manifold before an electrical connector engages the pipette channel.

43. The liquid dispenser of claim 1, wherein each pipette channel comprises one or more o-rings configured to provide a seal between each pipette channel and the manifold.

44. The liquid dispenser of claim 43, wherein the one or more o-rings are captured in a dove-tail groove in each pipette channel.

45. The liquid dispenser of claim 1, wherein the one or more pipette channels comprises a first pipette channel and a second pipette channel coupled to the manifold.

46. The liquid dispenser of claim 45, wherein the first pipette channel comprises a different calibration setting for dispensing than the second pipette channel.

47. The liquid dispenser of claim 45, wherein the first pipette channel and the second pipette channel have different dispense heads.

48. The liquid dispenser of claim 1, further comprising a blanking plate configured to close one port to the pressure channel and one port to the vacuum channel of the manifold.

49. The liquid dispenser of claim 1, wherein each pipette channel comprises a valve configured to selectively distribute gas under vacuum and gas under pressure from the vacuum port and the pressure port, respectively, to the single dispense head, wherein each pipette channel further comprises a tube, the tube having a first end terminating at the valve and a second end terminating at the dispense head, and wherein the tube is configured to divert gas from the valve to the dispense head.

50. The liquid dispenser of claim 49, wherein the tube is the only pneumatic connection between the valve and the dispense head.

51. The liquid dispenser of claim 49, wherein the tube is configured to bend as the dispense head moves vertically relative to the manifold when the pipette channel is coupled to the manifold.

52. The liquid dispenser of claim 49, wherein the valve does not move vertically relative to the manifold when the pipette channel is coupled to the manifold, and wherein the tube is configured to bend within a housing of the pipette channel when the dispense head moves vertically relative to the manifold.

53. The liquid dispenser of claim 49, wherein the tube and the valve are enclosed within a first housing of the pipette channel and the dispense head is coupled to a second housing of the pipette channel enclosing a second valve.

54. The liquid dispenser of claim 49, wherein the tube is enclosed within an outer housing of the pipette channel.

55. The liquid dispenser of claim 1, wherein each pipette channel comprises a valve configured to selectively distribute gas under vacuum and gas under pressure from the vacuum port and the pressure port, respectively, to the single dispense head, and wherein each pipette channel further comprises a second valve that is configured to move with the dispense head when the pipette channel is coupled to the manifold.

56. The liquid dispenser of claim 55, wherein operation of each second valve is regulated independently of any other second valve by control signals transmitted from the manifold.

57. The liquid dispenser of claim 55, wherein the second valve is configured to control the aspirate and dispense operations of the dispense head.

58. The liquid dispenser of claim 55, wherein the second valve is a solenoid valve.

59. The liquid dispenser of claim 55, wherein the second valve is configured to control the amount of liquid aspirated or dispensed by the dispense head.

60. The liquid dispenser of claim 55, wherein the second valve is configured to control the timing of liquid aspirated or dispensed by the dispense head.

61. The liquid dispenser of claim 55, wherein each second valve is powered independently of any second valve by the electrical signals transmitted from the manifold.

62. The liquid dispenser of claim 1, wherein each pipette channel comprises a valve configured to selectively distribute gas under pressure and gas under vacuum from the pressure port and the vacuum port, respectively, to the single dispense head, and wherein each valve is a three way solenoid valve.

63. The liquid dispenser of claim 1, wherein each pipette channel is configured to be coupled and uncoupled from the manifold independently of another pipette channel coupled to the manifold.

64. The liquid dispenser of claim 1, wherein the one or more pipette channels comprises a plurality of pipette channels coupled to the manifold, wherein each dispense head of the plurality of pipette channels is moveable along a vertical direction relative to the manifold independently of another dispense head coupled to the manifold.

65. The liquid dispenser of claim 1, wherein the one or more pipette channels are modular.

66. The liquid dispenser of claim 1, wherein the one or more pipette channels comprises a plurality of identical pipette channels.

67. The liquid dispenser of claim 1, wherein the one or more pipette channels comprises a first pipette channel and a second pipette channel coupled to the manifold, wherein the first pipette channel and the second pipette channel are calibrated to aspirate and dispense a volume of liquid, and wherein the first pipette channel comprises a volume calibration setting that is different than the volume calibration setting of the second pipette channel.

68. The liquid dispenser of claim 1, wherein the one or more pipette channel comprises a first pipette channel and a second pipette channel coupled to the manifold, wherein the first pipette channel and the second pipette channel are calibrated to aspirate and dispense a liquid at a pressure, and wherein the first pipette channel comprises a pressure calibration setting that is different than the pressure calibration setting of the second pipette channel.

69. The liquid dispenser of claim 1, wherein the one or more pipette channel comprises a first pipette channel and a second pipette channel each comprising a pressure port and a vacuum port, and wherein the pressure port and the vacuum port of the first pipette channel have the same orientation of as the pressure port and the vacuum port of the second pipette channel.

70. The liquid dispenser of claim 69, wherein the first pipette channel and the second pipette channel have one or more different dimensions.

71. The liquid dispenser of claim 69, wherein the first pipette channel and the second pipette channel perform different functions simultaneously.

72. The liquid dispenser of claim 1, wherein the liquid dispenser has 3 pipette channels coupled to the manifold.

73. The liquid dispenser of claim 1, wherein the liquid dispenser has 5 pipette channels coupled to the manifold.

74. The liquid dispenser of claim 1, wherein each dispense head is independently movable in a vertical direction relative to the manifold when the dispense head is coupled to the manifold via its respective pipette channel.

75. The liquid dispenser of claim 1, wherein each pipette channel comprises a pipette tip sensor configured to detect whether a pipette tip is engaged with the dispense head.

76. The liquid dispenser of claim 1, wherein each pipette channel comprises a sensor configured to sense when vertical motion of the dispense head is obstructed.

77. The liquid dispenser of claim 1, further comprising two or more pipette channels coupled to the manifold, wherein each valve of the two or more pipette channels is configured to be individually actuated to selectively divert gas under vacuum or gas under pressure from the manifold to each dispense head.

* * * * *